(12) United States Patent
Gruentzig

(10) Patent No.: US 10,874,152 B2
(45) Date of Patent: Dec. 29, 2020

(54) WEARABLE DEVICE FOR REDUCING FLUID LOSS

(71) Applicant: Legionarius, LLC, Sudbury, MA (US)

(72) Inventor: Alexander Gruentzig, Sudbury, MA (US)

(73) Assignee: Legionarius, LLC, Sudbury, MA (US)

( * ) Notice: Subject to any disclaimer, the term of this patent is extended or adjusted under 35 U.S.C. 154(b) by 0 days.

(21) Appl. No.: 15/306,577

(22) PCT Filed: May 1, 2015

(86) PCT No.: PCT/US2015/028912
§ 371 (c)(1),
(2) Date: Oct. 25, 2016

(87) PCT Pub. No.: WO2015/183470
PCT Pub. Date: Dec. 3, 2015

(65) Prior Publication Data
US 2017/0049164 A1    Feb. 23, 2017

Related U.S. Application Data

(60) Provisional application No. 61/987,130, filed on May 1, 2014.

(51) Int. Cl.
*A41D 13/018*    (2006.01)
*F41H 1/02*    (2006.01)
(Continued)

(52) U.S. Cl.
CPC .......... *A41D 13/018* (2013.01); *A41D 1/002* (2013.01); *A41D 1/04* (2013.01); *A41D 1/06* (2013.01);
(Continued)

(58) Field of Classification Search
CPC . A61B 17/132; A61B 17/1325; A61B 17/135; A61B 17/1355;
(Continued)

(56) References Cited

U.S. PATENT DOCUMENTS 3,933,150 A    1/1976 Kaplan et al.
5,090,053 A *  2/1992 Hayes ................ A41D 13/0053
                                                             2/2.5
(Continued)

FOREIGN PATENT DOCUMENTS

WO    WO-2007/142887 A1    12/2007
WO    WO-2015/183470 A2    12/2015
WO    WO-2018/213615 A2    11/2018

OTHER PUBLICATIONS

International Search Report and Written Opinion for International Patent Application No. PCT/US2015/28912, dated Dec. 29, 2015 (21 pages).
(Continued)

*Primary Examiner* — Martin T Ton
(74) *Attorney, Agent, or Firm* — Clark & Elbing LLP

(57) ABSTRACT

The invention features methods and devices for controlling bleeding from blood vessels that may be damaged as a result of trauma or impact with an object, such as a bullet or shrapnel. The device may be wearable by a user and include one or more components, such as wound sealant and multiple inflatable balloons/bladders. The device may be integrated into a garment, e.g., a vest, jacket, trousers, or full body suit. Once triggered (automatically or manually), the device may be used to deliver wound sealant to a wound site and/or pressure to the wound site by selective inflation of one or more balloons over exsanguinating blood vessels that may be damaged, thereby stopping or minimizing the bleeding. Alternatively, or in addition, the device may be used to stabilize a wounded wearer for, e.g., transportation purposes, (Continued)

or to provide buoyancy. Devices of the invention may also be used as a blood pressure monitor, as a massaging device, and as a breast pump. Devices and methods of the invention may also be used for repairing or stabilizing machines, such as vehicles (e.g., automobiles and boats).

40 Claims, 31 Drawing Sheets

(51) Int. Cl.
| | | |
|---|---|---|
| A41D 1/00 | (2018.01) | |
| A61B 17/00 | (2006.01) | |
| A41D 1/04 | (2006.01) | |
| A41D 1/06 | (2006.01) | |
| A41D 3/00 | (2006.01) | |
| A41D 13/02 | (2006.01) | |
| A42B 3/04 | (2006.01) | |
| F41J 5/00 | (2006.01) | |
| F41J 5/04 | (2006.01) | |
| F41J 5/24 | (2006.01) | |

(52) U.S. Cl.
CPC ............... *A41D 3/00* (2013.01); *A41D 13/02* (2013.01); *A42B 3/046* (2013.01); *A61B 17/00* (2013.01); *F41H 1/02* (2013.01); *A61B 2017/00557* (2013.01); *F41J 5/00* (2013.01); *F41J 5/04* (2013.01); *F41J 5/24* (2013.01)

(58) Field of Classification Search
CPC ........ A61B 2017/00557; A41D 13/018; A41D 13/0155; A41D 2400/14; F41H 1/02; Y10S 2/03
USPC .................................................. 606/201–203
See application file for complete search history.

(56) References Cited

U.S. PATENT DOCUMENTS

| | | | |
|---|---|---|---|
| 5,195,752 A | 3/1993 | Reeves et al. | |
| 5,636,378 A | 6/1997 | Griffith | |
| 5,867,842 A * | 2/1999 | Pinsley | A41D 13/018 2/462 |
| 6,012,162 A * | 1/2000 | Bullat | A41D 13/018 2/2.5 |
| 6,032,299 A * | 3/2000 | Welsh | A41D 13/018 2/456 |
| 6,042,147 A | 3/2000 | Nishijima et al. | |
| 6,349,201 B1 * | 2/2002 | Ford | H04B 1/385 2/455 |
| 6,757,916 B2 * | 7/2004 | Mah | B64D 10/00 2/2.14 |
| 6,939,314 B2 | 9/2005 | Hall et al. | |
| 6,997,218 B1 * | 2/2006 | Garcia | F41H 1/02 141/98 |
| 7,056,179 B2 * | 6/2006 | Courtney | B63C 9/0005 441/90 |
| 7,329,792 B2 | 2/2008 | Buckman et al. | |
| 7,548,168 B2 * | 6/2009 | Ishikawa | A41D 13/018 2/455 |
| 7,921,472 B2 * | 4/2011 | Mazzarolo | A41D 13/018 2/108 |
| 8,079,247 B2 * | 12/2011 | Russell | A42B 3/046 73/12.01 |
| 2005/0067816 A1 * | 3/2005 | Buckman | A41D 13/018 280/730.1 |
| 2007/0061941 A1 * | 3/2007 | Makabe | A41D 13/018 2/102 |
| 2008/0105114 A1 * | 5/2008 | Gabrys | B32B 3/18 89/36.02 |
| 2010/0083733 A1 | 4/2010 | Russell et al. | |
| 2011/0204114 A1 * | 8/2011 | Miller | A45F 3/04 224/582 |
| 2012/0102630 A1 * | 5/2012 | Anderson | A42B 3/0486 2/413 |
| 2012/0118449 A1 | 5/2012 | Barnes et al. | |
| 2012/0144934 A1 | 6/2012 | Russell et al. | |
| 2012/0180179 A1 | 7/2012 | Lee et al. | |
| 2012/0246788 A1 | 10/2012 | Harrell et al. | |
| 2013/0058906 A1 * | 3/2013 | Turzi | A61K 31/728 424/93.7 |
| 2013/0131566 A1 | 5/2013 | Bodansky | |
| 2014/0023579 A1 | 1/2014 | van Vliet et al. | |
| 2015/0173433 A1 * | 6/2015 | Mazzarolo | A41D 13/018 2/461 |
| 2019/0208841 A1 | 7/2019 | Gruentzig | |

OTHER PUBLICATIONS

International Preliminary Report on Patentability for International Patent Application No. PCT/US2015/028912, dated Nov. 1, 2016 (11 pages).

International Search Report and Written Opinion for International Patent Application No. PCT/US2018/033241, dated Aug. 13, 2018 (11 pages).

* cited by examiner

FIG. 1A
FIG. 1B
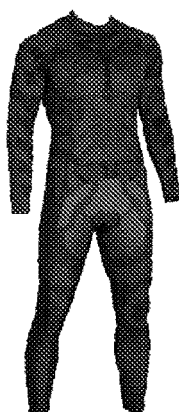
FIG. 1C
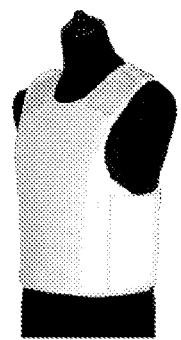
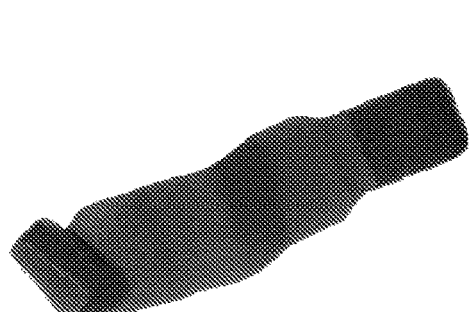
FIG. 1D
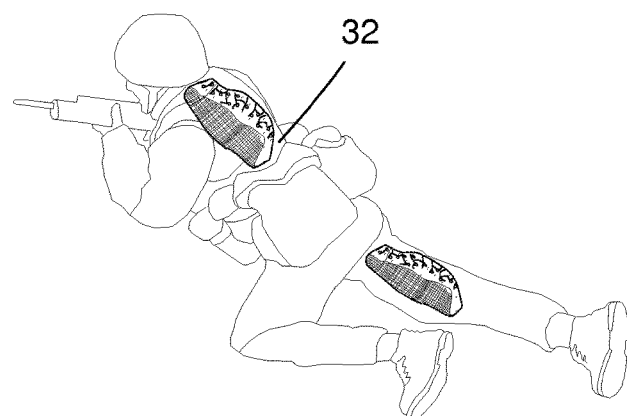
FIG. 1E
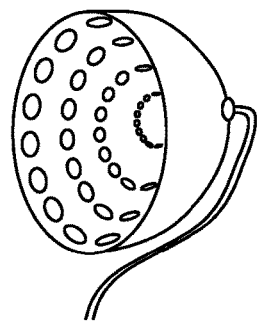
FIG. 1F

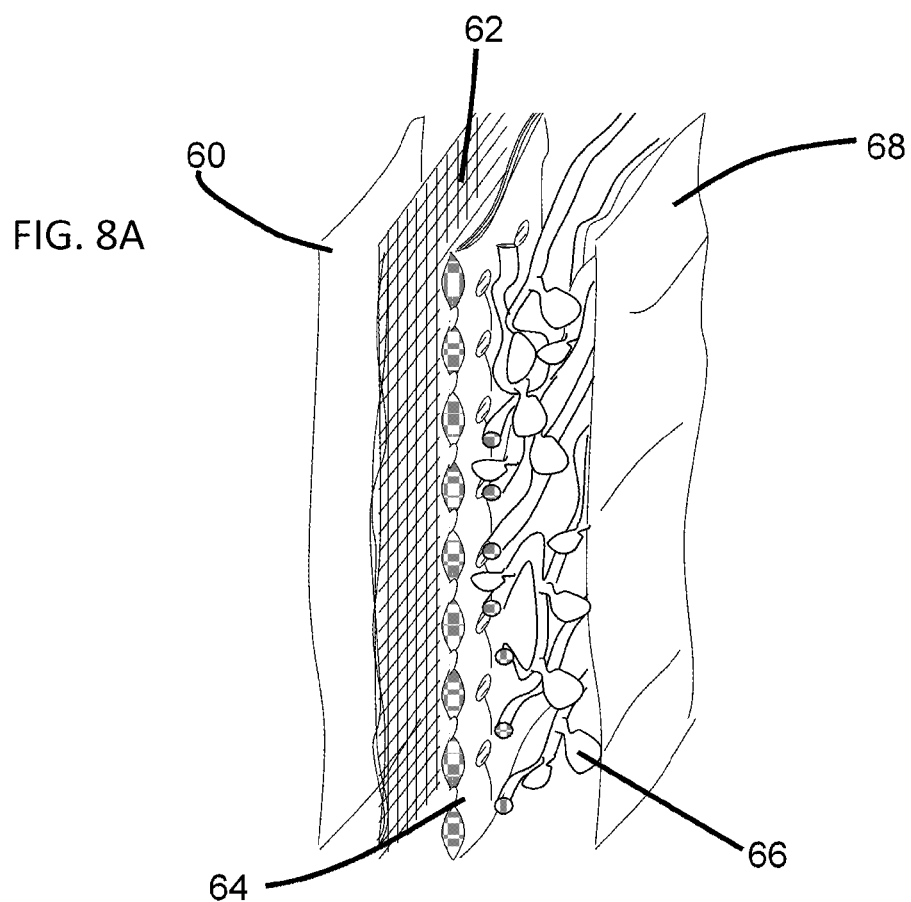

Symbolized Central Unit

Detail

FIG. 22A  FIG. 22B  FIG. 22C  FIG. 22D
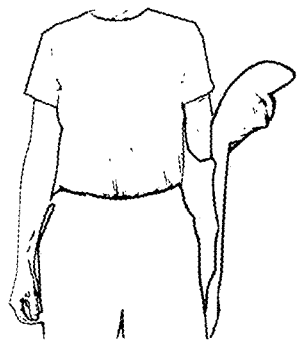  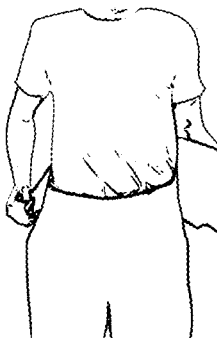 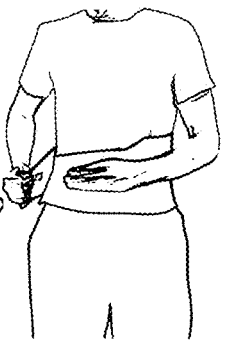
FIG. 22E  FIG. 22F  FIG. 22G  FIG. 22H
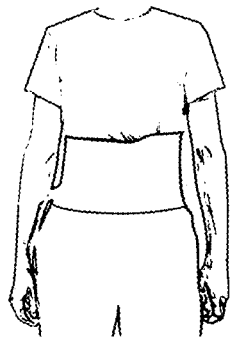  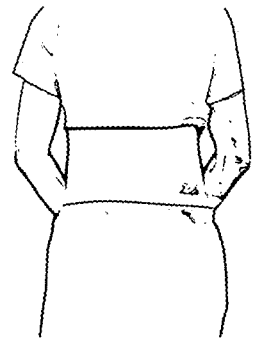 

Time since Impact:
N/A

Time since Impact:
0 s

Time since Impact:
1 s

**Time since Impact:
25 s**

*Photo of site of impact ("User's wound site"). Quarter displayed for size comparison*

WEARABLE DEVICE FOR REDUCING FLUID LOSS

BACKGROUND OF THE INVENTION

Hemorrhage from vascular injuries in the proximal extremities, pelvis, and abdomen is extremely difficult to treat. While the treatment of such injuries is challenging when they occur in civilian populations, they are even more difficult to treat in combat situations. While improvements in body armor have reduced mortality from combat injuries to the chest, the incidence of penetrating injuries to the extremities and their associated mortality remain high. It has been estimated that a well-designed battlefield tourniquet could potentially prevent 10% of all combat deaths due to exsanguinating peripheral vascular wounds. While it is gratifying that recent robust efforts have developed to create better tourniquets for treatment of these wounds, there remains a very important subset of lower extremity wounds in the region of the groin that cannot be treated with traditional tourniquets. Although the exact percentage of these wounds is unknown, both military and civilian reports detail the challenges in controlling ongoing hemorrhage of vascular injuries in this anatomical area especially in the pre-surgical time period.

Clearly, wounds to the groin, pelvis, and abdomen are complex and may involve several systems either alone or in combination, including major vascular structures, the bony pelvis, solid organs such as the liver and spleen, and even hollow organ injury to the bowel and bladder. Wounds directly involving isolated major vascular structures above the level of the femoral artery and vein such as the iliac artery and veins are most challenging to treat followed by complex bony pelvic injuries from high velocity penetrating trauma resulting in complex arterial and lower pressure venous bleeding similar to those of blunt pelvic injuries experienced in a civilian trauma center.

Lastly even injuries involving isolated major vascular injury at or just above the inguinal ligament pose a tremendous field challenge in creating hemostasis. The femoral artery is usually palpable at the level of the inguinal ligament. Despite this, the ability to control bleeding by application of direct pressure by either the injured combatant or by others including fellow soldiers or medic aides will usually not suffice especially if rapid manual transport must take place. Controlling hemorrhage by application of direct manual pressure may be particularly challenging in cases where there is no large tissue defect allowing for packing and more pressure in closer proximity to the injured vessels. In fact, currently the only way to address this is by exploring the wound site, locating the artery and clamping it with hemostats. For deeper vascular injuries to the pelvis and abdomen, exploration is not an option until the time of surgery.

Similarly, cardiopulmonary resuscitation (CPR) to "restart" the heart of an injured patient is frequently necessary in emergency situations. During the period of time when a heart is not beating, and until it regains the ability to do so, it is imperative that respiration (i.e., lung inflation and deflation) be maintained so that blood circulation continues. It is especially essential to maintain blood circulation to the heart and brain during this time, or serious irreversible damage can occur. Even when a trained first aid provider performs chest compressions in these circumstances, blood flow in the victim may still be well below normal (e.g., 20-30%).

In emergency medicine, the golden time refers to a time period lasting from a few minutes to several hours following a traumatic injury, during which there is the highest likelihood that prompt medical treatment will prevent death. It is well established that a patient's chances of survival are greatest if they receive care within a short period of time after a severe injury.

There is an ongoing need to provide adjunct therapies and devices that can aid in the control or maintenance of blood flow, or to prevent blood loss, during emergency situations, including, for example, those that may require CPR. It would be therefore of great benefit to have a device that could provide aid during such emergency situations, and that could be automatically (or manually) employed in a quick and straight forward manner. It would be especially desirable to have available a device that is 1) wearable and that would be able to do one or more of the following: 2) to control bleeding, 3) to assist with CPR, 4) to stabilize all, or part of, the body, 5) to provide buoyancy, 6) to create a water tight seal, 7) to allow for oscillating and/or massaging pressure applications, 8) to communicate current health status information, and/or 9) to detect an impact.

SUMMARY OF THE INVENTION

The present invention features devices and methods for the minimization of hemorrhage caused by impact with an object. In particular, the invention features devices and methods for controlling bleeding from severed or damaged peripheral blood vessels. The methods and devices may be used to stabilize a patient (e.g., for transport or in cases where medical attention cannot be provided immediately). The methods and devices can be used to stabilize a patient by, e.g., controlling bleeding from a damaged vessel and/or by providing stabilization of a broken or fractured bone. Also, the methods and devices may be used to assist in increasing perfusion pressure to the heart and brain in a number of disease states, such as hemorrhagic shock, cardiogenic shock, and cardiac arrest.

Accordingly, in a first aspect, the invention features an impact detection device. This device includes:

(a) one or more (e.g., two or more, three or more, four or more, five or more, ten or more, twenty or more, fifty or more, or one hundred or more) impact detection sensors capable of detecting an impact;

(b) two or more bladders (e.g., three or more, four or more, five or more, ten or more, twenty or more, fifty or more, or one hundred or more), each of which include an aperture providing communication from the interior of the bladder to the exterior of the bladder and a valve controlling gas flow through the aperture and into the bladder(s);

(c) an inflation system including (i) an air pump or (ii) a cartridge including a gas or gas-generating agent, in which the air pump or cartridge is connected to the two or more bladders by a first tube network which is connected to each valve; and (d) a triggering mechanism for activating the inflation system in response to a signal from the one or more impact detection sensors and causing the bladders to inflate.

In some embodiments, the impact detection sensor detects the impact by detecting a change in pressure or conductivity. In other embodiments, the impact detection sensor is a piezoelectric system (e.g., a piezoelectric film), a network of fluid-carrying tubes, and/or a conductive material (e.g., a network of conductive mesh or layers of material with different conductivity levels).

In certain embodiments, the first tube network includes one or more tubes (e.g., two or more, three or more, four or more, five or more, six or more, seven or more, eight or more, nine or more, ten or more, fifteen or more, twenty or more, thirty or more, fifty or more, one hundred or more) that connect each of the bladders of the inflation system to the air pump or cartridge.

In some embodiments, the device includes two bladders.

In other embodiments, the device includes more than two bladders (e.g., more than three, more than four, more than five, more than ten, more than twenty, more than thirty, more than fifty).

In certain embodiments, the gas is pressurized (e.g., carbon dioxide, nitrogen, oxygen, hydrogen, or other non-flammable and/or inert gas).

In other embodiments, when activated by the triggering mechanism, one or more (e.g., two or more, three or more, four or more, five or more, ten or more, twenty or more, fifty or more) of the bladders are inflated by the pressurized gas.

In certain embodiments, the cartridge of the inflation system includes the gas-generating agent (e.g., an alkali metal chlorate, an alkali metal perchlorate, a peroxide, or a superoxide).

In some embodiments, when activated by the triggering mechanism, one or more (e.g., two or more, three or more, four or more, five or more, ten or more, twenty or more, fifty or more) of the bladders are inflated by gas (e.g., carbon dioxide, nitrogen, oxygen, hydrogen, or other non-flammable and/or inert gas) evolved by the gas-generating agent.

In other embodiments, the first tube network further includes an aperture and a valve (e.g., a valve which allows for about 2-10 psi of gas flow) controlling gas flow through the aperture and into the bladder(s).

In certain embodiments, the aperture and valve are configured for manual inflation of one or more (e.g., two or more, three or more, four or more, five or more, ten or more, twenty or more, fifty or more) of the bladders.

In some embodiments, the triggering mechanism is configured to activate the inflation system in response to a manual signal, thereby causing the bladders to inflate (e.g., to a pressure of between about 2-10 psi, such as, e.g., about 4.5 psi).

In other embodiments, the triggering mechanism and the one or more impact detection sensors are connected by leads (e.g., wire, conductive thread, or metal pad).

In certain embodiments, the triggering mechanism and the one or more impact detection sensors are connected by a wireless signal.

In some embodiments, the triggering mechanism and the inflation system are connected by leads (e.g., wire, conductive thread, or metal pad).

In other embodiments, the triggering mechanism and the inflation system are connected by a wireless signal.

In certain embodiments, any of the foregoing devices further include:

(e) one or more (e.g., two or more, three or more, four or more, five or more, ten or more, twenty or more, fifty or more) information processing units connected to the one or more impact detection sensors, the information processing units being programmed to activate the device upon identification of an impact type.

In some embodiments, the information processing unit is programmed to activate upon identification (e.g., by the one or more impact detection sensors) of an impact that results in a hemorrhage.

In other embodiments, the information processing unit is further programmed to determine the location of the impact.

In certain embodiments, any of the foregoing devices further include:

(f) an amplifier (e.g., to amplify the signal generated by the impact detection sensors) connected to the impact detection system by leads (e.g., wire, conductive thread, or metal pad); and/or (g) a controller connected to the amplifier, the controller including an analog to digital converter and a compare circuit; and/or (h) a programmable memory system (e.g., non-transitory read-only memory system) connected to the controller, the memory system including parameters in terms of signal amplitude of different impact types, and/or a data storage system (e.g., a flash memory based system) to record data from sensor inputs.

In some embodiments, any of the foregoing devices further include (i) a sealant system including a container having one or more (e.g., two or more, three or more, four or more, five or more, ten or more, twenty or more, fifty or more) enclosed compartments including a sealant.

In other embodiments, any of the foregoing devices further include (j) a triggering mechanism for activating the sealant system in response to a signal from the one or more impact detection sensors and causing release of the sealant.

In certain embodiments, the triggering mechanism for activating the sealant system and the triggering mechanism for activating the inflation system are the same.

In some embodiments, the triggering mechanism for activating the sealant system and the triggering mechanism for activating the inflation system are different.

In other embodiments, the sealant is released proximal to, or at the site of, the impact.

In certain embodiments, the triggering mechanism activates the sealant system prior to, subsequent to, or concurrently with the inflation system.

In some embodiments, the triggering mechanism for activating the sealant system and the sealant system are connected by leads (e.g., wire, conductive thread, or metal pad) or a wireless signal.

In certain embodiments, the sealant is a wound sealant (e.g., a biopolymer, a synthetic polymer, a biosynthetic composite, or a mixture thereof). In some embodiments, the wound sealant is one or more (e.g., two or more, three or more, four or more, five or more, six or more, seven or more, eight or more, nine or more, ten or more) of the wound sealants shown in Table 1.

In other embodiments, the container further includes a frangible seal. In certain embodiments, upon the activation by the triggering mechanism, or upon the impact to the device, breakage of the frangible seal releases the sealant.

In some embodiments, the one or more compartments further include one or more (e.g., two or more, three or more, four or more, five or more, ten or more, twenty or more, fifty or more) apertures communicating from the interior of the compartment to the exterior of the compartment and one or more (e.g., two or more, three or more, four or more, five or more, ten or more, twenty or more, fifty or more) valves controlling fluid flow through the apertures.

In other embodiments, the one or more compartments are connected to an air pump or cartridge including gas or a gas-generating agent, in which the air pump or cartridge is connected to the one or more compartments by a second tube network which is connected to the one or more valves of the one or more compartments.

In certain embodiments, the gas is pressurized (e.g., carbon dioxide, nitrogen, oxygen, or hydrogen, or other non-flammable and/or inert gas).

In some embodiments, the cartridge includes the gas-generating agent (e.g., an alkali metal chlorate, an alkali metal perchlorate, a peroxide, or a superoxide) that can generate a gas (e.g., carbon dioxide, nitrogen, oxygen, or hydrogen, or other non-flammable and/or inert gas).

In other embodiments, the device includes a first layer including the one or more impact detection sensors and a second layer including the inflation system.

In certain embodiments, the device further includes a third layer including the sealant system.

In some embodiments, the first layer further includes the sealant system.

In other embodiments, the second layer further includes the sealant system.

In certain embodiments, any of the foregoing devices further include (k) an energy source (e.g., to provide power to the impact detection sensors, a triggering mechanism, the inflation system, the information processing unit, amplifier, controller, memory system, sealant system, and/or other sensors). The energy source can provide power to the device for one or more days (e.g., 1-10 days or more) when in an inactive or monitoring state (e.g., the unit is turned off or in hover or record mode) or for one or more hours (e.g., 1-10 hours or more) when in an active state (e.g., auto action mode, manual action mode, or maintenance mode).

In some embodiments, the energy source includes a battery powered power supply (e.g., a rechargeable battery powered energy supply).

In other embodiments, any of the foregoing devices further include (l) a GPS unit (e.g., to identify the position of the device). In certain embodiments, the GPS unit is activated in response to a signal from the one or more impact detection sensors or a manual signal. In some embodiments, the GPS unit and the one or more impact detection sensors are connected by leads (e.g., wire, conductive thread, or metal pad). In other embodiments, the GPS unit and the one or more impact detection sensors are connected by a wireless signal.

In certain embodiments, any of the foregoing devices further includes (m) a data transmitter (e.g., to transmit data from one or more sensors). In some embodiments, the data transmitter is activated in response to a signal from the one or more impact detection sensors. In other embodiments, upon the activation, the data transmitter transmits (e.g., to rescue personnel) status and/or identity information (e.g., about the object or individual wearing the device). In certain embodiments, the data transmitter and the one or more impact detection sensors are connected by leads (e.g., wire, conductive thread, or metal pad). In some embodiments, the data transmitter and the one or more impact detection sensors are connected by a wireless signal. In some embodiments, the data transmitter transmits data to a visual readout, such as a monitor (e.g., a computer monitor), a handheld device (e.g., a smartphone), or other visual display.

In other embodiments, the device is configured for use by a mammal (e.g., a human or dog). In some embodiments, the device is configured as an article of clothing (e.g., as headgear, a vest, a jacket, pants, or a full body suit, e.g., as shown in FIGS. 1A-1E). In certain embodiments, the device is configured for use with an inanimate object (e.g., an object filled with gas or an object filled with liquid).

In another aspect, the invention features a method of minimizing hemorrhage from an object or individual caused by an impact. This method includes inflating one or more (e.g., two or more, three or more, four or more, five or more, ten or more, twenty or more, fifty or more) of the bladders of any of the foregoing devices in response to the impact, whereby inflation of the bladders at the site of the impact minimizes the hemorrhage by applying pressure at the impact site.

In some embodiments, the method further includes affixing the device to the object or individual prior to the impact. In other embodiments, the method further includes affixing the device to the object or individual after the impact.

In certain embodiments, any of the foregoing methods further include generating a signal by the impact detection system in response to the impact. In some embodiments, the signal activates the triggering mechanism for activating the inflation system, thereby inflating one or more (e.g., two or more, three or more, four or more, five or more, ten or more, twenty or more, fifty or more) of the bladders. In other embodiments, any of the foregoing methods further include releasing sealant at the hemorrhage site.

In certain embodiments, the impact is a puncture or a penetration injury. In some embodiments, the hemorrhage is a loss of liquid (e.g., a loss of blood or oil) or gas.

In other embodiments, the device is configured to be worn by an individual, which may be a mammal (e.g., a human or a dog).

In certain embodiments, the impact is caused by a bullet, a knife, a bomb, shrapnel, a blunt force, or an animal bite. In some embodiments, the impact site is an arm, a leg, the torso, the hips, the shoulders, the head, or the neck.

In other embodiments, the device is configured for use with an inanimate object (e.g., an inflatable raft, a canister, a barrel, a vehicle, or a boat). In some embodiments, the inanimate object is filled with a liquid or a gas.

In another aspect, the invention features a method for restricting movement in a mammal (e.g., a human or a dog) injured by an impact including inflating one or more (e.g., two or more, three or more, four or more, five or more, ten or more, twenty or more, fifty or more) of the bladders of any of the foregoing devices, whereby inflation of the one or more bladders restricts the movement of the mammal and/or stabilizes the mammal.

In some embodiments, inflation of one or more (e.g., two or more, three or more, four or more, five or more, ten or more, twenty or more, fifty or more) of the bladders occurs in response to a manual signal. In other embodiments, any of the foregoing methods further include inflating one or more (e.g., two or more, three or more, four or more, five or more, ten or more, twenty or more, fifty or more) of the bladders at one or more (e.g., two or more, three or more, four or more, five or more, ten or more, twenty or more, fifty or more) non-impact sites.

In certain embodiments, the non-impact site is an arm, a leg, the torso, the hips, the shoulders, the head, or the neck.

In some embodiments, one or more (e.g., two or more, three or more, four or more, five or more, ten or more, twenty or more, fifty or more) of the bladders inflate at a single non-impact site. In other embodiments, one or more (e.g., two or more, three or more, four or more, five or more, ten or more, twenty or more, fifty or more) of the bladders inflate at a plurality of non-impact sites.

In another aspect, the invention features a method of minimizing hemorrhage from an object or individual. This method includes:

i) affixing a device including (b) two or more (e.g., three or more, four or more, five or more, ten or more, twenty or more, fifty or more) bladders to the object or individual; and ii) inflating one or more (e.g., two or more, three or more, four or more, five or more, ten or more, twenty or more, fifty or more) of the bladders in response to an impact, wherein the bladders are capable of applying pressure at an impact site, thereby minimizing hemorrhage from the object or individual.

In some embodiments, the device further includes: (a) one or more (e.g., two or more, three or more, four or more, five or more, ten or more, twenty or more, fifty or more) impact detection sensors capable of detecting the impact.

In other embodiments, the bladders include an aperture providing communication from the interior of the bladder to the exterior of the bladder and a valve (e.g., a valve which allows for about 2-10 psi of gas flow) controlling gas flow through the aperture and into the bladder(s).

In certain embodiments, the device further includes: (c) an inflation system including an air pump or cartridge including gas or a gas-generating agent, in which the air pump or cartridge is connected to the two or more bladders by a first tube network which is connected to each valve.

In some embodiments, the device further includes: (d) a triggering mechanism for activating the inflation system in response to a signal from the one or more impact detection sensors and causing the bladders to inflate.

In some embodiments, the method further includes generating a signal in response to the impact, in which the signal is generated by the impact detection system.

In other embodiments, the method further includes activating the triggering mechanism, in which the activating results in the inflation of one or more (e.g., two or more, three or more, four or more, five or more, ten or more, twenty or more, fifty or more) of the bladders.

In certain embodiments, the impact detection sensor detects the impact by detecting a change in pressure or conductivity. In some embodiments, the impact detection sensor is a piezoelectric system (e.g., piezoelectric film), a network of fluid-carrying tubes, and/or a conductive material (e.g., a network of conductive mesh or layers of material with different conductivity levels).

In other embodiments, the first tube network includes one or more (e.g., two or more, three or more, four or more, five or more, six or more, seven or more, eight or more, nine or more, ten or more, fifteen or more, twenty or more, thirty or more, fifty or more, one hundred or more) tubes that connect each of the bladders of the inflation system to the air pump or cartridge.

In certain embodiments, the first tube network includes one or more tubes (e.g., two or more, three or more, four or more, five or more, six or more, seven or more, eight or more, nine or more, ten or more, fifteen or more, twenty or more, thirty or more, fifty or more, one hundred or more).

In some embodiments, the device includes two bladders.

In other embodiments, the device includes more than two bladders (e.g., more than three, more than four, more than five, more than ten, more than twenty, more than thirty, more than fifty).

In certain embodiments, the gas is pressurized (e.g., carbon dioxide, nitrogen, oxygen, hydrogen, or other non-flammable and/or inert gas). In other embodiments, when activated by the triggering mechanism, one or more of the bladders are inflated by the pressurized gas.

In certain embodiments, the cartridge of the inflation system includes the gas-generating agent (e.g., an alkali metal chlorate, an alkali metal perchlorate, a peroxide, or a superoxide). In some embodiments, when activated by the triggering mechanism, one or more (e.g., two or more, three or more, four or more, five or more, ten or more, twenty or more, fifty or more) of the bladders are inflated by gas (e.g., carbon dioxide, nitrogen, oxygen, hydrogen, or other non-flammable and/or inert gas) evolved by the gas-generating agent.

In other embodiments, the first tube network further includes an aperture and a valve (e.g., a valve which allows for about 2-10 psi of gas flow) controlling gas flow through the aperture and into the bladder(s).

In certain embodiments, the aperture and valve are configured for manual inflation of one or more (e.g., two or more, three or more, four or more, five or more, ten or more, twenty or more, fifty or more) of the bladders.

In some embodiments, the triggering mechanism is configured to activate the inflation system in response to a manual signal, thereby causing the bladders to inflate (e.g., to a pressure of between about 2-10 psi, such as about 4.5 psi).

In other embodiments, the triggering mechanism and the one or more impact detection sensors are connected by leads (e.g., wire, conductive thread, or metal pad).

In certain embodiments, the triggering mechanism and the one or more impact detection sensors are connected by a wireless signal.

In some embodiments, the triggering mechanism and the inflation system are connected by leads (e.g., wire, conductive thread, or metal pad).

In other embodiments, the triggering mechanism and the inflation system are connected by a wireless signal.

In certain embodiments, the device further includes:

(e) one or more (e.g., two or more, three or more, four or more, five or more, ten or more, twenty or more, fifty or more) information processing units connected to the one or more impact detection sensors, the information processing units being programmed to activate the device upon identification of an impact type.

In some embodiments, the information processing unit is programmed to activate upon identification of an impact that results in a hemorrhage.

In other embodiments, the information processing unit is further programmed to determine the location of the impact.

In certain embodiments, the device further includes:

(f) an amplifier (e.g., to amplify the signal generated by the impact detection sensors) connected to the impact detection system by leads (e.g., wire, conductive thread, or metal pad); and/or (g) a controller connected to the amplifier, the controller including an analog to digital converter and a compare circuit; and/or (h) a programmable non-transitory read-only memory system connected to the controller, the memory system including parameters in terms of signal amplitude of different impact types, and/or a data storage system (e.g., a flash memory based system) to record data from sensor inputs.

In some embodiments, the device further includes (i) a sealant system including a container having one or more (e.g., two or more, three or more, four or more, five or more, ten or more, twenty or more, fifty or more) enclosed compartments including a sealant.

In other embodiments, the device further includes (j) a triggering mechanism for activating the sealant system in response to a signal from the one or more impact detection sensors and causing release of the sealant.

In certain embodiments, the triggering mechanism for activating the sealant system and the triggering mechanism for activating the inflation system are the same. In some embodiments, the triggering mechanism for activating the sealant system and the triggering mechanism for activating the inflation system are different.

In other embodiments, the sealant is released proximal to, or at the site of, the impact.

In certain embodiments, the triggering mechanism activates the sealant system prior to, subsequent to, or concurrently with the inflation system.

In some embodiments, the triggering mechanism for activating the sealant system and the sealant system are connected by leads (e.g., wire, conductive thread, or metal pad).

In other embodiments, the triggering mechanism for activating the sealant system and the sealant system are connected by a wireless signal.

In certain embodiments, the sealant is a wound sealant (e.g., a biopolymer, a synthetic polymer, a biosynthetic composite, or a mixture thereof). In some embodiments, the wound sealant is one or more (two or more, three or more, four or more, five or more, six or more, seven or more, eight or more, nine or more, ten or more) of the wound sealants shown in Table 1.

In other embodiments, the container further includes a frangible seal. In certain embodiments, upon the activation by the triggering mechanism, or upon the impact to the device, breakage of the frangible seal releases the sealant.

In some embodiments, the one or more sealant-containing compartments further include one or more (e.g., two or more, three or more, four or more, five or more, ten or more, twenty or more, fifty or more) apertures communicating from the interior of the compartment to the exterior of the compartment and one or more (e.g., two or more, three or more, four or more, five or more, ten or more, twenty or more, fifty or more) valves controlling fluid flow through the apertures and out of the compartments.

In other embodiments, the one or more sealant-containing compartments are connected to an air pump or cartridge including gas or gas-generating agent, in which the air pump or cartridge is connected to the one or more compartments by a second tube network which is connected to the one or more valves of the one or more compartments.

In certain embodiments, the gas is pressurized (e.g., carbon dioxide, nitrogen, oxygen, or hydrogen, or other non-flammable and/or inert gas). In some embodiments, the cartridge includes the gas-generating agent (e.g., an alkali metal chlorate, an alkali metal perchlorate, a peroxide, or a superoxide).

In other embodiments, the device includes a first layer including the one or more impact detection sensors and a second layer including the inflation system. In certain embodiments, the device further includes a third layer including the sealant system. In some embodiments, the first layer further includes the sealant system. In other embodiments, the second layer further includes the sealant system.

In certain embodiments, the device further includes (k) an energy source (e.g., to provide power to the impact detection sensors, a triggering mechanism, the inflation system, the information processing unit, amplifier, controller, memory system, sealant system, and/or other sensors). The energy source can provide power to the device for one or more days (e.g., 1-10 days or more) when in an inactive or monitoring state (e.g., the unit is turned off or in hover or record mode) or for one or more hours (e.g., 1-10 hours or more) when in an active state (e.g., auto action mode, manual action mode, or maintenance mode).

In some embodiments, the energy source includes a battery powered power supply (e.g., a rechargeable battery powered power supply).

In other embodiments, the device further includes (l) a GPS unit (e.g., to provide the location of the device). In certain embodiments, the GPS unit is activated in response to a signal from the one or more impact detection sensors. In some embodiments, the GPS unit and the one or more impact detection sensors are connected by leads (e.g., wire, conductive thread, or metal pad). In other embodiments, the GPS unit and the one or more impact detection sensors are connected by a wireless signal.

In certain embodiments, the device further includes (m) a data transmitter (e.g., to transmit data from one or more sensors). In some embodiments, the data transmitter is activated in response to a signal from the one or more impact detection sensors. In other embodiments, upon the activation, the data transmitter transmits status (e.g., to rescue personnel) and/or identity information (e.g., information about the object or individual wearing the device). In certain embodiments, the data transmitter and the one or more impact detection sensors are connected by leads (e.g., wire, conductive thread, or metal pad). In some embodiments, the data transmitter and the one or more impact detection sensors are connected by a wireless signal.

In other embodiments, the device is configured for use by a mammal (e.g., a human or dog). In some embodiments, the device is configured as an article of clothing (e.g., headgear, a vest, a jacket, pants, or a full body suit).

In certain embodiments, the device is configured for use with an inanimate object (e.g., an object filled with gas or an object filled with liquid).

In certain embodiments, the device includes a valve system, or a component for creating a vacuum (e.g., a vacuum pump), that is configured to deflate one or more of the two or more bladders (e.g., to allow for oscillation (repeated filling and deflating, e.g., in random order, in an ordered sequence, or substantially simultaneously) of the bladders).

In another aspect, the invention features a device configured as a jacket, vest, or pants for use by a human and comprising:

(a) one or more impact detection sensors capable of detecting an impact;

(b) two or more bladders, each of the bladders comprising an aperture providing communication from the interior of the bladder to the exterior of the bladder and a valve controlling gas flow through the aperture;

(c) an inflation system comprising an air pump or cartridge comprising a gas or gas-generating agent, in which the air pump or cartridge is connected to said two or more bladders by a first tube network which is connected to each of the valve(s); and (d) a triggering mechanism for activating said inflation system in response to a signal from the one or more of the impact detection sensors and causing the bladders to inflate, in which the triggering mechanism is configured to activate the inflation system in response to a manual signal, thereby causing the bladders to inflate;

(e) an information processing unit connected to one or more of the impact detection sensors, the information processing unit being programmed to activate the device upon identification of an impact type, in which the information processing unit is further programmed to determine the location of the impact;

(i) a sealant system comprising a container having one or more enclosed compartments comprising a sealant;

(j) a triggering mechanism for activating the sealant system in response to a signal from one or more of the impact detection sensors and, when activated, causing release of the sealant, in which the sealant is released proximal to, or at the site of, the impact;

(k) an energy source (e.g., to provide power for the impact detection sensors, inflation system, a triggering mechanism, the information processing unit, the sealant system, the data transmitter, and/or one or more other sensors);

(l) a GPS unit, wherein the GPS unit is activated in response to a signal from one or more of the impact detection sensors; and (m) a data transmitter, in which the data transmitter is configured to be activated in response to a signal from one or more of the impact detection sensors and, upon activation, the data transmitter transmits status and/or identity information.

In other embodiments, the device further includes one or more of the following:

(f) an amplifier (e.g., to amplify the signal generated by the impact detection sensors) connected to the impact detection system by leads (e.g., wire, conductive thread, or metal pad); and/or (g) a controller connected to the amplifier, the controller including an analog to digital converter and a compare circuit; and/or (h) a programmable non-transitory read-only memory system connected to the controller, the memory system including parameters in terms of signal amplitude of different impact types, and/or a data storage system (e.g., a flash memory based system) to record data from sensor inputs.

In another aspect, the invention features a device configured as a full body suit for use by a human and comprising:

(a) one or more impact detection sensors capable of detecting an impact;

(b) two or more bladders, each of the bladders including an aperture providing communication from the interior of the bladder to the exterior of the bladder and a valve controlling gas flow through the aperture;

(c) an inflation system comprising an air pump or cartridge comprising a gas or gas-generating agent, wherein the air pump or cartridge is connected to the two or more bladders by a first tube network which is connected to each valve; and (d) a triggering mechanism for activating the inflation system in response to a signal from one or more of the impact detection sensors and causing the bladders to inflate, in which the triggering mechanism is configured to activate the inflation system in response to a manual signal, thereby causing said bladders to inflate.

In some embodiments, the device further includes one or more of the following:

(i) a sealant system comprising a container having one or more enclosed compartments comprising a sealant;

(j) a triggering mechanism for activating the sealant system in response to a signal from one or more of the impact detection sensors and, when activated, causing release of the sealant, in which the sealant is released proximal to, or at the site of, the impact;

(k) an energy source (e.g., to provide power for the impact detection sensors, inflation system, a triggering mechanism, the information processing unit, the sealant system, the data transmitter, and/or one or more other sensors);

(l) a GPS unit, in which the GPS unit is configured to be activated in response to a signal from one or more of the impact detection sensors; and (m) a data transmitter, in which the data transmitter is configured to be activated in response to a signal from one or more of the impact detection sensors and, upon activation, the data transmitter transmits status and/or identity information.

In other embodiments, the device further includes one or more of the following:

(e) an information processing unit connected to one or more of the impact detection sensors, the information processing unit being programmed to activate the device upon identification of an impact type, in which the information processing unit is further programmed to determine the location of the impact;

(f) an amplifier (e.g., to amplify the signal generated by the impact detection sensors) connected to the impact detection system by leads (e.g., wire, conductive thread, or metal pad); and/or (g) a controller connected to the amplifier, the controller including an analog to digital converter and a compare circuit; and/or (h) a programmable non-transitory read-only memory system connected to the controller, the memory system including parameters in terms of signal amplitude of different impact types, and/or a data storage system (e.g., a flash memory based system) to record data from sensor inputs.

In another aspect, the invention features a device configured for use with an object filled with gas (e.g., an inflatable boat) and comprising:

(a) one or more impact detection sensors capable of detecting an impact;

(b) two or more bladders, each of the bladders comprising an aperture providing communication from the interior of the bladder to the exterior of the bladder and a valve controlling gas flow through the aperture;

(c) an inflation system comprising an air pump or cartridge comprising a gas or gas-generating agent, in which the air pump or cartridge is connected to the two or more bladders by a first tube network which is connected to each valve; and (d) a triggering mechanism for activating the inflation system in response to a signal from one or more of the impact detection sensors and causing the bladders to inflate, in which the triggering mechanism is configured to activate the inflation system in response to a manual signal, thereby causing the bladders to inflate;

(i) a sealant system including a container having one or more enclosed compartments comprising a sealant;

(j) a triggering mechanism for activating the sealant system in response to a signal from one or more of the impact detection sensors and, when activated, causing release of the sealant, in which the sealant is released proximal to, or at the site of, said impact;

(k) an energy source; and (l) a GPS unit, wherein said GPS unit is activated in response to a signal from one or more of the impact detection sensors.

In other embodiments, the device further includes one or more of the following:

(e) an information processing unit connected to one or more of the impact detection sensors, the information processing unit being programmed to activate the device upon identification of an impact type, in which the information processing unit is further programmed to determine the location of the impact;

(f) an amplifier (e.g., to amplify the signal generated by the impact detection sensors) connected to the impact detection system by leads (e.g., wire, conductive thread, or metal pad); and/or (g) a controller connected to the amplifier, the controller including an analog to digital converter and a compare circuit; and/or (h) a programmable non-transitory read-only memory system connected to the controller, the memory system including parameters in terms of signal amplitude of different impact types, and/or a data storage system (e.g., a flash memory based system) to record data from sensor inputs.

In some embodiments, the device further includes the following:

(m) a data transmitter, in which the data transmitter is configured to be activated in response to a signal from one or more of the impact detection sensors and, upon activation, the data transmitter transmits status and/or identity information.

In another aspect, the invention features a device configured for use with an object filled with liquid (e.g., an oil tank) and comprising:

(a) one or more impact detection sensors capable of detecting an impact;

(b) two or more bladders, each of the bladders comprising an aperture providing communication from the interior of the bladder to the exterior of the bladder and a valve controlling gas flow through the aperture;

(c) an inflation system including an air pump or cartridge comprising a gas or gas-generating agent, in which the air pump or cartridge is connected to the two or more bladders by a first tube network which is connected to each valve; and (d) a triggering mechanism for activating the inflation system in response to a signal from one or more of the impact detection sensors and causing said bladders to inflate, in which the triggering mechanism is configured to activate the inflation system in response to a manual signal, thereby causing the bladders to inflate; and (i) a sealant system including a container having one or more enclosed compartments comprising a sealant; and (j) a triggering mechanism for activating the sealant system in response to a signal from one or more of the impact detection sensors and, when activated, causing release of the sealant, in which the sealant is released proximal to, or at the site of, said impact.

In some embodiments, the device further includes one or more of the following:

(k) an energy source (e.g., to provide power for the impact detection sensors, inflation system, a triggering mechanism, the information processing unit, the sealant system, the data transmitter, and/or one or more other sensors);

(l) a GPS unit, in which the GPS unit is configured to be activated in response to a signal from one or more of the impact detection sensors; and (m) a data transmitter, in which the data transmitter is configured to be activated in response to a signal from one or more of the impact detection sensors and, upon activation, the data transmitter transmits status and/or identity information.

In other embodiments, the device further includes one or more of the following:

(e) an information processing unit connected to one or more of the impact detection sensors, the information processing unit being programmed to activate the device upon identification of an impact type, in which the information processing unit is further programmed to determine the location of the impact;

(f) an amplifier (e.g., to amplify the signal generated by the impact detection sensors) connected to the impact detection system by leads (e.g., wire, conductive thread, or metal pad); and/or (g) a controller connected to the amplifier, the controller including an analog to digital converter and a compare circuit; and/or (h) a programmable non-transitory read-only memory system connected to the controller, the memory system including parameters in terms of signal amplitude of different impact types, and/or a data storage system (e.g., a flash memory based system) to record data from sensor inputs.

In another aspect, the invention features a device configured for use as an immersion survival suit for use by a human and comprising:

(a) one or more impact detection sensors capable of detecting an impact;

(b) two or more bladders, each of the bladders comprising an aperture providing communication from the interior of the bladder to the exterior of the bladder and a valve controlling gas flow through the aperture;

(c) an inflation system comprising an air pump or cartridge comprising a gas or gas-generating agent, in which the air pump or cartridge is connected to said two or more bladders by a first tube network which is connected to each of the valve(s); and (d) a triggering mechanism for activating the inflation system in response to a signal from the one or more of the impact detection sensors and, when activated, causing the bladders to inflate, in which the triggering mechanism is configured to activate the inflation system in response to a manual signal, thereby causing the bladders to inflate.

In some embodiments, the device is configured to create pressure (e.g., to create a water tight seal) around the neck or extremities (e.g., around the cuffs at the wrists or ankles). The pressure applied around the neck and/or extremities is less than 11 psi, 5 psi, 2 psi, 1 psi, or 0.5 psi.

In other embodiments, the device includes one or more of the following:

(e) an information processing unit connected to one or more of the impact detection sensors, the information processing unit being programmed to activate the device upon identification of an impact type, in which the information processing unit is further programmed to determine the location of the impact;

(i) a sealant system comprising a container having one or more enclosed compartments comprising a sealant;

(j) a triggering mechanism for activating the sealant system in response to a signal from one or more of the impact detection sensors and, when activated, causing release of the sealant, in which the sealant is released proximal to, or at the site of, the impact;

(k) an energy source (e.g., to provide power for the impact detection sensors, inflation system, a triggering mechanism, the information processing unit, the sealant system, the data transmitter, and/or one or more other sensors);

(l) a GPS unit, in which the GPS unit is configured to be activated in response to a signal from one or more of the impact detection sensors; and/or (m) a data transmitter, in which the data transmitter is configured to be activated in response to a signal from one or more of the impact detection sensors and, upon activation, the data transmitter transmits status and/or identity information.

In other embodiments, the device further includes one or more of the following:

(f) an amplifier (e.g., to amplify the signal generated by the impact detection sensors) connected to the impact detection system by leads (e.g., wire, conductive thread, or metal pad); and/or (g) a controller connected to the amplifier, the controller including an analog to digital converter and a compare circuit; and/or (h) a programmable non-transitory read-only memory system connected to the controller, the memory system including parameters in terms of signal amplitude of different impact types, and/or a data storage system (e.g., a flash memory based system) to record data from sensor inputs.

In another aspect, the invention features a device configured for use as a breast pump by a mammal (e.g., a human) and comprising:

(a) one or more impact detection sensors capable of detecting contact with breast tissue;

(b) two or more bladders (e.g., two to ten bladders), each of the bladders comprising an aperture providing communication from the interior of the bladder to the exterior of the bladder and a valve controlling gas flow through the aperture;

(c) an inflation system including an air pump or cartridge comprising a gas or gas-generating agent, in which the air pump or cartridge is connected to the two or more bladders by a first tube network which is connected to each valve; and (d) a triggering mechanism for activating the inflation system in response to a signal from one or more of the impact detection sensors and, when activated, causing the bladders to inflate, in which the triggering mechanism is configured to activate the inflation system in response to a manual signal or activation of the one or more impact detection sensors, thereby causing the bladders to inflate.

The breast pump device may have the form generally similar to that shown in FIG. 1F.

In other embodiments, the device further includes one or more of the following:

(e) an information processing unit connected to one or more of the impact detection sensors, the information processing unit being programmed to activate the device upon identification of an impact type, in which the information processing unit is further programmed to determine the location of the impact;

(f) an amplifier (e.g., to amplify the signal generated by the impact detection sensors) connected to the impact detection system by leads (e.g., wire, conductive thread, or metal pad); and/or (g) a controller connected to the amplifier, the controller including an analog to digital converter and a compare circuit; and/or (h) a programmable non-transitory read-only memory system connected to the controller, the memory system including parameters in terms of signal amplitude of different impact types, and/or a data storage system (e.g., a flash memory based system) to record data from sensor inputs.

In other embodiments, the device further includes one or more of the following:

(k) an energy source (e.g., to provide power for the impact detection sensors, inflation system, a triggering mechanism, the information processing unit, the sealant system, the data transmitter, and/or one or more other sensors); and/or (m) a data transmitter, in which the data transmitter is configured to be activated in response to a signal from one or more of the impact detection sensors and, upon activation, the data transmitter transmits status and/or identity information.

In some embodiments, the device may further include a vacuum (e.g., to assist in extracting breast milk from the breast tissue) and/or an external container (e.g., to collect breast milk). Breast pumps utilizing vacuums and external containers are well known in the art. Any known vacuum or external container may be used in connection with the device of the invention.

In other embodiments, the device includes a valve system, or a component for creating a vacuum (e.g., a vacuum pump), that is configured to deflate one or more of the two or more bladders (e.g., to allow for oscillation (repeated filling and deflating, e.g., in random order, in an ordered sequence, or substantially simultaneously) of the bladders during use of the breast pump).

In another aspect, the invention features a device configured for use as a blood pressure monitor for use by a human and comprising:

(a) one or more impact detection sensors capable of detecting physical contact with a body part (e.g., an arm) inserted into the device;

(b) two or more bladders (e.g., two to ten bladders), each of the bladders comprising an aperture providing communication from the interior of the bladder to the exterior of the bladder and a valve controlling gas flow through the aperture;

(c) an inflation system including an air pump or cartridge comprising a gas or gas-generating agent, in which the air pump or cartridge is connected to the two or more bladders by a first tube network which is connected to each valve;

(d) a triggering mechanism for activating the inflation system in response to a signal from one or more of the impact detection sensors and causing said bladders to inflate, in which the triggering mechanism is configured to activate the inflation system in response to a manual signal or activation of the one or more impact detection sensors, thereby causing said bladders to inflate;

(e) an information processing unit connected to one or more of the impact detection sensors, the information processing unit being programmed to activate the device upon identification of an impact type, in which the information processing unit is further programmed to determine blood pressure; and (m) a data transmitter, in which the data transmitter is configured to be activated in response to a signal from one or more of the impact detection sensors and, upon activation, the data transmitter transmits status, such as blood pressure information. In some embodiments, the data transmitter transmits data to a visual readout, such as a monitor (e.g., a computer monitor), a handheld device (e.g., a smartphone), or other visual display.

The data transmitter may receive information from a blood pressure sensor for detecting the blood pressure of the human. The blood pressure sensor may be a separate component of the device or it may be integrated with the information processing unit. If separate from the information processing unit, the blood pressure sensor may be configured to communicate information regarding the blood pressure status of the human to the information processing unit, which provides that information to the data transmitter. Alternatively, the blood pressure sensor may be configured to communicate information regarding the blood pressure status of the human directly to the data transmitter.

The device may take the form of a blood pressure cuff, e.g., one that is configured to fit around, e.g., an arm. The device may be configured to detect the blood pressure of the human, e.g., during and/or after inflation of the one or more bladders and/or while one or more (or all) of the bladders are deflating. The inflation system of the device may be configured to inflate the two or more bladders so as to apply a pressure of between 100-200 mm Hg (e.g., 150 mm Hg or less) to the arm of the human (e.g., around or near the brachial artery). The device may be configured to inflate to this pressure within about 10-60 seconds. The device may further include a valve system, or a component for creating a vacuum (e.g., a vacuum pump), that is configured to deflate one or more of the bladders during use of the blood pressure device (e.g., at a pressure of about 2-3 mm Hg per second). Alternatively, the bladders may be configured to deflate at a pressure of about 2-3 mm Hg per second once the inflation system is disengaged (e.g., after inflation to a pressure of between 100-200 mm Hg).

In some embodiments, the device further includes:

(k) an energy source (e.g., to provide power for the impact detection sensors, inflation system, a triggering mechanism, the information processing unit, the sealant system, the data transmitter, and/or one or more other sensors).

In other embodiments, the device further includes one or more of the following:

(f) an amplifier (e.g., to amplify the signal generated by the impact detection sensors) connected to the impact detection system by leads (e.g., wire, conductive thread, or metal pad); and/or (g) a controller connected to the amplifier, the controller including an analog to digital converter and a compare circuit; and/or (h) a programmable non-transitory read-only memory system connected to the controller, the memory system including parameters in terms of signal amplitude of different impact types, and/or a data storage system (e.g., a flash memory based system) to record data from sensor inputs.

In an embodiment of all aspects of the invention, the device is capable of maintaining the pressure of one or more of the bladders for a period of time (e.g., 1-10 hours or more, such as 1, 2, 3, 4, or 5 hours).

Other features and advantages of the invention will be apparent from the following Detailed Description, the drawings, and the claims.

BRIEF DESCRIPTION OF THE DRAWINGS

FIGS. 1A-1E are illustrations showing devices of the invention. FIG. 1A shows a device of the invention configured as clothing integrated into tactical gear. FIG. 1B shows a device of the invention configured as a suit. FIG. 1C shows a device of the invention configured as a vest. FIG. 1D shows a device of the invention configured as a wound dressing. FIG. 1E is a schematic showing a top cut-away view of a suit that includes a device (32) of the invention that is worn underneath a conventional military outfit by a military person, who is shown lying on the ground. FIG. 1F shows a device of the invention configured as a breast pump.

FIG. 4A is an illustration showing a device of the invention integrated into a diver's wetsuit after an injury and before activation, while

FIG. 8A is a cross-section view of the system of FIG. 7.

FIG. 21A is a side view of the device. FIG. 21B shows three cut-away views of the device of FIG. 21A. FIG. 21C is a cut-away view of the device of FIG. 21A showing the internal components: pressurized medium container 98, energy source 96, central unit 74 (including a transmitter for wireless data transmission and communication), main valve system (e.g., a solenoid) 89, pressure sensitive conductive fabric 91, piezo-electric impact detection layer 90, and micro-inflatable compression layer (including a bladder network) 99.

FIGS. 22A-22H are photographs depicting a model applying a device of the invention. FIG. 22A is a front view prior to application of the device around the waist. FIG. 22B is a front view of the device being held by the model. FIG. 22C is a front view showing the model placing the device around their waist. FIG. 22D is a front view showing the device being secured to the model. FIG. 22E is a front view showing the device in place. FIG. 22F is a left side view of the model wearing the device. FIG. 22G is a back view of the model wearing the device. FIG. 22H is a right side view of the model wearing the device.

FIG. 23A is a photograph showing the device prior to placement. FIG. 23B is a photograph showing placement of the device on a box filled with water (representing a wearer of the device). FIG. 23C is a photograph of a gun used to shoot a bullet through the device and into the box. FIG. 23D is a photograph showing the experimental setup for testing the device capabilities. Also depicted is a signal wirelessly being transferred to a handheld device (e.g., a smart phone or tablet), which provides updates on the status of the device and "wearer."

FIG. 24A shows the device prior to impact with a bullet. FIG. 24B shows the device 0 seconds after impact. FIG. 24C shows the device 1 second after impact.

FIG. 24D shows the device 25 seconds after impact. FIG. 24E is a photograph showing the size of the impact produced after impact with a bullet.

DETAILED DESCRIPTION

Figure 2:
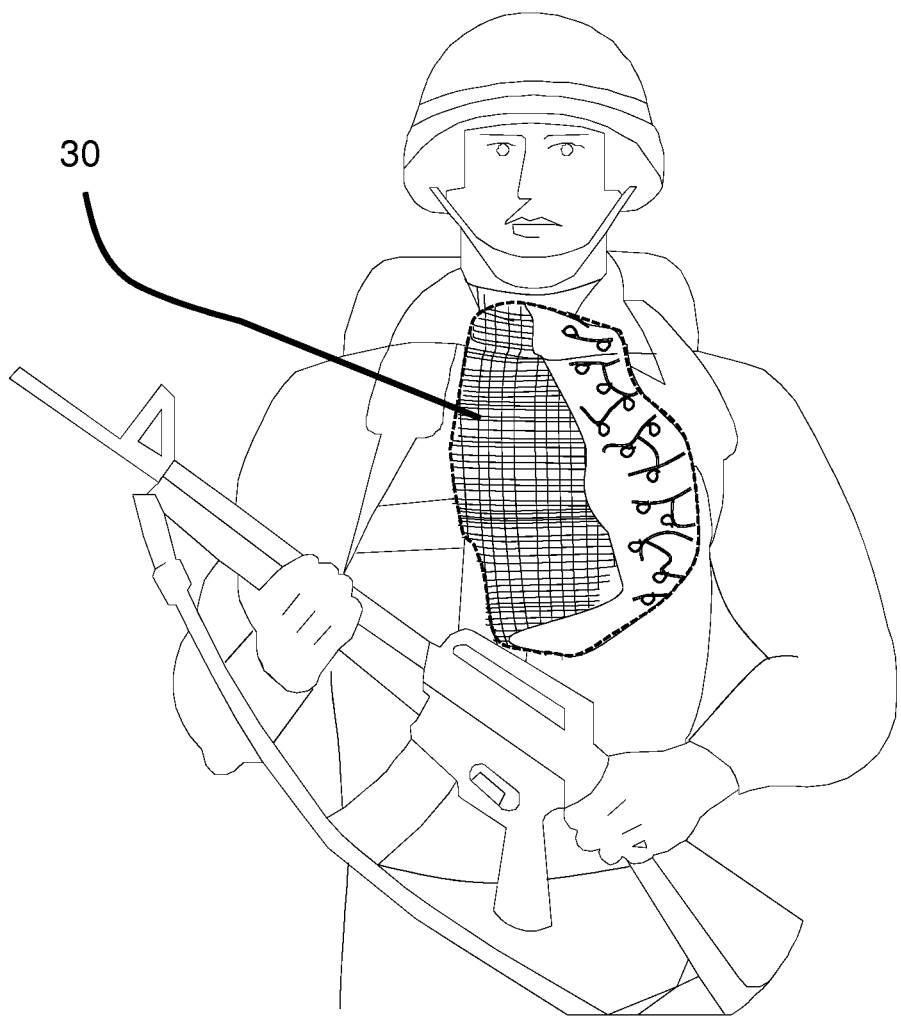
FIG. 2 is a schematic showing a front cut-away view of a device of the invention as a jacket (30) worn by a military person underneath conventional clothing.

The invention features a device that can be worn by an individual (e.g., a mammal, such as a human or a dog), devices for use with objects, e.g., inflatable objects, and devices for use with machines. In some embodiments, the device includes a networked layer of interconnected bladders that can be individually (or in groups) inflated and deflated. An additional pressure sensitive layer senses impacts to the device or penetration of objects through the device, which may pass into the body of the wearer or object, and triggers automatically the inflation of the bladders to seal off the site of penetration and maintains pressure on the site, e.g., until attention can be given to the wearer (e.g., emergency care) or object. The inflation of the device may also be triggered manually.

The invention also generally relates to methods and devices for controlling bleeding from severed or damaged peripheral blood vessels. The methods and devices may be used to stabilize the patient (e.g., for transport or in cases where medical attention cannot be provided immediately). The methods and devices can be used to stabilize the patient by, e.g., controlling bleeding from a damaged vessel and/or by providing stabilization of a broken or fractured bone. Also, the methods and devices may be used to assist in increasing perfusion pressure to the heart and brain in a number of disease states, such as hemorrhagic shock, cardiogenic shock, and cardiac arrest.

The devices of the invention may also be configured as a wearable garment (e.g., a vest, pants, sleeve, wrap, full-body suit, sock, helmet, glove, or brace). They may also provide an automated emergency treatment for controlling hemorrhage in places where compression is needed but where a tourniquet is not desired or cannot be used or where control by manual compression may be difficult. The device can be configured to act as a tourniquet, e.g., if a limb is severely wounded or lost (e.g., due to a bomb or other blast). Alternatively, or in addition, the devices of the invention may provide an automated stabilization system that can be used to stabilize all or a portion of the body (e.g., by restricting movement (e.g., for transportation purposes or when medical attention may be delayed), such as in the case of a broken or fractured bone). Alternatively, or in addition, the devices of the invention may provide buoyancy, for example, if used in a diving suit to keep an unconscious user afloat.

The devices of the invention may also include variants that can be used for sealing (e.g., to prevent or reduce leakage of fluids) and/or stabilizing damaged parts of a machine (e.g., a vehicle, such as a car or boat, and in particular the outer shell of a vehicle). Such devices may operate by repairing or stabilizing a damaged machine by, e.g., applying pressure to the damaged area and/or a sealant.

Before explaining in detail the present invention, it is to be understood that the invention is not limited in its application to the details of construction and arrangement of parts illustrated in the accompanying description and drawings since the invention is capable of other embodiments or arrangement and of being practiced or carried out in various ways. Also, it is to be understood that the phraseology and terminology employed herein is for the purpose of description and should not be deemed limiting.

Wearable Device for Humans

The devices of the invention when configured for humans can promote survival during the "golden hour." After an object penetrates and damages the user's tissue and blood vessels the device can apply pressure to the site of the wound in order to reduce or stop the loss of blood. Preferably the user is wearing the device prior to receiving the wound. When damage to the user occurs, the system will automatically provide on-site treatment. The device may also be triggered manually (e.g., by the user or another person), and/or stabilize the entire body of the wounded person, e.g., for transportation purposes. The device may be a full body suit or it may be configured as a wearable garment, such as a vest, pants, sleeve, wrap, sock, helmet, glove, or brace.

Figure 3A:
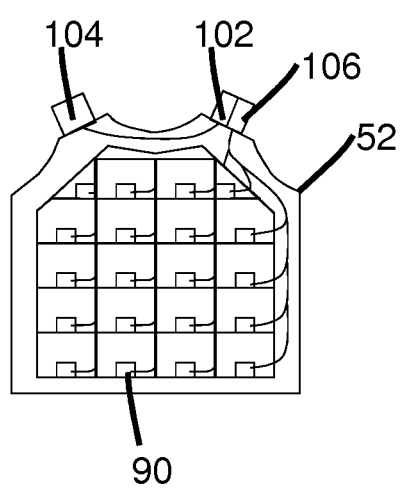
FIG. 3A is an illustration showing a top view of the device of the invention integrated into a bullet resistant vest.
Figure 3B:
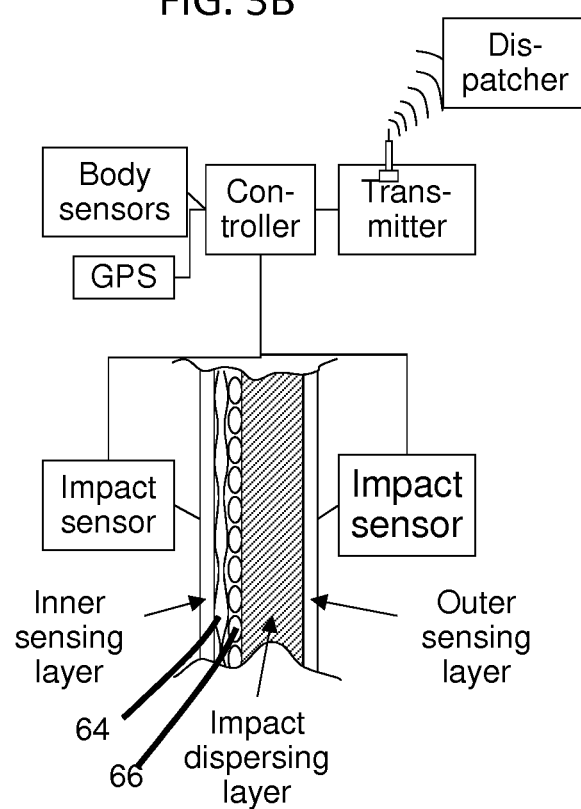
FIG. 3B is an illustration showing a cross-sectional view of the device of FIG. 3A.
Figure 4A:
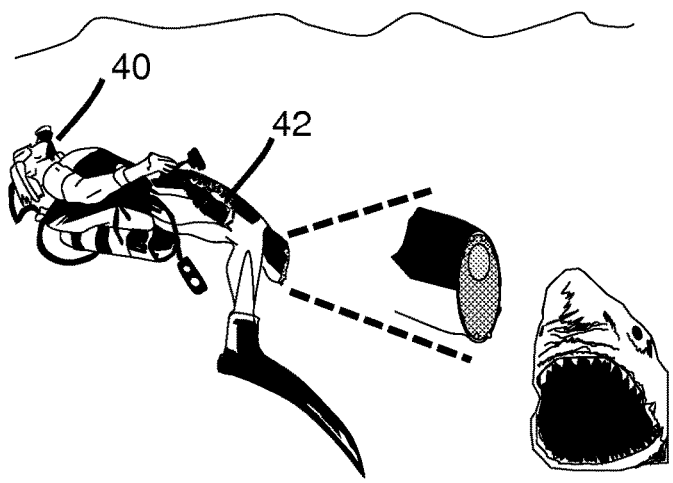
Figure 4B:
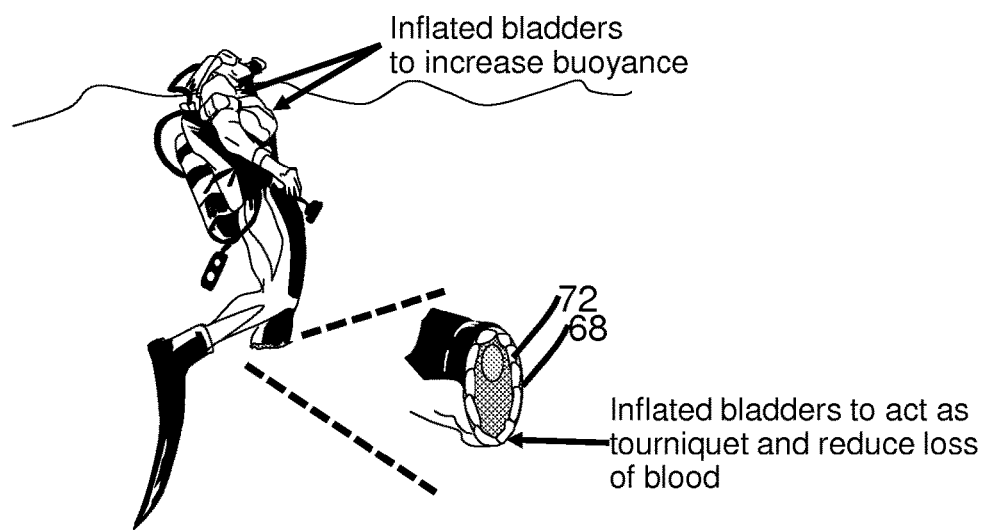
FIG. 4B is an illustration of the device of FIG. 4A after activation showing inflation of the bladders.

In order to maximize the efficiency of the device, the system may be integrated into several different configurations, such as into a full-body suit, a vest, and a wound dressing (see, e.g., FIGS. 1A-1E). However, if desired, only selected areas of the body can be covered by the device, e.g., the device may be worn as a garment that covers only those areas of the body that are crucial for survival, e.g., the torso, neck, and/or groin (e.g., as a jacket shown in FIG. 2, or vest as shown in FIG. 3). Configuring the device to cover only a select area of the body will reduce the weight and will decrease the complexity of the device.

Figure 7:
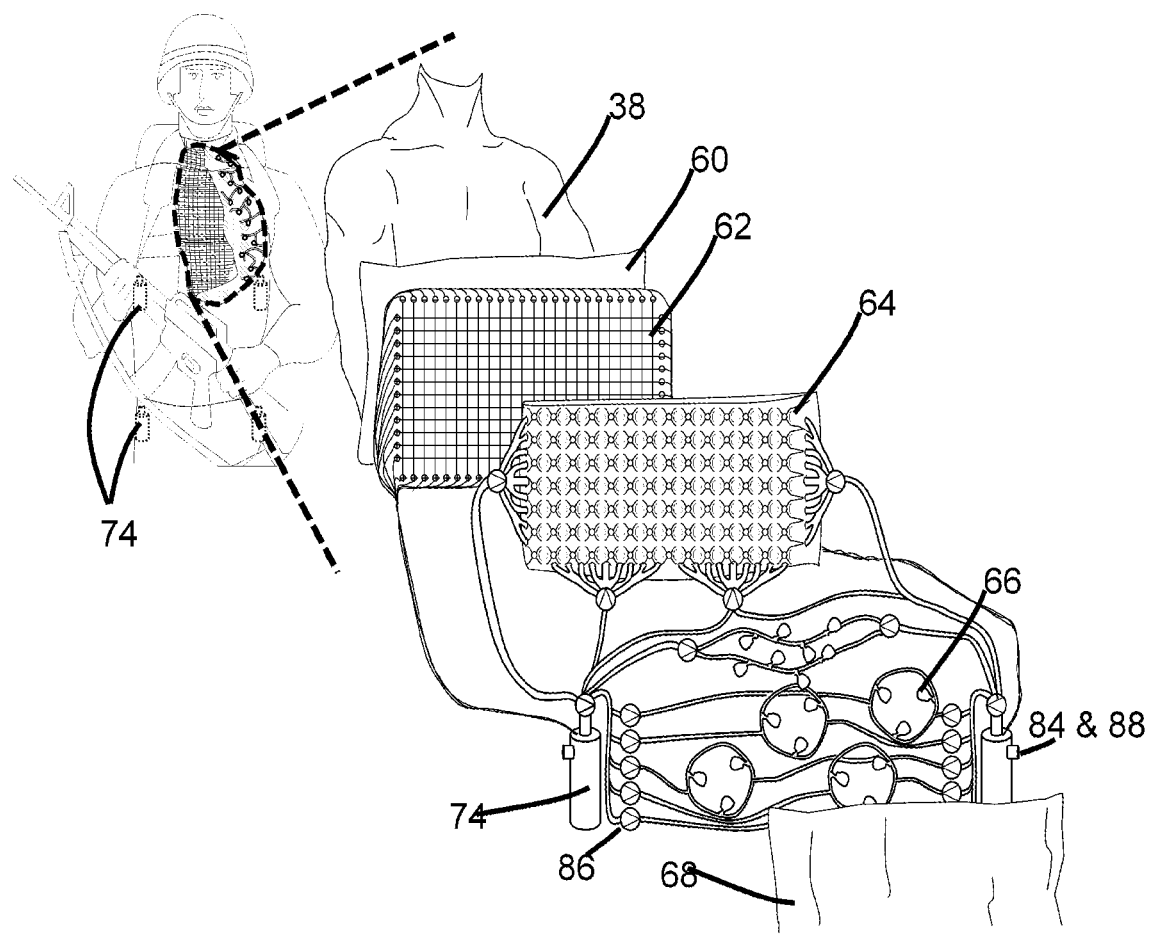
FIG. 7 is a schematic showing a cut-away view of the device shown in FIG. 2. The inset shows an exploded view of the device, in which the different layers of the device (e.g., the inner layer, impact detection layer, wound sealant compartment layer, inflatable bladders layer, outer layer) are shown.

A device of the invention for human use may include one or more functional layers, including, for example, the following: an inner 60 and outer layer 68, an impact detection layer 62, a layer that contains the wound sealant 64, and a pressure (on the body of the user) generating layer that includes the bladders/balloons 66. The layers do not need to be separate units, but rather can be combined within one layer or system (e.g., combining the detection capabilities with the wound sealant delivery system as shown in FIG. 7). Also, if chosen, one can incorporate only one or multiple layers (e.g., one could only have the detection layer, or the detection and the bladder layer, or only the wound sealant layer).

In a preferred embodiment, a device of the invention is one that is capable of providing all functions, i.e., impact detection, wound sealant, and pressure generation. The functions may be controlled and powered by a "central unit" 74, which includes among other things, one or more of the following: electronics, such as a micro-processing unit 102 and a communication device 106, GPS unit 104, and/or body sensor, also, valve arrays 108, a pressurized medium container 98, and/or a gas generator, and a power source 96 (see FIGS. 7 and 11).

All functional layers, in a device of the invention, are integrated in a unit that can be worn as a vest 52, a jacket 30, as pants or as a full body suit 32 (see FIG. 1, FIG. 2, FIG. 3, and FIGS. 4 A&B). The outer layer can be made out of any garment, textile, rubber, leather, or other organic and/or inorganic material. The device may be provided in a form that can be worn separately (without any additional external clothing), or it may be integrated into other existing clothing or body protection system. Examples for existing wearable clothing into which the present system could be incorporated include: body armor (e.g., armored vest and/or suit); a uniform (e.g., uniforms of security and law enforcement personnel, such as, a police uniform or prison guard's uniform; motorcycle jackets, pants and suits; motorsport racing suits; other sport suits, such as skiing/snowboarding suits, watersport suits (e.g., diving suits); aerospace and aviation suits, and immersion survival suits.

If used with a diving or immersion survival suit (FIGS. 4 A&B), the system may be tailored to also provide buoyant force capabilities, and to provide a watertight seal around the neck or extremities (e.g., the cuffs of the arms and/or the ankles), to help a wounded and potentially unconscious user to stay afloat and increase the chance of survival. The pressure applied around the neck and/or extremities may be, e.g., less than 11 psi, 5 psi, 2 psi, 1 psi, or 0.5 psi.

Integrating part (or all) of the system into traditional working or conventional clothing might also allow a user, such as, e.g., a person with hemophilia, to carry out activities they might otherwise be restricted from doing.

The following section describes the function of the device for use with a human body 38 (see, e.g., FIG. 7). The general function and process steps are as follows: an object penetrates the outer layer and the functional layers (FIG. 8A-8G), which include an impact detection system, a wound sealant, and a bladder system. Preferably, the layers are arranged with the impact detection and wound sealant layers closest to the body, and the network 70 of bladders 72 on top of these layers, further away from the body.

The impact detection system identifies the location on the body where the impact 80 of an object occurred and may also determine the degree and severity of the impact. This data 82 is sent to an information processing unit (incorporated in "the central unit" 74), which triggers the release of a pressurized medium 76 (e.g., a gas, such as a non-flammable or an inert gas, in particular air, carbon dioxide, or argon), to the layer containing the wound sealant 78 and the layer including the bladder system. Only the region where the impact has occurred will be pressurized in order to direct the flow of wound sealant to this site and to inflate only bladders in this region. The object that penetrated the layer(s) of the device may have also destroyed part of the system (see, e.g., FIGS. 8B and 8C). The partial destruction of, e.g., the wound sealant layer creates an opening 80 through which the sealant can flow. This may occur once the wound sealant compartment layer is pressurized from the sides. The effect is similar to puncturing the side of a toothpaste tube, and pressurizing the (otherwise) enclosed tube. The toothpaste will follow the flow of least resistance, and will flow through the punctured hole. In this case, it is the wound sealant that will flow to the site of the destruction and the wound, e.g., see FIGS. 8D and 8E.

At the same time (or before or after), the bladders are pressurized in the area of the impact. The pressurized medium will inflate one or more bladders that were not destroyed through the impact, (e.g., see FIGS. 8F and 8G), and that are activated by the device. The bladders are very small when deflated (e.g., an area of about 10 mm×10 mm to 50 mm×50 mm, and 1 mm to 10 mm in thickness), but will increase significantly upon inflation (e.g., up to 10 cm×10 cm to 20 cm×20 cm and 1 cm to 10 cm in thickness). The bladders are connected within a network 70, e.g., a network of tubing or similar structure. The flow resistance in the network is equal to or higher than the forces required to inflate the bladders. This will ensure that the area of the network that might be destroyed through the impact of the object will not act as the "path of least resistance" (which would cause the pressurized medium solely to "escape" through this site, without inflating remaining bladders in this area). However, choosing this simple method of higher resistance in the pressured medium feeding network, all remaining activated bladders will be inflated.

Figure 8B:
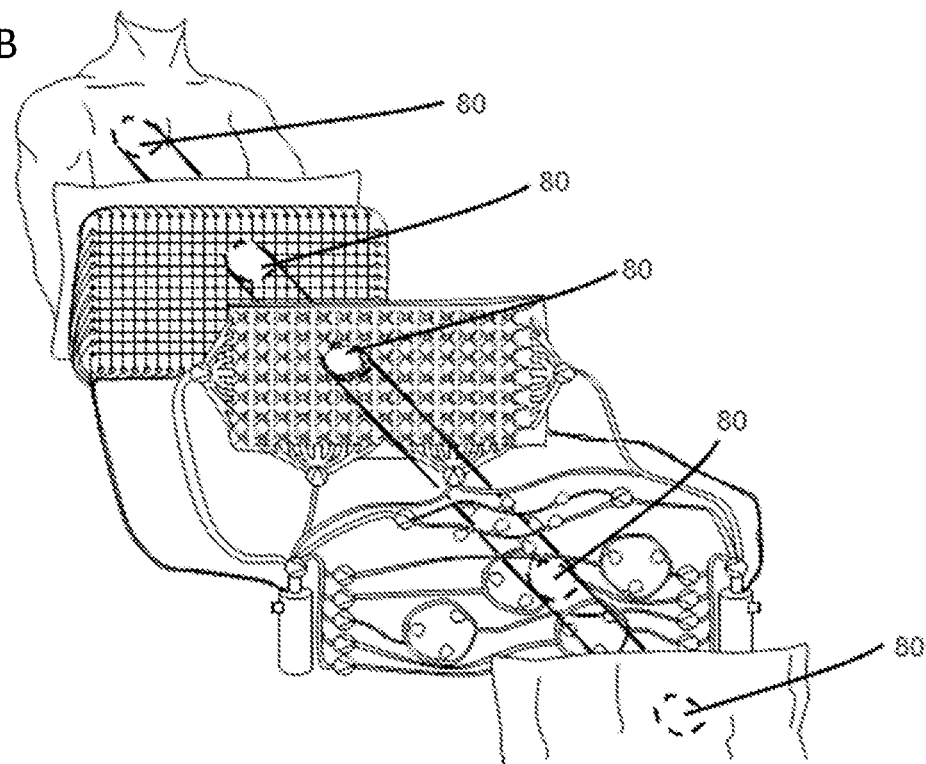
FIG. 8B is a schematic showing an exploded view of the device of FIG. 7 after an impact with an object that partially penetrates and destroys the various layers.
Figure 8C:
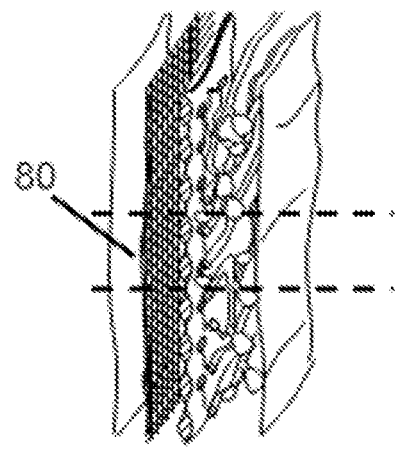
FIG. 8C is a cross-sectional view of the device of FIG. 8B.
Figure 8D:
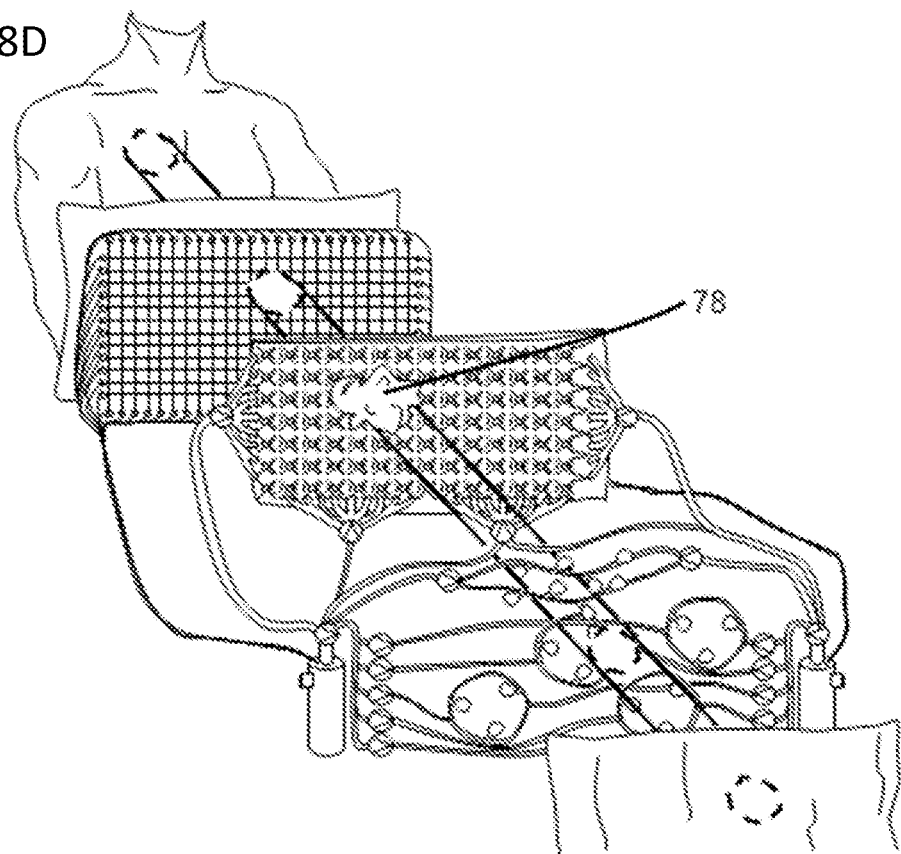
FIG. 8D is a schematic showing an exploded view of the device of FIG. 8B after the wound sealant starts flowing to the site of the destruction.
Figure 8E:
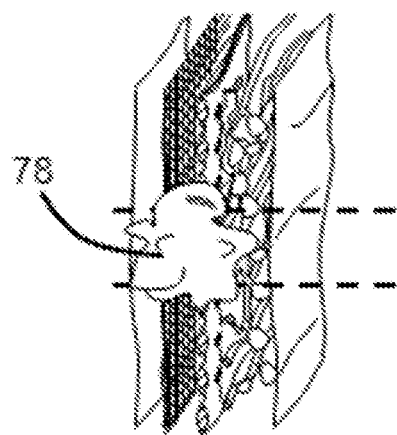
FIG. 8E is a cross-sectional view of the device of FIG. 8D.
Figure 8F:
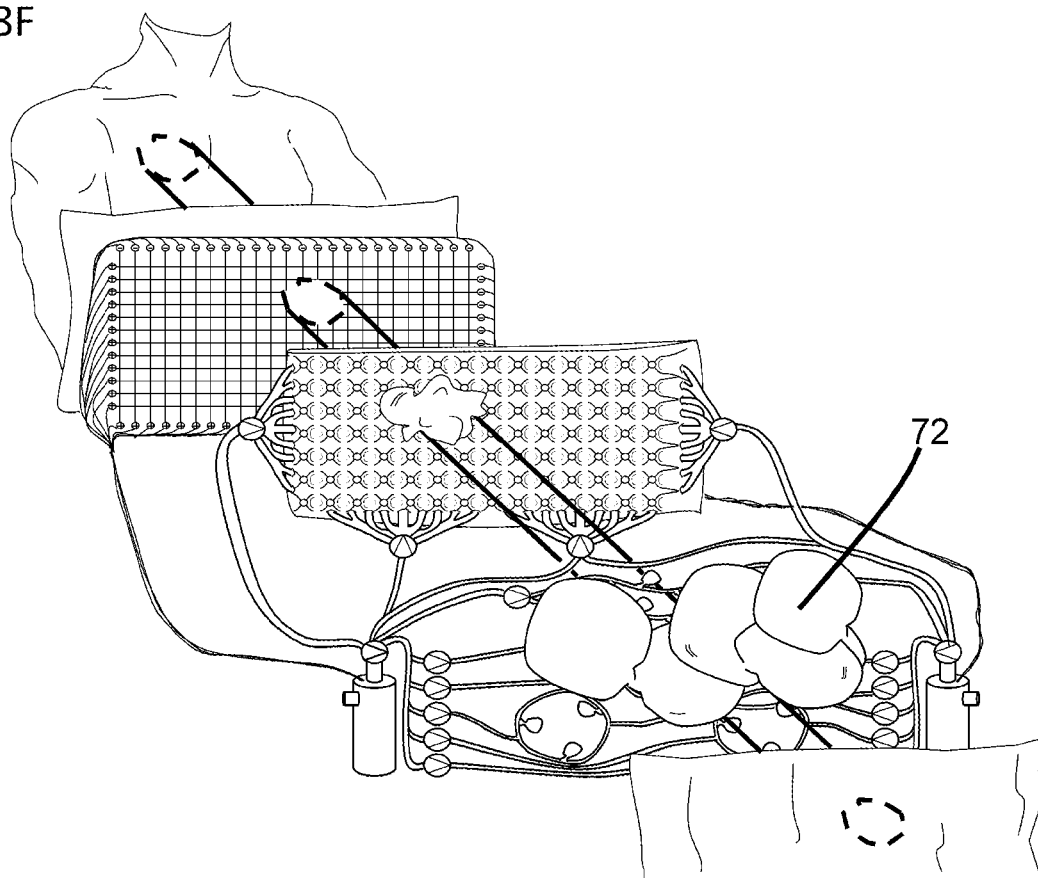
FIG. 8F is a schematic showing an exploded view of the device of FIG. 8C after the bladders inflate.
Figure 8G:
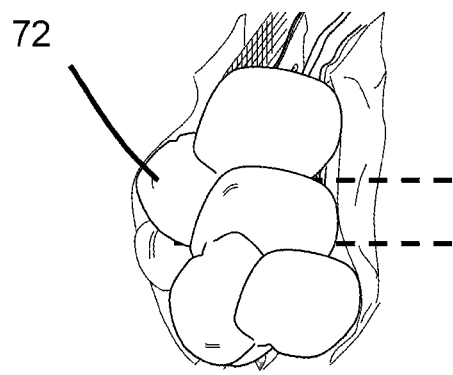
FIG. 8G is a cross-sectional view of the device of FIG. 8E.

Another solution is to integrate a multitude of valves 86 (FIG. 10), which will direct the flow as envisioned. When the bladders inflate, their expansion movement is restricted by the outer (garment or similar) layer. This will ensure that pressure is built up towards the body and the site of the wound, (FIGS. 8F and 8G). The pressure to be applied on the site of the wound should be approximately in the range of twice the blood pressure, i.e., around 220-240 mmHg (or 4.3-4.6 psi) over normal atmospheric pressure of 760 mmHg (or 14.7 psi). Because of the large dimensional increase of the bladder (e.g., increasing from 10 mm to 10 cm in diameter), they will seal off the site of the destruction (especially in combination with a wound sealant), applying continuous pressure to the wound.

The pressure inside the balloon will depend on the type of material, and the thickness and geometry used in order to allow for such an increase in size, but will typically be around 20 psi. Depending on the design choice however, balloons similar to the ones used in angioplasty may be used as well, with nominal pressures typically ranging from 90-120 psi.

The information processing unit may also trigger the transmission of data, such as an emergency beacon signal, that may be used to indicate the location of the user, e.g., using a global positioning module incorporated into the device. It may also process data from body sensors (e.g., to measure heart rate, etc.), if integrated.

In case of an electrical system malfunction, or if desired by the user or another person, the device can also be activated using a manual override. The manual override can be used to trigger all or a part of the system. For example, a rip cord 84 (FIG. 11) having a handle attached thereto may be positioned on a front portion of the vest/suit and connected with the valve system of the pressurized medium, such that the person wearing the device can manually open the valve to release the pressurized medium therefrom. Hence, the rip cord may facilitate manual activation of the system.

In case of a malfunction of the pressurized medium system, it is possible to manually inflate the bladder layer and to pressurize the wound sealant layer compartment or both. This can be done by using an external pump, or by orally "blowing" into the inlet valve 88 (e.g., see FIG. 7 and FIG. 11), similar to a procedure of inflating a life jacket. Examples of this type of component may be the model V73000 (a breather tube and relief valve with dust cap, which is designed for applications requiring oral filling and pressure relief for overpressure protection) manufactured by Halkey-Roberts, of St. Petersburg, Fla., or the equivalent.

All functions may have at least one additional backup system. For example, in a scenario with a backup system, there would be one or more additional information processing units, one or more additional containers with pressurized medium, and/or one or more additional inlet networks to connect to the wound sealant compartment and the bladders.

As discussed below, the layered system approach could also be used for completely different purposes, not only for humans, but also for other living species or manmade objects or other entities, e.g., as a protection layer 34 on ships 36 (FIG. 5) or oil tanks (FIG. 6), which could seal off entry sites caused through an impact.

Wearable Device for Animals

Animals in warfare have a long history starting in ancient times. From 'war dogs' trained in combat to their use as scouts, sentries and trackers, their uses have been varied and many continue to exist in modern military usage and in civilian police practice.

To increase the chance of survival for animals in case of tissue damaging object penetration, the device embodiment previously described for human usage may be tailored to allow for usage on animals, e.g., a multi-functional-layer system, including an impact sensor layer, a wound sealant layer (if desired), and a compression layer.

The device may be worn by itself as a type of vest, or can also be integrated into existing systems, such as an armored vest, e.g., as shown in U.S. Pat. No. 6,123,049, or the canine vest INTRUDER™ (K9 Storm, Winnipeg, Canada).

Figure 12:
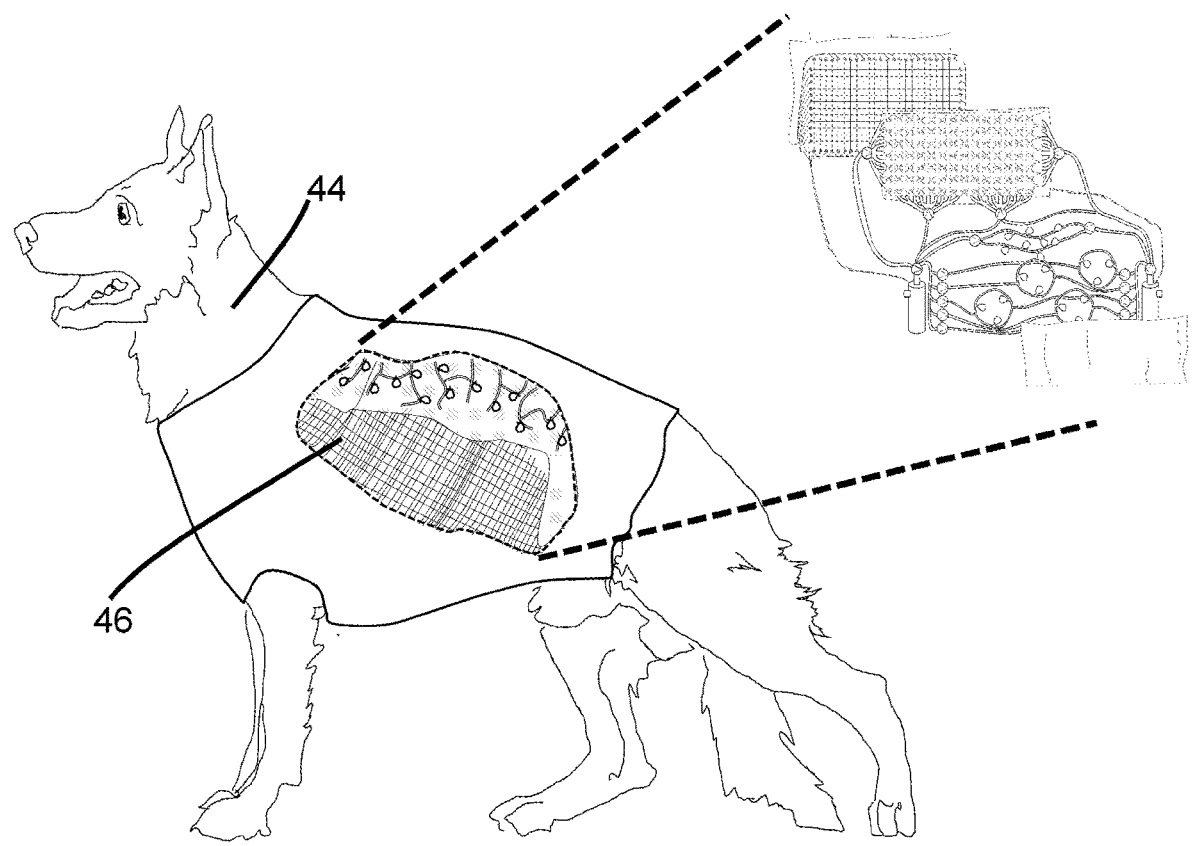
FIG. 12 is a schematic showing a cut-away view of the device of the invention configured for use on a dog. The inset shows an exploded view of the device.

FIG. 12 illustrates a vest on a canine.

Device for Use with Inflatable Objects

The functionality and operability of an inflatable object, such as an inflatable raft, may be greatly reduced upon partial or full destruction of its segments. Often, even a partial destruction of segments can lead to a critical reduction of the overall structural integrity of an inflatable object.

The proposed embodiment for use with inflatable objects may include an impact detection layer, a layer with a sealant (e.g., a liquid polymer sealant), which is tailored to the materials which may be sealed (e.g., polyurethane-coated nylon) and the surrounding environment (e.g., sea water, working temperature, etc.). The embodiment may also include a layer that exhibits pressure on the site of destruction, which may be also used to increase, e.g., buoyant forces. In addition to the layers, a central unit that processes the sensor input signals, activates the sealant, and the pressure/buoyant system, and triggers information transmission (e.g., distress signal, status of location, status of the amount of damage taken) may be used.

Figure 5:
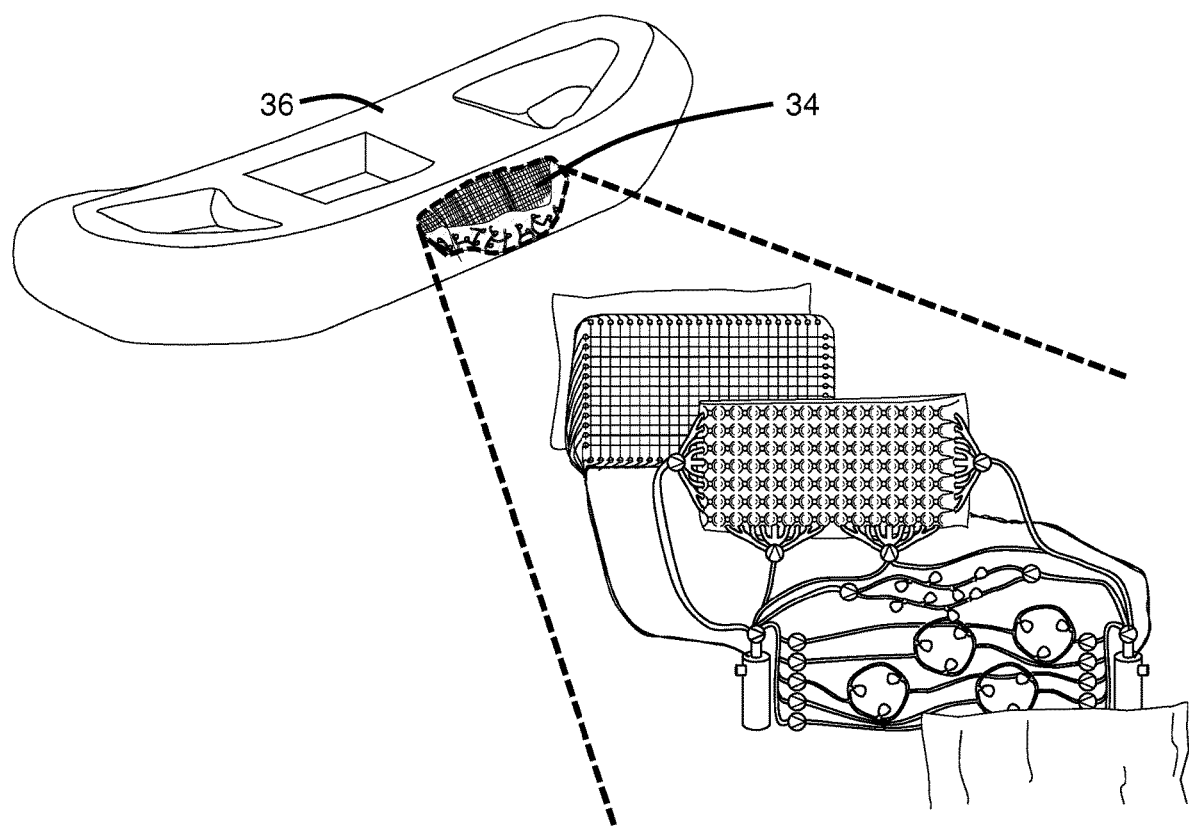
FIG. 5 is a schematic showing a cut-away view of a device of the invention configured for use on a rubber boat (the inset shows an exploded view of the device).

FIG. 5 illustrates a device embodiment configured for an inflatable object.

Figure 6:
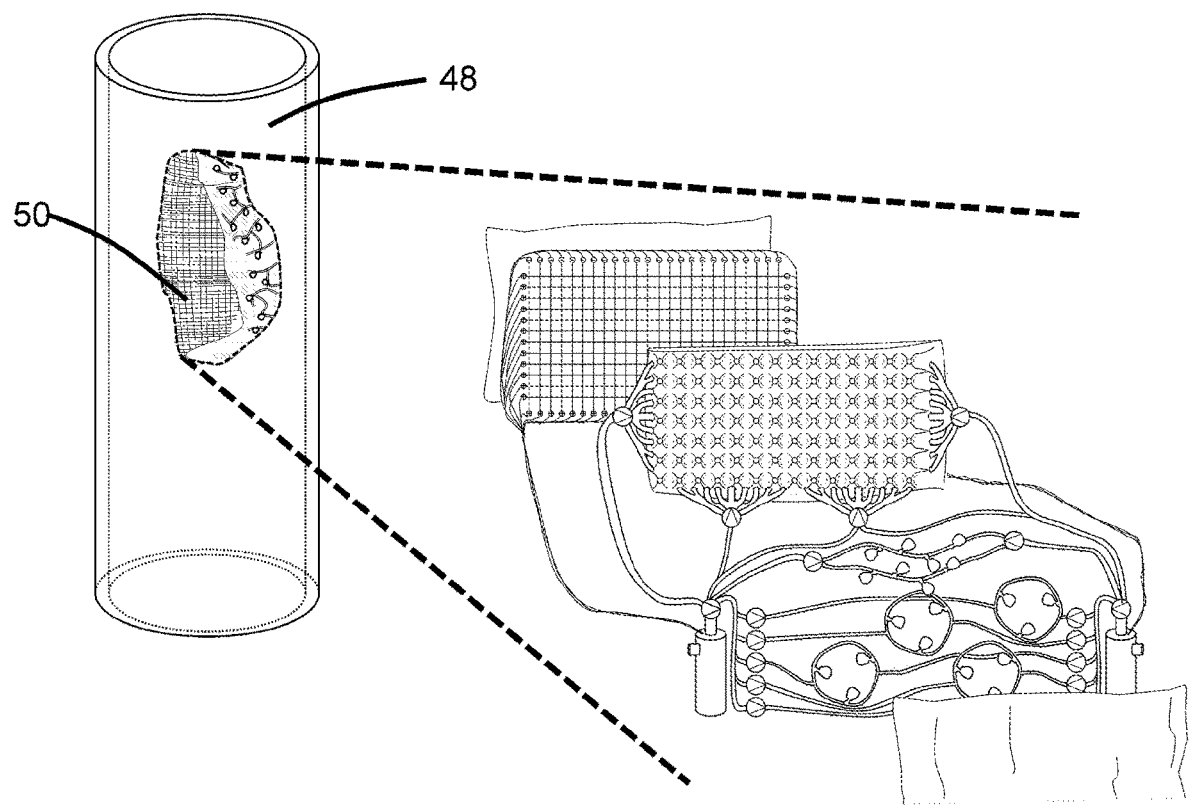
FIG. 6 is a schematic showing a cut-away view of a device of the invention configured for use on an oil tank (the inset shows an exploded view of the device).

Device for Use with Machines (e.g., Vehicles) The device of the invention may also be configured for usage with any type of machine or object where "sealing off" of a leak may be envisioned, e.g., sealing off an oil tank's wall or a ship's side wall upon penetration by another object (see e.g., FIG. 6).

Functional Layers

Now that the device and examples of its use have been generally described, the following provides a detailed description of the components and parts of the devices and systems of the invention.

Inner Layer

The inner layer is closest to the torso and should provide a sufficient comfort level to the user, i.e., it should be able to transfer body heat and moisture and help keep the body at a comfortable temperature level. Any known garment can be used for this layer. For functional consideration the layer is typically designed to be light weight so as not to encumber the wearer. (e.g., materials such as Spandex may be used). Synthetic fabrics that may be used in the devices of the invention include, but are not limited to, polyester, acrylic, nylon, rayon, spandex (e.g., LYCRA®, ELASPAN®, and ACEPORA®), GORE-TEX®, MEMBRAIN®, TEVENT®, HYVENT®, and KEVLAR®.

In regards to thermal properties, the design must consider the thermal insulation needs of the wearer. In hot situations, the inner layer should allow the wearer to stay cool; while in cold situations, it should help the wearer to stay warm.

The entire system should also be able to transfer sweat away from the skin, using, for example, moisture transferring fabric. Spandex (e.g., LYCRA®) is a popular material used as a base layer to soak up sweat. For example, in activities such as skiing and mountain climbing this is achieved by using layering: moisture transferring materials are worn next to the skin, followed by an insulating layer, and wind and then water resistant shell garments. A similar approach may be used for particular configurations of the device of the invention.

Impact Detection System

The main purpose of the impact detection system is to determine if the wearer was hit by a fragment, or any other object. It may also detect where on the body (of the wearer) the impact occurred. The system will especially record hits that cause destruction of the outer (and inner) garment (or body armor, etc.) and that penetrate body tissue (e.g., causing hemorrhage). The impact detection system is comprised of one or more impact detection sensors.

There are multitudes of technical solutions that can be envisioned for this layer, e.g., using piezoelectric modules, fluid carrying tubes (also integrated within the wound sealant layer), a conductive mesh incorporated into the garment of the inner layer, or other. Some of these solutions are described in more detail below.

Piezoelectric Systems

Piezoelectric systems 90 may be incorporated into the invention as an impact detection system, (e.g., see FIG.

13A). An example of a piezoelectric system suitable for use in the invention is described in U.S. Pat. No. 5,195,752, incorporated herein by reference.

An example of an off-the-shelf product is the multi-purpose piezoelectric sensor LDT1-028K (Measurement Specialties, Inc., Hampton, Va.), which can be used to detect physical phenomena, such as vibration or impact. The piezo-film element is laminated to a sheet of polyester and produces a useable electrical signal output when forces are applied to the sensing area. The dual wire lead 92 attached to the sensor allows a circuit or monitoring device to process the signal. Another example is the sensor PZ-01 (Images SI Inc., Staten Island, N.Y.). These sensors are laminated; a 1251 µm polyester layer is laminated to a 28 µm or 52 µm piezo film element. When used in a "bending" mode, laminated film elements develop much higher voltage output when flexed than a non-laminated element series. The neutral axis is in the laminate instead of in the film so the film is strained more when flexed. The capacitance is proportional to the area and inversely proportional to the thickness of the element.

Figure 13A:
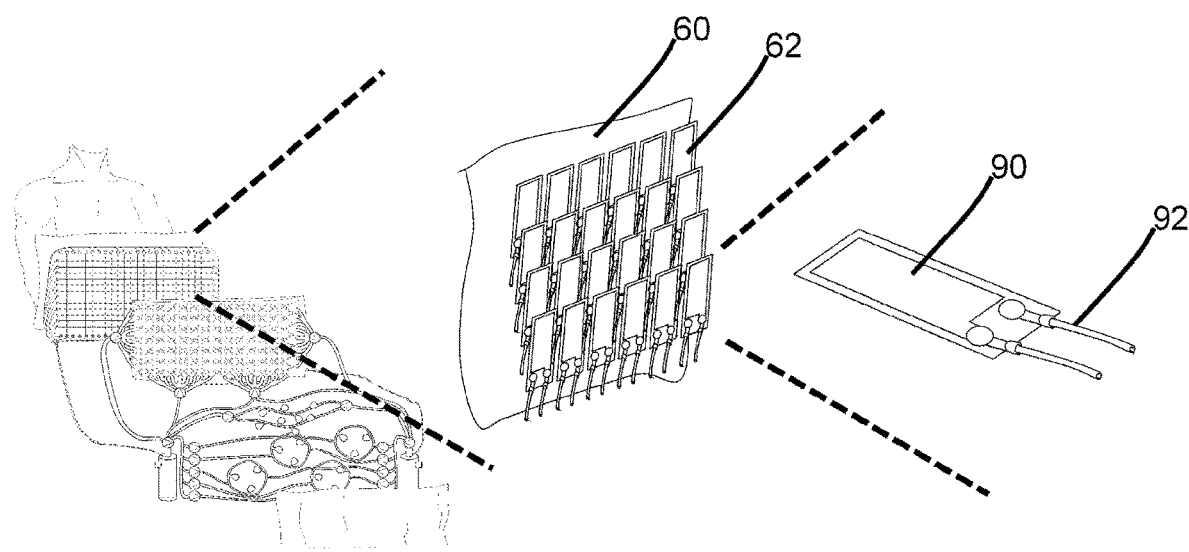
FIG. 13A is exploded view showing an impact detection layer of the invention that includes piezo-electric sensors.

FIG. 13A illustrates a layer of piezoelectric film, polyvinylidene fluoride (PVDF) coated with thin metalized layers, connected to suitable electrical leads held in place, for example, by means of a double-sided adhesive. The overall thickness of the layer of piezoelectric film is approximately 0.3 mm.

Also, the piezoelectric material can be encased in a protective jacket (e.g., urethane).

In case of a piezoelectric system, one can envision a layer of piezoelectric film as taught in U.S. Pat. No. 5,195,752, e.g., polyvinylidene fluoride (PVDF) coated with thin metalized layers, connected to suitable electrical leads. Deformation of the piezoelectric film caused by an impact to the sensor vest produces an electric signal which varies in amplitude depending on the force of the impact. The impact signal is carried over leads to an operational amplifier which in turn feeds the impact signal to a micro-controller over wire. The micro-controller receives the impact signal as an input from a voltage regulator.

Within the micro-controller there is an analog to digital converter circuit and a compare circuit. The analog to digital converter circuit changes the impact signal from a vest sensor from an analog signal to a digital signal, which is sent over wire to the compare circuit. The compare circuit is also connected to a programmable read-only memory (PROM) circuit by wire. Contained within the PROM are the parameters defining the limits of the amplitude of a digital signal created by an object impact and the body coordinates, which can be used to determine the location of the impact. These parameters are compared with the signal received from vest sensor in the compare circuit and, when a match is found, a signal is sent over wire to trigger the controlled release of the compressed medium to the wound sealant layer and/or the bladders at the location desired.

Also included in the control module may be a radio frequency (receiver and) sender, the purpose of which is to send signals, such as a distress-signal, (e.g., to friendly units, first responders, other police officers, other prison guards, etc.). In addition, a global positioning device may be used to determine the location of the vest and generate a signal corresponding to that location. The global positioning device may transmit the location signal when an impact signal is generated. More sensors may be integrated into the layers, such as, sensors for measuring the heart rate, blood pressure, temperature, or moisture level. The information generated from these additional sensors may be recorded on a data storage system (e.g., a flash memory based system) and/or may also be transmitted.

As can be seen from the above description, the sensor layer is responsive to impact forces, and through the deformation of the piezoelectric film, sends an impact signal to control module that compares the amplitude of the impact signal with preprogrammed amplitudes of impact signals. When a match is found, a signal is sent to trigger the activation of the (wound) sealant flow, the inflation of the bladder, and/or a distress signal informing others that the vest wearer has been hit by an object.

The pressure sensing layer can be composed of several distinct plates of piezoelectric material such that the location of the impact can be detected with more particularity, (e.g., see FIG. 13A).

Another example of a piezoelectric system suitable for use in the invention is described in U.S. Pat. No. 6,349,201, incorporated herein by reference. The device described in U.S. Pat. No. 6,349,201 relates to bullet-proof vests and, more particularly, to such vests having the capability of selectively providing distress and warning signals to remote locations. The apparatus described includes: a vest having an outer sensing layer, an inner sensing layer and a central layer disposed between the inner sensing layer and the outer sensing layer; in which the inner sensing layer and the outer sensing layer respectively initiate an impact signal and a penetration signal when they are respectively subjected to an impact above a predetermined level; a transmitter adapted to broadcast a signal notifying that at least one of an impact signal and a penetration signal is generated; a global positioning device for determining the location of the apparatus and generating a signal corresponding to that location; and means for actuating the global positioning device to transmit the location signal when one of the impact signal and the penetration signal is generated.

Certain design elements from U.S. Pat. No. 6,349,201 can be incorporated in the present invention, such as the multilayer approach for impact sensors, as well as the incorporation of a GPS, body sensors for temperature, heart rate, pressure, and tilt, and a radio distress signal sending unit. Preferably, several independent segments (rather than just one, as described in U.S. Pat. No. 6,349,201) are used to detect the location of the impact more precisely. Also, rather than having an impact dispersion layer between the inner and outer sensing layer, the previously described wound sealant layer 64 and the inflatable bladders layer 66 are sandwiched between those layers, (e.g., see FIG. 3). If combined with, e.g., body armor, the impact dispersion layer will be kept in place between the inner and the outer sensing layer.

Using a multi sensor layer approach, the sensing layer is a first sensing layer, the device further comprising a second sensing layer attached to the protective layer opposite the first sensing layer; the distress signal varies on whether the first sensing layer sends an impact signal, whether the second impact layer sends an impact signal, or whether both sensing layers send impact signals; the impact signal may vary depending upon the strength of the impact.

By incorporating a similar technology in the devices of this invention, using several segments of this inner and outer sensing layer, one can detect the location of the impact more precisely. The signal generated by the impact can then trigger the activation of the gas generator and/or the release of the compressed medium to start the wound sealant flow or to inflate the bladders in the desired area or both. In addition, a distress signal and the location of the wounded person, as well as information regarding the condition of the wounded person may be broadcast.

Figure 14:
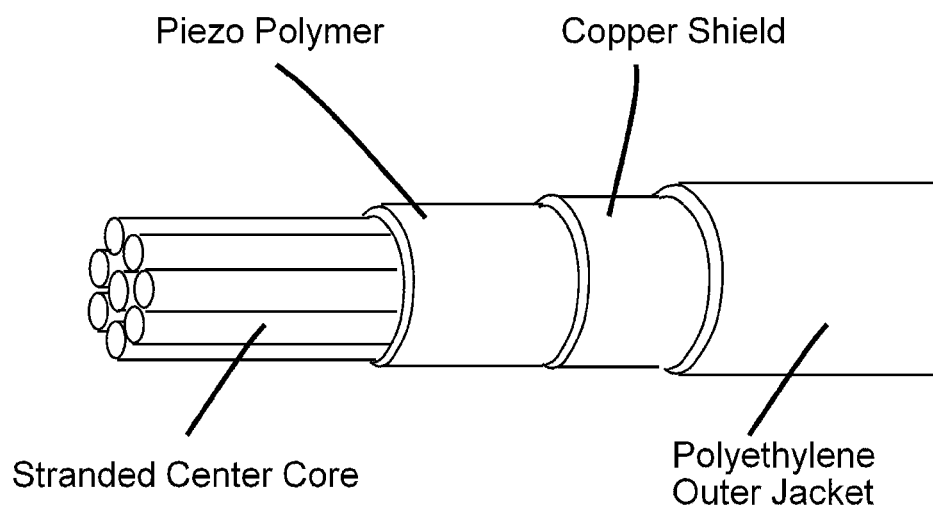
FIG. 14 is a schematic showing an example of a piezoelectric cable for use in the devices of the invention.

In another embodiment of the invention, piezo-cables (e.g., see FIG. 14) are used, such as the model PZ-07 (SI Inc., Staten Island, N.Y.). The cables are woven into the other layers. Designed as a coax cable, the piezo polymer is the "dielectric" between the center core and the outer braid. When the cable is compressed or stretched, a charge or voltage is generated proportional to the stress. Piezo cable has a number of advantages in certain applications. Due to its coaxial design, the cable is self-shielded, allowing its use in a high EMI environment. The piezo cable can be spliced to passive coax, using standard coax splice techniques. It is extremely rugged and will stand up to heavy loads.

Fluid Carrying Tubes

Another method that can be employed to detect impact on the pressure sensing layer is a weave of conductive, fluid-carrying tubes. An example of such fluid-carrying tubes is described in U.S. Pat. No. 5,636,378, incorporated herein by reference. The described apparatus senses impact and activates a transmitter to send a recorded message. The apparatus comprises a vest which is constructed using woven tubing, wherein the tubing generally forms a tight mesh throughout the vest. The tubing is connected with a reservoir of electrically conductive fluid; thus, the fluid fills the tubing and reservoir. Moreover, the fluid communicates with a pair of leads for maintaining a constant and low-level electrical contact there between.

The woven tubing is covered with cloth and a hardening substance, such as epoxy; wherefore, the tubing will break when the vest receives a significant impact. When the tubing is broken, the fluid escapes from the tubing and breaks the electrical contact between the leads, thereby activating a transmitter to send a recorded message. In addition, a position sensor is attached to the transmitter for activating the transmitter to send the recorded message when the apparatus is maintained in a non-vertical position for a predetermined period of time.

The methodology described in U.S. Pat. No. 5,636,378 can be tailored to be used with the wound sealant system/layer instead of one or more fluid-carrying tubes. The wound sealant may be an electrically conductive fluid. The fluid communicates with a pair of leads to maintain a constant, low-level electrical contact there between. When the layer is broken, the fluid escapes from the tubing/layer and breaks the electrical contact between the leads, whereby a transmitter is activated, triggering the signal transmission and the pressurizing of the wound sealant compartment and the bladders layer. This approach helps in further simplifying the overall system, reducing complexity and the amount of parts required, and decreasing the overall weight.

Conductive Mesh

Figure 9:
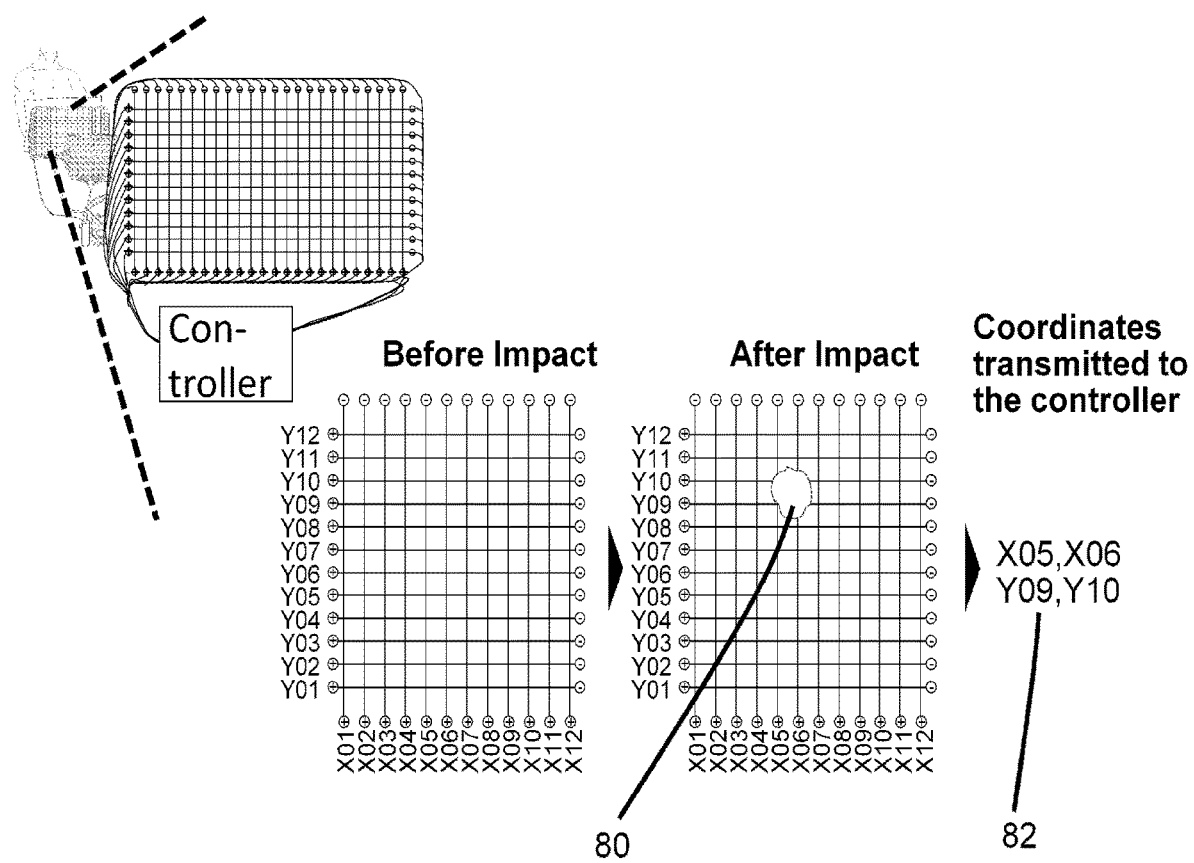
FIG. 9 is a schematic showing an illustrative view of an impact detection layer of a device of the invention transmitting the coordinates of the site of the impact to a controller.

Another way of detecting a disruption of layers is by weaving electrical conductive material into the garment (e.g., micro wires or conductive thread, such as the 6-ply thread with low resistivity of about 4 Ohms per linear foot (Cat. # DEV-10120, SparkFun Electronics, Boulder, Colo.)). This can be used to create, e.g., a mesh, that can be used to produce a coordination system (see, e.g., FIG. 9) that allows the identification of an impact site. The wires are shielded and protected from the environment and are linked via leads to the controller unit. One may also use conductive fabrics with low resistivity, such as the copper coated polyester "Pure copper Polyester Taffeta" (Cat. # A1212, 0.05 Ohm/sq resistivity, Less EMF Inc., Latham, N.Y.) or "Stretch", a silver plated nylon/elastic composition (Cat. # A321-ac, Less EMF Inc.). In addition to fabric with low resistivity, one also requires pressure sensitive ESD materials with high resistivity to construct the impact detection layer. "Pressure sensitivity" refers to materials that exhibit a decrease in resistance as pressure on the material increases. Examples are carbon-impregnated polyolefin "Velostat" conductive film (Product #1704, volume resistivity <500 Ohms/cm, 3M Electronic Products Division, Austin, Tex.) or Ex-Static (Cat. # A1209, 10^5 Ohm/sq resistivity, Less EMF Inc.) or "Quantum Tunneling Composite" (Cat. # A253, 63 MOhm resistivity for a 4×4×1 mm piece, Less EMF, Inc.), or others.

Figure 13B:
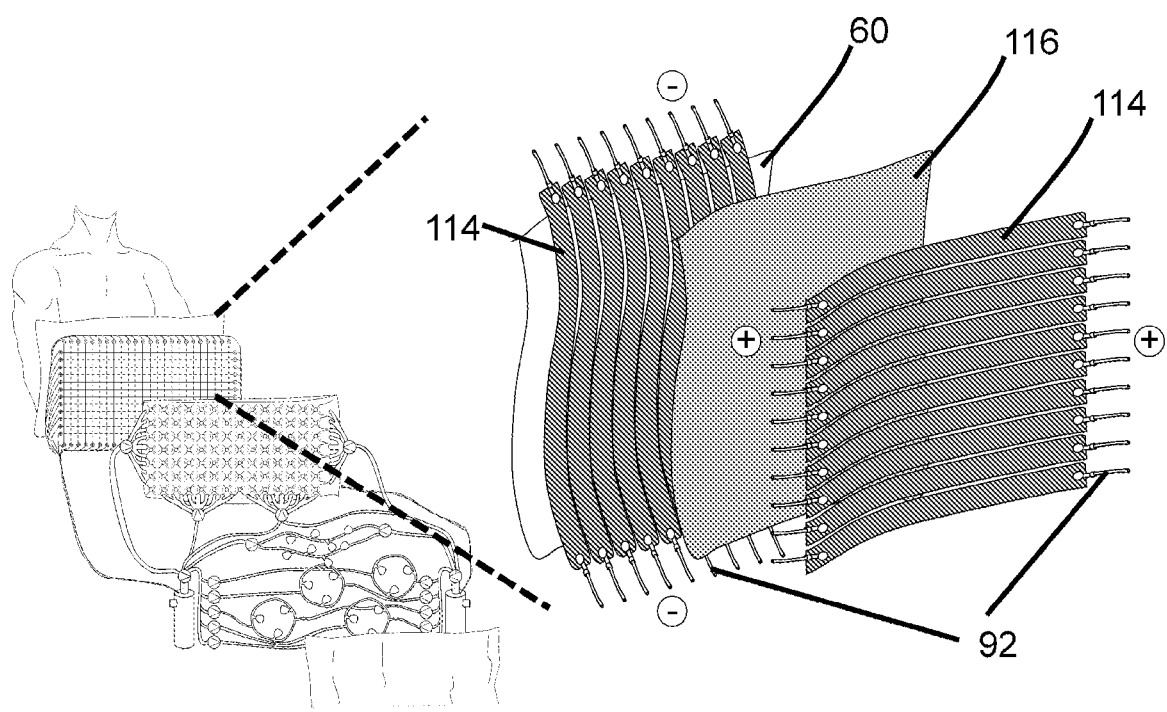
FIG. 13B is an exploded view showing an impact detection layer of the invention including a layer of pressure sensitive conductive fabric with high electrical resistivity sandwiched between two layers of conductive fabric with low electrical resistivity. The polarity shown in FIG. 13B is solely for illustrative purposes and is not meant to be limiting.
Figure 13C:
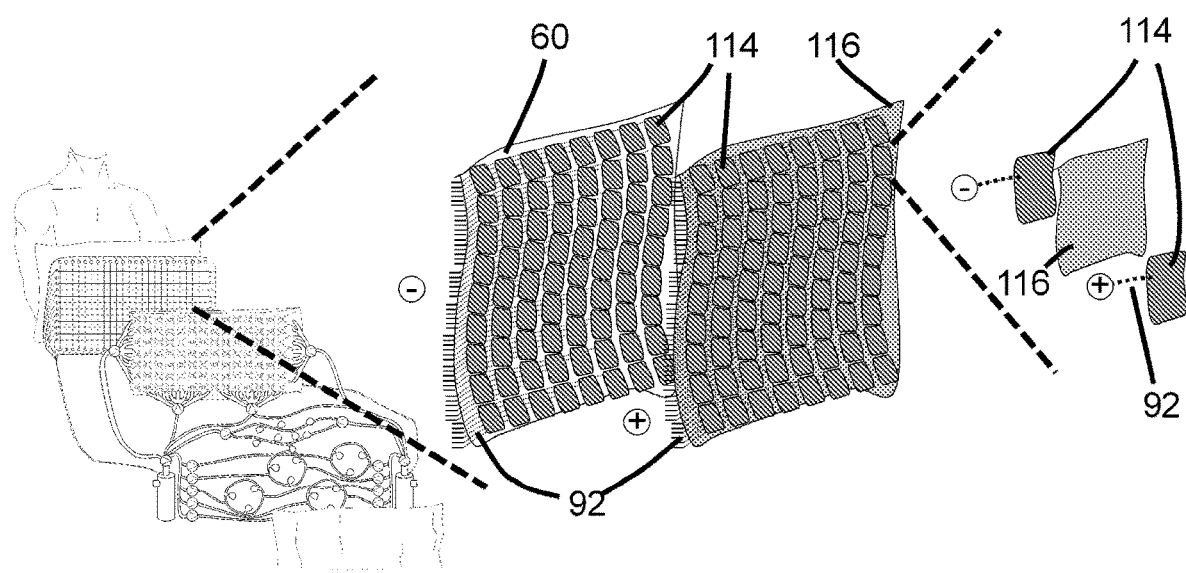
FIG. 13C is an exploded view of the impact detection layer shown in FIG. 13B using more segmented individual patches of conductive fabric with low electrical resistivity. The polarity shown in FIG. 13C is solely for illustrative purposes and is not meant to be limiting.

The impact detection layer is sandwiching the pressure sensitive layer 116 in-between two conductive layers with low resistivity 114, (e.g., see FIGS. 13B and 13C). The upper and the lower layer have opposite polarity and are connected to the energy source and the micro controller. The sandwiched layer 116 has a very high resistivity so that no current can flow between the outer and the inner layer. Once an impact occurs, and the layers get compressed by the impact, the resistivity of the pressure sensitive layer declines and allows for a current to pass through. The layers act as a fabric pressure sensor. As the inner and outer conductive layers 114 are setup in a matrix-like manner, one can simply identify the x and y coordinates where the impact occurred, as well as the strength of the impact. If the impact by the fragment was high enough to penetrate the layers, the signal received by the central processing unit will be at a maximum. Depending on the level of the impact the central processing unit will trigger the previously described cascade of events (see also FIG. 15).

Sealant Layer

The device of the invention may incorporate a sealant layer. The sealant layer may be an encapsulated system. For example, the tubing/reservoirs may form a sealed network for containing the fluid/wound sealant. As previously described, the electrical conductivity properties of this system can be also used for detecting the impact. The wound sealant layer is preferably designed in a shape that allows for transpiration and makes it comfortable to wear. The layer has to be geometrically flexible in order not to restrict any body movements of the wearer. For instance, one can envision a design as shown in a cross-sectional view in FIG. 16, which illustrates a flexible grit-like layer with holes that allow for a breathable system. It may be made out of a polymer-based material, and may have more than one layer (e.g., one inner layer that allows for sealing off the wound sealant, and an outer layer to protect against environmental influences).

In use, once the wearable system receives a significant impact, which would be sufficient to break the wound sealant layer/tubing, a signal is triggered, while the wound sealant is released from the tubing and communicating reservoir. Additionally, a rip cord can be manually pulled to initiate the inflation of the bladders and the flow of sealant. In case the electrical conductivity of the sealant is used for detection purposes, as the fluid is lost from the tubing or associated reservoir, the constant electrical contact is broken between the leads.

Figure 16:
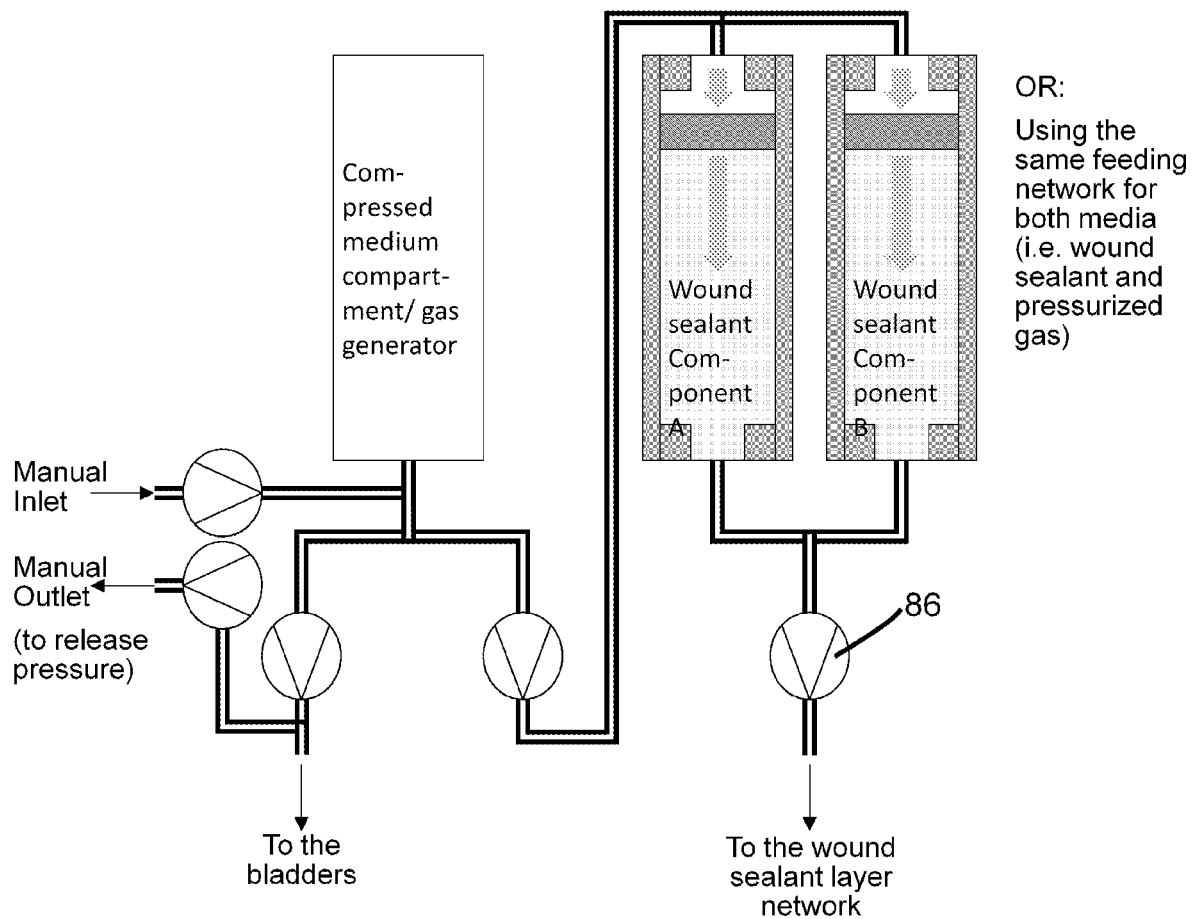
FIG. 16 is a schematic showing the wound sealant compartment layer that can be incorporated into a device of the invention.

The encapsulated wound sealant system 64 will have one or more inlets that are sealed off via a valve 86 or similar, FIG. 16. One can also envision a seam, that opens up once pressurized from the side, e.g., as described in European Patent Application No. 20070795363. A frangible seal of the container may burst when squeezed thus allowing the components in the container to mix within the container. Once the trigger signal is received, a unit containing pressurized medium (e.g., inert gas), or a miniature gas generator, will release the medium through the inlet into the encapsulated wound sealant layer/reservoir. In case of a reservoir being in use, one can also envision a hollow cylinder, which contains a movable inner cylinder that separates the hollow cylinder in two compartments, one containing the wound sealant, while the other one will have the pressurized medium coming in, once triggered, e.g., FIG. 17. Once the pressurized medium flows into that compartment, the volume and pressure increases, which will move the separating cylinder-segment towards the wound sealant containing compartment, and by this pressurizing the same. The wound sealant will follow the path of least resistance and flow to and out of the site where the damage/disruption of the layer/tubing occurred. In case the wound sealant comprises two or more components, which require separate storage, and which need to be "mixed" upon usage, one can envision two or more reservoirs, connected via a valve system, which leads to a "unifying tube" that mixes the components and leads to the network of tubes, i.e., to the wound sealant layer, FIG. 17.

Also this layer may have a backup system in place, i.e., if one pressurizing unit fails, or the inlet has been destroyed or malfunctions, another unit will pressurize the wound sealant layer, using additional inlets. If chosen, one or more pressurizing units can be also used at the same time, to enhance the wound sealant delivery speed to the site of the impact.

European Patent No. 2040997 and others discuss a multiple compartment pouch with frangible seal, including a polymeric film, multiple-compartment container having an internal frangible seal comprising a curved portion and variable width with a maximum width near the portion of the curve having the smallest radius of curvature. This device may be used for confining a fluid and related beverage container with a re-closable fitment for storing and delivering two different flavored liquids or the like. The frangible seal of the container will burst when sustained squeezed thus allowing the components in the container to mix within the container.

Sealant

Configuration for Mammals

There are several types of would sealants that may be used with the devices of the invention. Several of these are described in detail below and others are well known in the art. Wound sealants 78 may be broadly defined as any biomaterial that, when applied, can react and adhere to underlined tissues via physiochemical or biological reactions to provide desired functions. Specifically, a wound sealant may attach to a tissue by molecular cross-linking or through mechanical interlocking with the underlying tissue. Wound sealants are also referred to as tissue sealants, adhesives and glues in the literature.

The wound sealant has to be designed in a way that allows it to be able to flow to the site of wound, once the wound sealant layer compartment is pressurized, and to start cross-linking in situ. Examples can be liquid collagen-based wound sealants, as described in U.S. Pat. No. 6,509,031. The wound sealant can be in a dry, liquid, or even foam-like state. Peng et al. describe further details and examples of wound sealants in their publication "Novel wound sealants: biomaterials and applications" (*Expert Rev Med Devices* 7(5):639-59, 2010). According to Peng et al., wound sealants broadly fall into three types (biopolymers, synthetic polymers, and biosynthetic composites) with multiple forms. Commercially available and clinically studied materials may be categorized as solid sheets normally known as dressings, solid particles, powders, fibers, hydrogels, liquid tissue sealants, and dispersions, made from natural or synthetic polymers, ceramics and their combinations. Examples are (see Table 1): fibrin-based sealants, sprayable-foam fibrin sealants, dry fibrin sealants, collagen sealants, gelatin sealants, albumin sealants, keratin sealants, mussel-derived sealants, biological glues, polysaccharides, such as chitosan sealants, alginate glue, chondroitin sulfate glue, synthetic biomaterials, such as cyanoacrylate, polyurethane, dendrimer-based sealants and biologically inspired sealants, composite biomaterials, such as two-polymer hydrogels, and multicomponent systems.

TABLE 1

Classification of wound sealant biomaterials in surgery (Peng et al., *Expert Rev Med Devices* 7(5):639-59, 2010).

| | Material form | Surgical functions | Examples |
|---|---|---|---|
| Biopolymers | Fibrin liquid and solid sealants | Hemorrhage control, wound closure and tissue anastomoses, fixation of bone fractures | Fibrin liquid sealants (Tisseel ®, Crosseal ®) and foam, dry sheet, powder with different fibrinogen and thrombin compositions |
| | Collagen mixture | Hemostasis for general surgery, retroperitoneal injuries | Bovine microfibrillar collagen, bovine thrombin, suspension mixed an equal volume of plasma during application (CoStasis ®) [dagger] |
| | | Hemostasis in adenoidectomy spine surgery; for example, cervical anterior discectomy with fusion, lumbar decompression with fusion | Collagen particle-thrombin suspension (Proceed[trademark]) |
| | Gelatin solution and dispersion | Hemostasis in a variety of surgical procedures and anatomical sites, including femoral bypass, carotid endarterectomy, cardiac valve replacement and cardiopulmonary bypass grafting, partial nephrectomies, nephrolithotomy, endoscopic sinus surgery and transphenoidal pituitary surgery | Gelatin particle-thrombin suspension (FloSeal ®)[double dagger] |
| | | Vascular anastomosis, pneumostasis Closure of skin wounds | Gelatin-resorcinol-formaldehyde § Gelatin-genipin/carbodiimide/epoxy |
| | Albumin solution | Vascular anastomosis, wound closure, bone fixation | Albumin-glutaraldehyde (BioGlue ®) |
| | | Hemostasis | Albumin laser solders without indocyanine green |
| | | Tissue welding | Albumin solder with genipin |

TABLE 1-continued

Classification of wound sealant biomaterials in surgery (Peng et al., *Expert Rev Med Devices* 7(5):639-59, 2010).

| | Material form | Surgical functions | Examples |
|---|---|---|---|
| | Chitosan solution, gel and film | Hemostasis in lingual bleeding | Chitosan |
| | | Nerve anastomosis | Chitosan and crosslinker (indocyanine green or genipin) |
| | | Hemostasis in carotid artery, seal lung air, skin wound closure | Photo-crosslinkable chitosan with azide and lactose moieties |
| | | Sealing arterial puncture sites | Microcrystalline chitosan gel |
| | | Closure of sclera lacerations | Chitosan film without laser welding |
| Synthetic polymers | Liquid Sealants | Superficial wound closure and approximiation | Cyanocrylates |
| | | Tissue bonding | Aminopropyltrimethoxysilane-methylenebisacrylamide siloxane |
| | Two separation solutions | Inhibiting suture line bleeding | PEG sealants: tetra-succinim idyl and tetra-thiol-derivatized PEG (CoSeal ®) |
| | | Closure of ileostomy | PEG sealants: tetra-succinim idyl and amine PEG (SprayGel [trademark]) |
| | | Incisional cerebrospinal fluid leak after posterior fossa surgery; retina reattachment; nerve anastomosis; vascular closure | PEG sealants: tetra-succinimidyl PEG and tri-lysine amine (DuraSeal [trademark]) |
| | | Sealing of fluid leaks | PEG sealants: polyesterpolyol acylates and benzophenone |
| | | Sealing of pulmonary air leak, hemostasis in anastomotic bleeding; wound closure | Poly(ethylene glycol)-co-trimethylene carbonate-co-lactide (Mr 20,000) with acrylated end groups/eosin Y[dagger] (FocalSeal ®) |
| | | Sealing of pulmonary air leakage | Poly(ethylene glycol)-co-poly(a-hydroxy acid) diacrylate macromers/2,2-dimethoxy-2-phenylacetophenon[dagger] (AvdaSeal ®) |
| | | Acute aortic dissection | Poly(ethylene glycol)-co-poly(a-hydroxy acid) diacrylate macromers |
| | Pre-polymer Solution | Bone fixation | Acrylic resins |
| | | | Epoxy resins |
| | | | Polymethymethacrylates |
| | | Bone fixation, sealing of vascular graft, hemostasis | Polyurethanes |
| Synthetic polymers | Gels | Partial nephrectomy repair, wound closure | SynthaSeal [trademark] |
| | Solid | Sealing bleeding bone surface | 75 wt % of glycerol-ogliolactic-co-glycolic acid (Mw 1000) and 25% PEG (Mw 800) |
| | | Tissue bonding | Lactic acid-caprolactone ogliomers |
| Biosynthetic composites | Liquid Solution | Hemostasis in spleen bleeding | Gelatin-poly(I-glutamic acid) with water-soluable carbodmiides |
| | | Soft-tissue adhesion | Gelatin-polyacrylic acid with water-soluable carbodmiides |
| | | Hemostasis- and anastomosis-aid in laparotomy, abdominal and thoracic aortas | Benzophenone-derived gelatin and PEG diacrylate |
| | Solid | Closure of vascular incision | A poly(I-lactic-co-glycoloc acid) scaffold doped with bovine serum albumin and indocyanine green dye |

Configuration for Inanimate Objects

There is a large range of adhesive and sealant formulations. Adhesives and sealants may be classified in many different ways, such as by cure (bonding) mechanism, chemistry type, and application (e.g., structural vs. non-structural). Any sealant with suitable properties may be used in the sealant layer of the invention.

Figure 17:
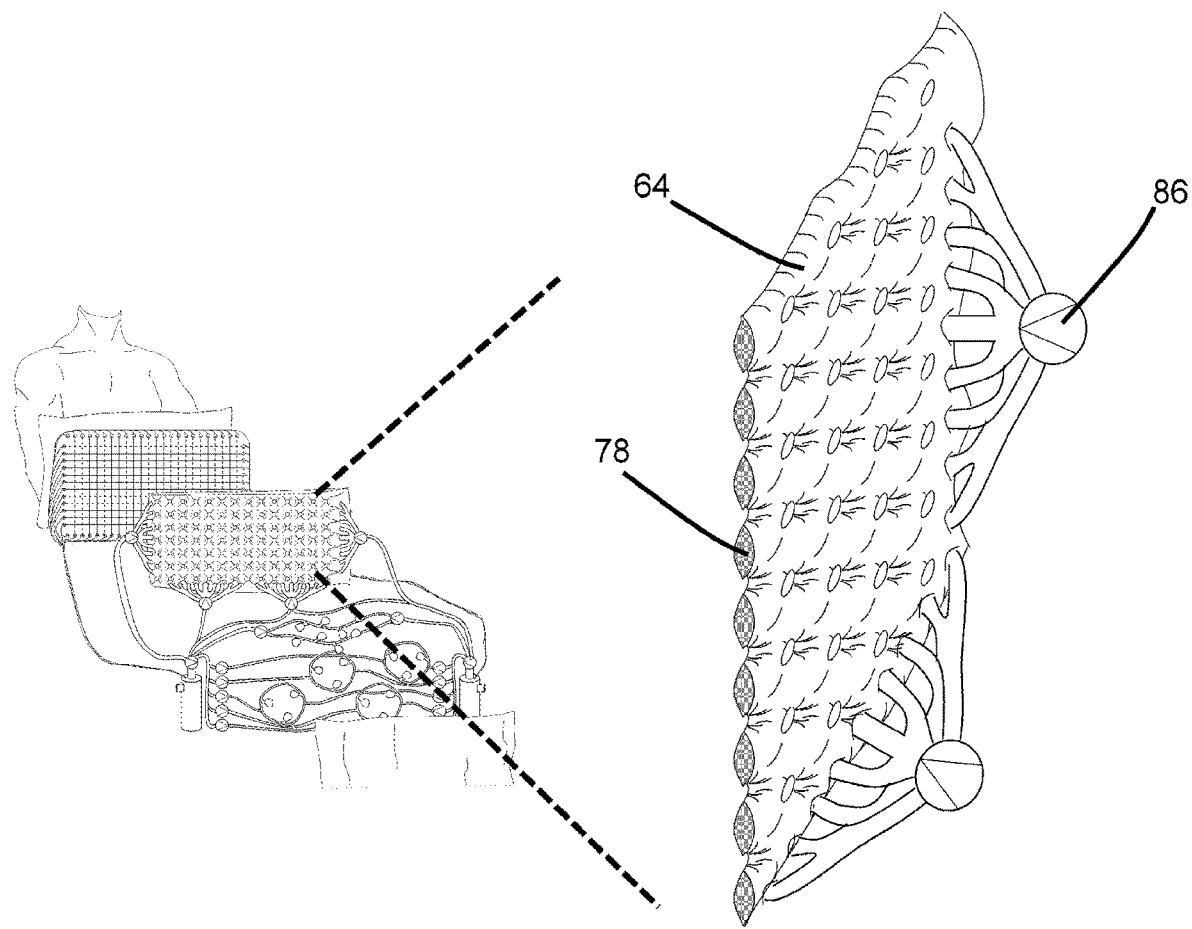
FIG. 17 is a schematic showing an illustrative view of the compressed medium compartment or gas generator and the connecting tubes and valves leading to a wound sealant compartment.

For use in this invention, the sealant needs to be able to flow through a network of tubes, and once this network is damaged, fill any space to close the damaged site, and start the curing process. The choice of the sealant will depend mainly on the materials, surfaces, and environment of the device of the invention. For instance, a coated steel oil tank will require a different combination and type of sealant then a rubber boat. If a two-component system is used, the compartment and driving mechanism may be designed, e.g., as shown in FIG. 17.

Compression and/or Buoyant System

The devices of the invention include a compression system that applies pressure to the impact site. The system typically includes inflatable sections (i.e., bladders) which could also be used to create buoyant forces. Examples of compression systems that may be incorporated into the devices of the invention are described in detail below.

One example of a compression system suitable for incorporation into the devices of the invention is described in U.S. Pat. No. 3,933,150 (incorporated herein by reference). In this system, the apparatus includes a single piece of double-walled material that can receive pressurized gas. Inflation of the device causes pressure to be exerted on an individual wearing the apparatus, thereby decreasing the volume of pooled venous blood, and stabilizing the individual during transport. The specific material utilized in the invention is not disclosed, but types of plastic are described.

Another example of a compression system is described in U.S. Pat. No. 7,329,792 (incorporated herein by reference). In this system, which includes an apparatus for promoting hemostasis, especially of skin penetrating wounds of the periphery, the device includes fluid impermeable barriers surrounded by exterior dams to be held in place over a wound by applied force.

A further example of a compression system is described in U.S. Pat. No. 6,939,314 (incorporated herein by reference). The system utilizes a bladder that is comprised of a plurality of individual sections that are preferentially in fluid communication with each other. When the bladder is disposed over the sternum of a patient and inflated (e.g., with a gas or fluid), pressure is exerted on the chest of the patient. The positions of the sections of the bladder are fixed with respect to each other and the device does not provide flexibility with respect to positioning of the bladder sections (or selective employment of those).

Another example of a compression system suitable for use in the devices of the invention is described in U.S. Pub. No. US20100179586, incorporated herein by reference. A device that consists of a belt system with one or several inflatable bladders, that can be selectively positioned and inflated over exsanguinating blood vessels, for use in control of a hemorrhage in regions of the body where it is difficult to apply conventional compression. The belt is adjustable to different levels of tightness.

A still further example of a compression system is described in U.S. Pub. No. US20130041303, incorporated herein by reference. A device for maintaining a desired amount of tension surrounding a person's hips and pelvis to securely support and stabilize a pelvis that has been fractured is disclosed. The device may also be used to secure a pressure applying device to a person so that blood vessel-occluding pressure can be applied.

Further examples of compression systems are described in U.S. Pat. Nos. 6,554,784 and 7,008,389, incorporated herein by reference. Devices which can be used to encircle the hips of an injured person are described. The devices can provide the proper amount of hoop tension to urge the parts of a person's fractured pelvic ring toward a normal relationship and thus reduce internal bleeding at the site or sites of fracture.

Figure 10:
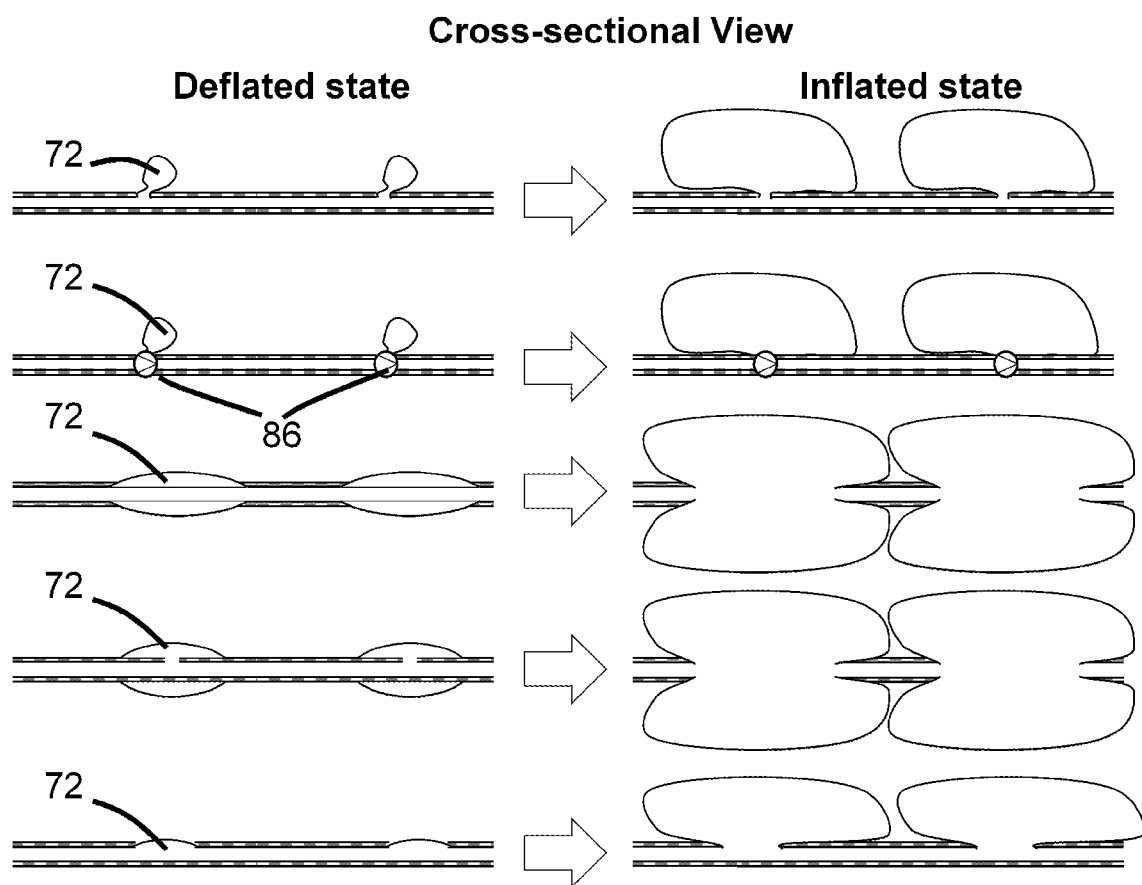
FIG. 10 is a schematic showing a cross-sectional view of a selection of different bladder configurations for use in a device of the invention.
Figure 11A:
FIG. 11A shows an image of a representation of a central unit as shown in FIGS. 7 and 8.
Figure 11B:
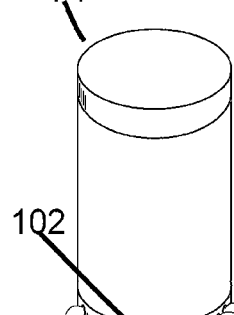
FIG. 11B is a detailed illustration of the central unit of FIG. 11A.
Figure 11B:
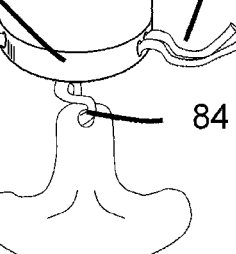
Figure 11C:
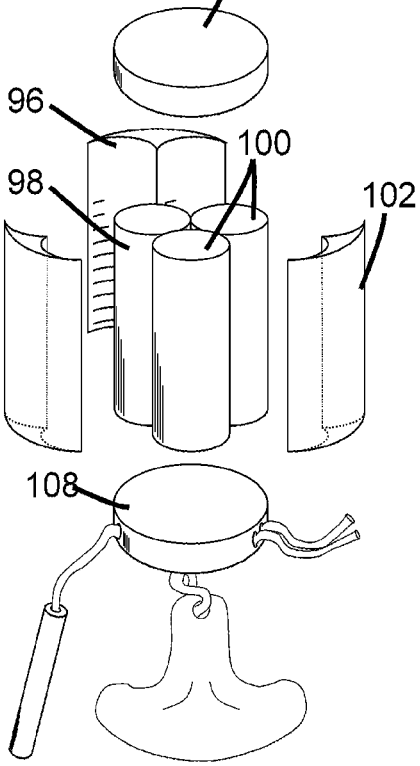
FIG. 11C is an exploded view of the central unity of FIG. 11B showing internal components that may be incorporated into a device of the invention.
Figure 18:
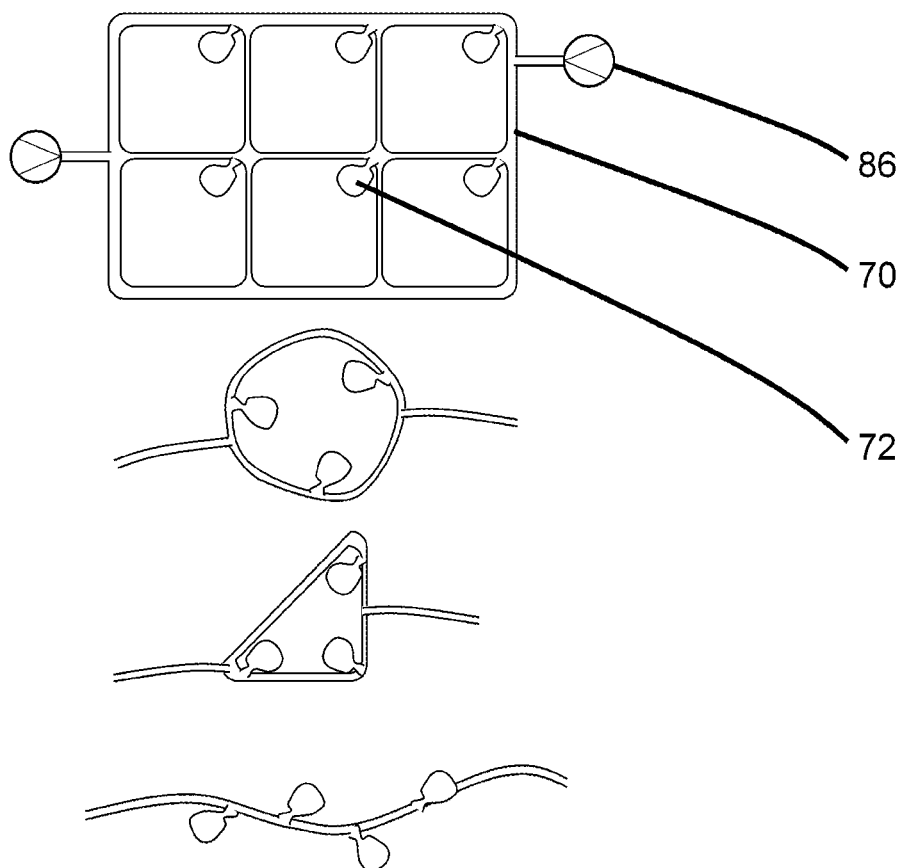
FIG. 18 is a schematic showing a top view of a selection of different geometrical bladder configurations for use in a device of the invention.

In a preferred embodiment, the compression system may comprise a network of tubes or similar, which can feed a pressurized medium to individual bladders. The network may comprise several regions that can be inflated individually. FIG. 10 and FIG. 18 illustrate a few variants of the network. The bladders may be very thin (in the 1 millimeter and even down to the micrometer range) and small in a deflated state (with a deflated size in the 10 mm×10 mm range or below) and will increase significantly upon inflation (with an inflated size having a diameter of several cm for use at humans and animals and even larger for use at machines). The pressure to be applied to the site of the wound should be, as previously mentioned, approximately twice the blood pressure, i.e., around 220-240 mmHg or (4.3-4.6 psi), over normal atmospheric pressure (760 mmHg). The pressure to be applied on the site of an entrance point within a machine application greatly depends on the system pressure (e.g., oil pressure, water pressure, etc.) that act on the site of destruction, which may be about 100 psi or above.

The bladders may be made out of a flexible material, such as rubber, latex, polychloroprene, nylon fabric, or others. The bladders preferably display near-to-gastight properties.

The inflation and valve system in place may ensure that during the inflation process the surface tension will never exceed the tensile strength of the balloon (to prevent the balloon from bursting).

The bladders may have sensors integrated in them, for example, as described in the publication "Materials for multifunctional balloon catheters with capabilities in cardiac electrophysiological mapping and ablation therapy" by Kim et al. (*Nature Materials,* 10, 316-3232, 2011). In this paper, the authors exploit the balloon catheter as a platform for heterogeneous collections of high performance semiconductor devices, sensors, actuators and other components. Commercially available catheters (8-18 Fr, BARD, USA; Creganna, Ireland) serve in this case as platforms for the devices. Components that integrate with the balloons are formed on semiconductor wafers using adapted versions of planar processing techniques and methods of transfer printing reported by Kim D H, et al. (*Proceedings of the National Academy of Sciences,* 105, 18675-18860, 2008) in "Materials and noncoplanar mesh designs for integrated circuits with linear elastic responses to extreme mechanical deformations". Wrapping the resulting collections of interconnected devices on the balloon in its deflated state completes the process.

Using a similar process, one can envision integrating body sensors, but also the functions of the detection layer into the sealant and/or the bladder layer.

The tube (or similar) network 70 connecting the bladders may be flexible, to allow for adequate body movement. The pressurized medium container may be connected to the bladder network via (one-way) valves 86. As with all the other systems, there may be at least one backup system. In the case of one additional system, the various regions of the network can be inflated from the main side, but also from the backup side. This is especially important, in case multiple impacts have occurred, crippling the feeding network.

The flow resistance of the network, the valves, the bladders/balloons, and the pressurized medium container are all engineered and balanced in a way, so that upon triggering the system, the bladders will inflate to a determined volume. The outer layer of the overall device allows only for limited stretch of the material, thereby restricting the geometric deformation of the inflating bladders towards the site of the wound, and thereby applying pressure.

Preferably, the pressure is applied right after the wound sealant starts flowing towards the site of the wound.

The automated detection of the site of the impact may allow only bladders a particular distance from the site to inflate. Depending on the type of wound, multiple regions can be inflated, for example in case of a full penetration, the regions close-by the entrance and exit site of the wound can be pressurized. Also, in the event of a major tissue destruction, for example, losing a limb, e.g., due to a bomb blast or a shark attack, the device can build up a "ring of pressure points" to act as a tourniquet, and/or to create a watertight seal. If used, for example, in a diving or immersion survival suit, the system may inflate the upper body section in case of emergency, to provide buoyancy.

In case of a manual override of the system (which may be achieved by pulling the rip cord, and/or by using the external inlet valve), all bladders may be inflated, which will apply pressure throughout the system, thereby gently restricting the movement of the user, and stabilizing the body.

Air Pump

In some embodiments, the devices of the invention may include an air pump. By "air pump" is meant any device capable of pushing air. For example, centrifugal or positive displacement pumps. Centrifugal pumps produce flow by increasing the velocity of gas with a rotating vane impeller. Types of centrifugal pumps include radial, axial, and mixed flow. Positive displacement pumps operate by alternating of filling a cavity and then displacing a given volume of gas. Positive displacement pumps deliver a constant volume of gas for each cycle. Types of positive displacement pumps include reciprocating pumps (piston, plunger, and diaphragm), power pumps, steam pumps, and rotary pumps (gear, lobe, screw, vane, and peripheral and progressive cavity. Examples of air pumps that may be used in the devices of the invention include, but are not limited to, pumps such as the Lightweight Mini Air Pump (Kent International, Parsippany, N.J.), the Magic Air 12V Inflator/Deflator (Metro Vacuum, Oakland, N.J.), and the Stansport 12V Electric Air Pump (Stansport, Los Angeles, Calif.).

Pressurized Medium Container

In some embodiments, the devices of the invention include a pressurized medium container, such as a compressed gas cartridge. It may be attached to the wearable device and "communicates" to the layers of the device (i.e., compression and sealant layer) through a cartridge actuation mechanism and an inflation tube. The cartridge actuation mechanism includes a triggering device that may be actuated to open the cartridge by means of an actuation lever. The actuation lever actuates the triggering device in response to a force of predetermined magnitude, and in doing so detaches from the actuation mechanism. Upon triggering the actuation mechanism, the cartridge will open which allows the gas/compressed medium from the cartridge to inflate the compression/buoyant layer. The system is preferably provided with a deflation tube and a deflation valve.

Figure 19:
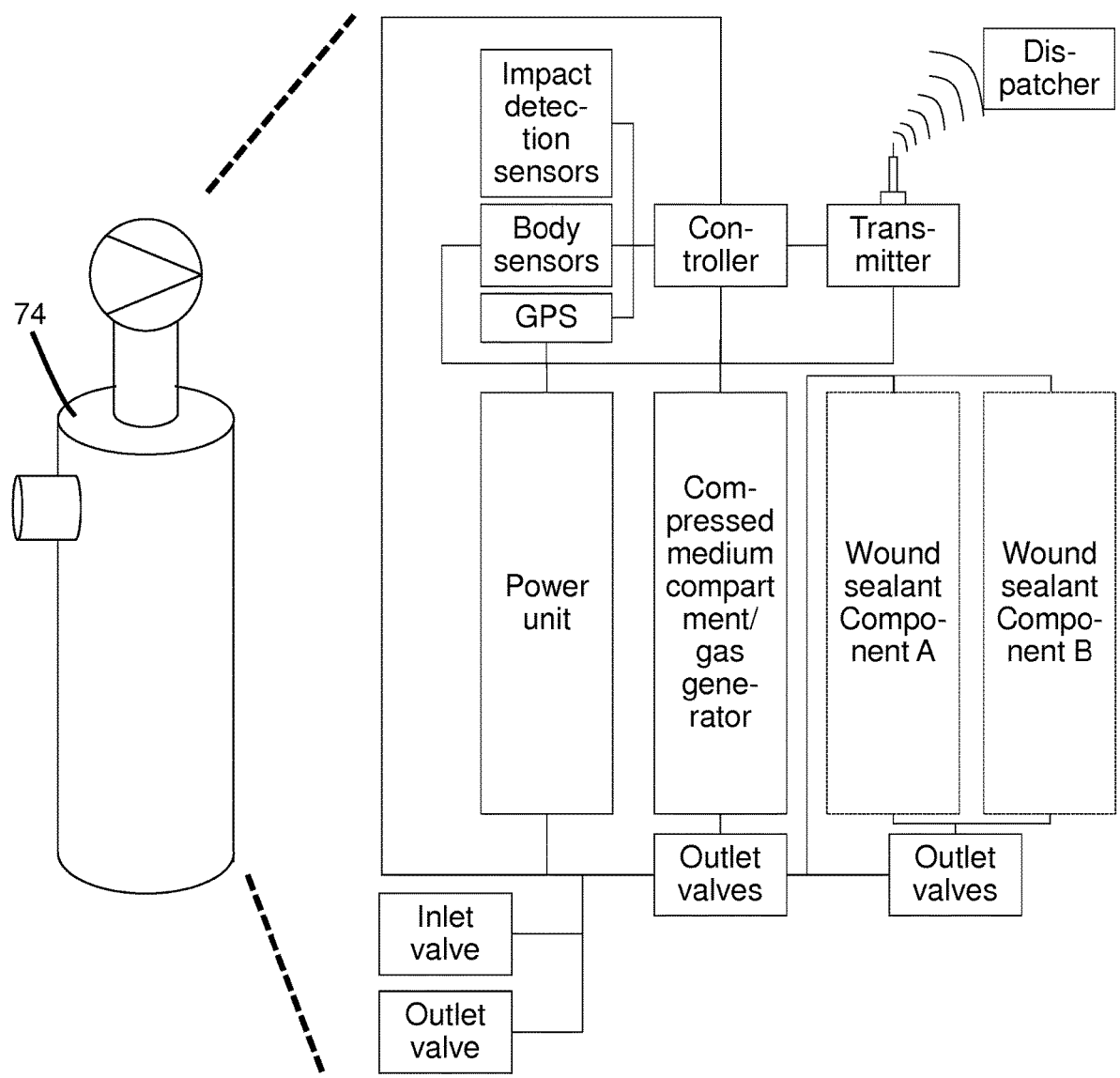
FIG. 19 is a schematic showing an illustrative view of a central unit and its components including a 2-component wound sealant system.

As shown in FIG. 17 and FIG. 19, the device is provided with a source of compressed gas for triggering the sealant flow and inflating the compression layer. In a preferred embodiment, the compressed gas source includes at least one compressed $CO_2$ gas cartridge, and preferably two such cartridges, as shown. Each cartridge may be removably secured within the central unit. Alternatively, the cartridge may be secured by a fabric loop fastened to the device. The gas cartridges may be of conventional design, and are commercially available from a number of sources. While such cartridges come in a variety of sizes, two cartridges, each of the 16 gram net contents weight size may be used in some embodiments of the invention.

As shown in FIG. 11, each cartridge may be removably coupled (as by a threaded fitting, not shown) to a cartridge actuation mechanism. The actuation mechanism may be of conventional design, and are commercially available from a number of sources. For example, if 16 gram cartridges are used, the actuation mechanism may be the Model 840AM, (Halkey-Roberts, St. Petersburg, Fla.), or the equivalent. The actuation mechanism may include a triggering device that comprises an actuation lever that is detachably connected to a spring-loaded pin or rod (not shown), installed in the actuation mechanism to rupture the neck of the cartridge when the lever is pulled with a force of predetermined magnitude, thereby opening the cartridge. The cartridge may be connected to inflation tubes and valve arrays, which direct the flow of gas to the sealant layer and the bladder system. When a cartridge is opened, as described above, gas from the open cartridge may pass through its associated inflation tubes and valves into the interior of the sealant compartment to trigger the sealant flow, and into the predetermined bladders to inflate them.

Gas Generator

In some embodiments, the devices of the invention may include a gas generator (instead of or in addition to the previously described compressed medium container), comprising a precursor for generating gas (e.g., carbon dioxide, nitrogen, hydrogen, oxygen, or other non-flammable and/or inert gas) to trigger the sealant flow and/or the inflation of the bladders in the compression layer at a temperature which does not damage the human body or the human skin. Examples of gas generating agents are described in PCT Publication No. WO2012141578 for use in a wearable assembly for providing a rescue function, such as buoyancy. Also this type of generator is disclosed in PCT Publication No. WO 03/009899. In this reference the generation of gas is aimed at providing oxygen to for instance divers or for the purpose of driving rocket engines.

By applying a gas generator comprising a precursor for generating gas, an assembly can be provided wherein the gas generator can be given a relatively compact form compared to other volume-generating means. A cool gas generator (i.e., one that operates at or near room temperature) may be able to provide a high gas volume relative to the size, weight and/or volume of the gas generator. A further advantage of such a gas generator is that it can be stored for a long period, (e.g., up to 10 years or longer), after which period it still functions, and can be activated in the usual manner. This is advantageous since it enhances convenience of use, compared for instance to systems with CO2 cartridges based on expansion. Such systems require a one, two, or three yearly check, or replacement, of working parts. The operational principle of generating gas from a precursor is known for the purpose of providing a propelling action, such as for rocket engines or in the aerospace industry.

In a further preferred embodiment a low reactivity or inert gas is generated under operating conditions, such as nitrogen or carbon dioxide or other non-flammable and/or inert gas, or moderately reactive gases are generated, such as oxygen or hydrogen. Examples of precursors used include, but are not limited to, alkali metal chlorates and alkali metal perchlorates, in particular lithium perchlorate ($LiClO_4$), lithium chlorate ($LiClO_3$), sodium perchlorate ($NaClO_4$), sodium chlorate ($NaClO_3$), potassium perchlorate ($KClO_4$) or potassium chlorate ($KClO_3$), peroxides, in particular sodium peroxide ($Na_2O_2$) and potassium peroxide ($K_2O_2$), superoxides, in particular potassium superoxide ($KO_2$) and sodium superoxide ($NaO_2$), and others known in the art.

In a further preferred embodiment the gas generator comprises gas-forming substances which can preferably be actuated by means of mechanical or electrical energy. An automatic actuation of the process of forming a gas can hereby be started. In a further preferred embodiment the initiation assembly in the gas generator comprises biasing means, such as a spring, and/or by electric means, and/or biasing means release means, such as a soluble tablet.

In a further preferred embodiment the gas generator acts as a pump, like devices available by Sensidyne, St. Petersburg, Fla. (e.g., Sensidyne Diaphragm Micro Air Pumps) and Schwarzer Precision, Essen, Germany (e.g., Rotary Diaphragm Pumps), generating enough pressure and volume to inflate the bladders, or if used for liquid, to transport the sealant to the required location.

The automatic actuation of the gas generator is hereby realized in a manner easily understandable to the user.

The "Central Unit"

The "central unit" 74 may house one or all of the following items: Pressurized medium container/gas generator 98, wound sealant reservoir(s) 100, information processing unit/controller 102, sensors, GPS unit 104, the data transmitter unit (and emergency beacon) 106, valve array 108, manual valve inlet 88, manual inflator, energy source 96, connectors, e.g., connectors for data and energy transfer.

If desired, the individual components may be placed and embedded in another location on the unit, which may increase the safety and comfort level of the user, e.g., the pressurized medium container may be separately attached to the vest, away from the controller).

Once the impact layer registers an impact, the information processing unit will determine the location and severity of the impact, and trigger the activation of the gas generator and/or the release of the pressurized medium, and, optionally, the activation of the emergency beacon and data transfer (e.g., the GPS location). The system determines which valves will be activated, to direct the pressurized medium to the bladders closest to the site of the wound. It may also pressurize the sealant layer, to have the sealant flow towards the site of destruction.

In case of malfunctioning of the electrical system, one can trigger the opening of the main valve manually via a rip cord (or similar). This may also be done to inflate all bladders, to restrict body movements, e.g., for transportation purposes. In case of malfunctioning or damage of the compressed medium container, one can manually trigger the flow of the wound sealant and the inflation of the bladders via an additional inlet valve, which can be used as an inlet for inflation by pump or by mouth.

Information Processing Unit

In some embodiments, the devices of the invention include an information processing unit 102. It may also include one or more of a controller, a programmable memory, and/or a data storage system (e.g., a flash memory system) which can be used to record data from sensor inputs. The unit processes the signals received from the impact detection layer, and other sensors (if incorporated), such as temperature sensors, moisture sensors, and pressure sensors. Depending on the outcome of the computation in interaction with the program stored on the memory, the unit may then determine to activate the gas generator (if available), and to open the valves, which closed off the compressed medium container, and open further relevant valves of the system in order to direct the flow of the sealant to the site of the wound, and to inflate the bladders in that region. The unit may also determine the need to inflate certain other areas, (e.g., in order to provide for an increase of buoyancy forces to keep a user afloat that was injured while in or by the water). The information processing unit may also trigger the transmission of data (such as a distress signal) via the data transmission unit. The information processing unit may be incorporated into the "central unit". As for all electrical parts of the entire system, it may be powered by the energy unit, and may be housed in a "weather-sealed" compartment in order to be protected from the environment.

GPS Unit

In some embodiments, the devices of the invention include a GPS unit 104. The GPS unit may be incorporated into the "central unit" or integrated into the previously described layers of the invention, preferably at a position where a GPS signal can best be received. The unit may be integrated in a "weather-sealed" compartment and be powered by the energy unit. The GPS sensor may send its data to the information processing unit.

Other Sensors

In some embodiments, the devices of the invention may include other sensors, such as sensors for measuring the temperature, moisture level, pressure, acceleration, and vital information, such as heart rate, blood pressure, or similar. If used with vehicles or machines may also include sensors for speed, oil pressure, and altitude. The sensors may be powered by the energy unit, and may send their data to the information processing unit.

Certain implementations of this aspect of the invention provide that: physiological sensors are attached to the device, and are operably engaged to the wearer for generating physiological signals corresponding to selected physical conditions of the user; the distress signal may include information corresponding to the physiological signals; the physiological sensor may be a thermometer for measuring the body temperature of the user and the distress signal may include information about the body temperature of the user; the physiological sensor may be a blood pressure meter for measuring the blood pressure of the user and the distress signal may include information about the blood pressure of the user.

Valve System

In some embodiments, the devices of the invention include a valve system 108. The valves may be designed for wet and dry application and may connect the compressed medium container, and or the gas generator to inflation tubes, to the sealant compartment, and/or to the bladders in the compression/buoyancy layer. In some embodiments, the device includes mainly one-way valve systems. The valves may be electrically activated to allow for a flow of medium (e.g., gas or liquid). They may be powered by the energy unit, but may also be engaged manually. In case the previously described actuation mechanism is triggered manually by pulling a rip cord, the valves directing the flow towards the sealant compartment and the bladders, will turn to an "open" position (one-way), and thereby allow for the inflation of the entire compression layer.

Manual Triggering Mechanism

In some embodiments, the devices of the invention include manual triggering mechanism 112. In case of malfunctioning of the electrical system, or if a manual override of the system is desired, one can trigger the opening of the valves manually via a rip cord (or similar). A manual override may lead to inflation of all bladders, e.g., to restrict body movements for transportation purposes. It may also initiate the flow of the sealant to the site of destruction. The triggering mechanism may be the Model 840AM (Halkey-Roberts, St. Petersburg, Fla.), or the equivalent.

In case of malfunctioning or damage of the compressed medium container, one can manually trigger the flow of the wound sealant and the inflation of the bladders via an additional inlet valve, which can be used as an inlet for inflation by pump or orally.

Inlet for Manual Inflation

In some embodiments, the devices of the invention include an inlet for manual inflation 88. In case of malfunctioning of the pressurized medium system, or the gas generator, one may manually inflate the bladder layer and pressurize the wound sealant layer compartment. This can be done by using an external pump, or by orally "blowing" into the inlet valve. Examples of this type of component may be the model V73000 (Halkey-Roberts, St. Petersburg, Fla.), a breather tube and relief valve with dust cap, which is designed for applications requiring oral filling and pressure relief for overpressure protection, or the equivalent.

Data Transmitter Unit

In some embodiments, the devices of the invention include a data transmitter unit 106. When the device receives an impact, electrical contact is broken between the leads and the transmitter is activated to send a digitally recorded message, which may include the vest's serial or identification number, and/or information on the wearer and his location. Preferably, the transmitter is used in conjunction with a base relay unit, such as a car radio. Therefore, the transmitter serves as a means for notifying others that the user has received an impact. The transmitter may be activated by the apparatus receiving and sensing an impact. The transmitter may be powered by the energy unit. One may use for example a device based on the description in U.S. Patent Application No. 20030107516, or U.S. Pat. No. 6,285,318, or PCT Publication No. WO2001084174, each herein incorporated by reference in its entirety. Also, commercially available miniature personal locator beacons, such as, the Satellite Messenger (SPOT LLC, Milpitas, Calif.) may be used. In some embodiments, the data transmitter transmits to a visual readout such as a monitor (e.g., a computer monitor) or a smartphone.

Energy Source

In some embodiments, the devices of the invention include an energy source 96. For this, rechargeable energy accumulators, comprising of one or more electrochemical cells may be used. Preferably light weight units with high energy-to-mass ratio are preferred, e.g., lithium ion based rechargeable batteries. The energy source may be integrated into the central unit housing or be attached at another location of the device and attached by wires or leads to other components of the device. The energy source may provide power to any component of the device, e.g., the inflation system, one or more impact detection sensors, one or more triggering mechanism, the sealant system, one or more information processing units, an amplifier, a controller, a memory system, a GPS unit, a data transmitter, or other sensor.

Figure 15:
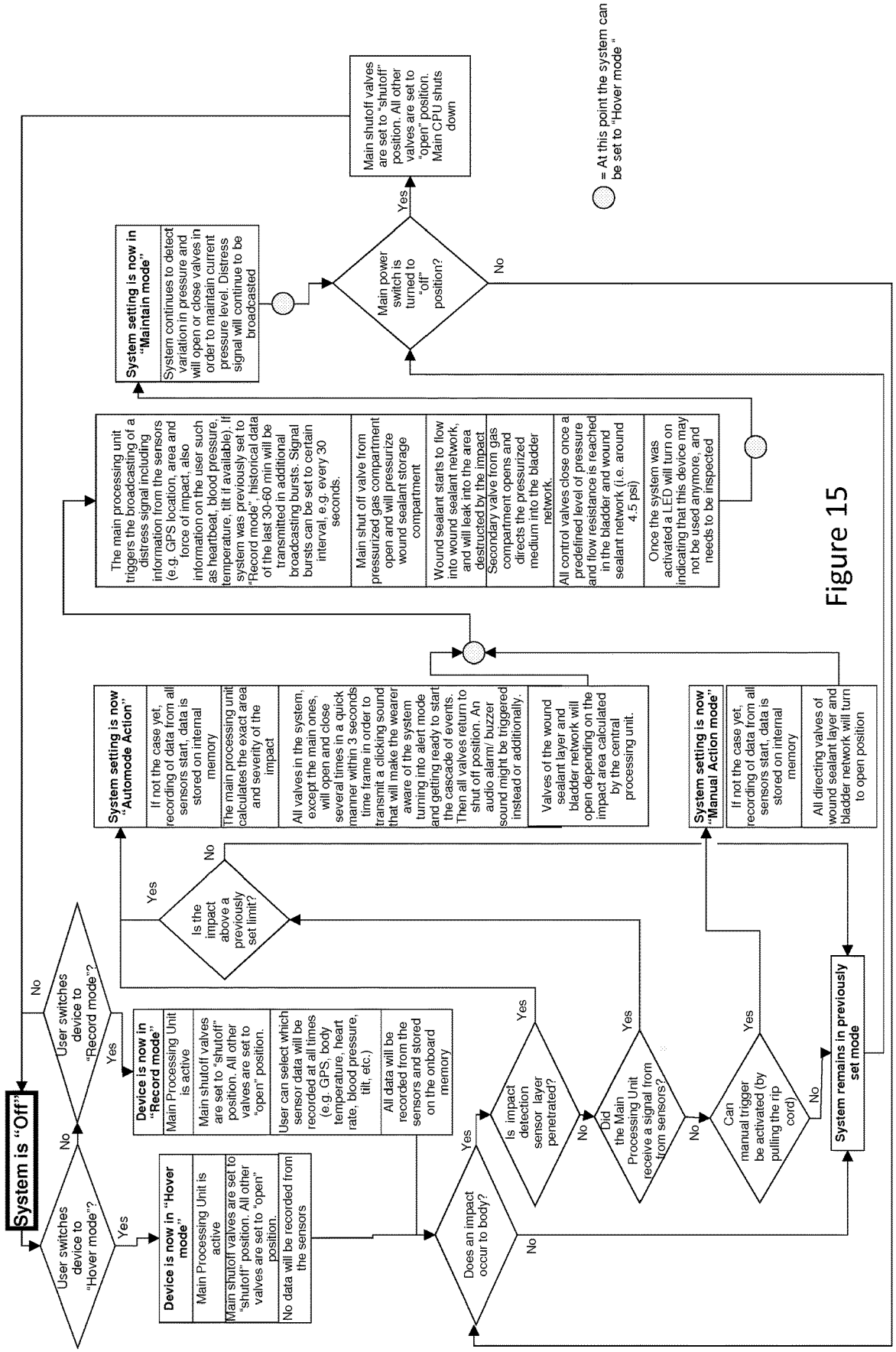
FIG. 15 is flowchart that illustrates an example of a cascade of events that may occur when using a device of the invention.

The energy source can provide power to the device for one or more days (e.g., 1-10 days or more) when in an inactive or monitoring state (e.g., the unit is turned off or in hover or record mode) or for one or more hours (e.g., 1-10 hours or more) when in an active state (e.g., auto action mode, manual action mode, or maintenance mode; see FIG. 15).

The device may also include a solar array for recharging the energy source (e.g., a rechargeable battery).

Connector for Data and Energy Transfer

In some embodiments, the devices of the invention include a connector for data and energy transfer. The connector may allow for wired and or wireless transfer of data and energy (to recharge the energy accumulators), and to connect to other devices and external computing units. The connector may transfer all types of information that were accumulated over a certain period of time (and stored on the onboard memory), but also allow for a "live" view, i.e., a reading of all the sensor signals in real-time. Also, the transfer connector allows access to the on-board controller and memory, for read and write actions (e.g., to update the on-board program).

Outer Layer

The outer layer may be made out of a durable material, such as a polymer mix, cloth (such as cotton, wool or others), leather, or any material described for use with the inner layer of the devices of the invention. It may also include next generation materials, such as nano-fiber based garments. It has to be designed in a way that it supports the build-up of pressure on the body, upon inflation of the bladders. Also the garment may be designed to allow for a certain "stretch". The outer layer also protects the inner layers from environmental influences. Depending on the overall design, the layers can be directly integrated into a garment or protective clothing (body armor, diving suit etc.).

Also, if desired, the outer garment may be chosen, to act as body armor itself, e.g., it may be made out of high performance fibers, which offer ballistic protection. Examples include products from Kevlar, but also new materials such as artificial spider silk, nanocomposites, and carbon fiber woven from carbon nanotubes. In one embodiment, the device may also include pockets, to hold hard armour plates/ballistic plates.

The outer layer may include straps, hooks, clips, zippers, velcro elements or similar, to allow for an easy adjustment and tightening of the device to the body of the wearer.

While it will be apparent that the preferred embodiment of the invention herein disclosed is well calculated to fulfill the objects above stated, it will be appreciated that the invention is susceptible to modification, variation and change without departing from the proper scope or fair meaning of the subjoined claims.

The present embodiment of the invention is not intended to be limited to only those items illustrated herein, but rather, includes items which are known in the art and are not necessary for understanding the present invention. Therefore, the drawings have been simplified to eliminate many of the known electrical and transmitting components associated with the apparatus.

Cascade of Events

FIG. 15 illustrates the cascade of actions that will happen, once the system is triggered. In its simplest automated variant, the device can be set to "hover mode" or "record mode" when switched on. In "hover mode" the system will detect any impact to the wearer, and will trigger all necessary following actions, but will not record any data from the sensors upon an impact. Sensory data may include the GPS position of the device, and other data about the wearer's condition, such as temperature and pulse rate. "Hover mode" will minimize the electrical power consumption significantly, as only the processing unit and the impact detection layer are active. In "record mode", the device will record data from all previously selected sensors. It may also transmit data on a continuous basis. The power consumption may be significantly higher than in "hover mode".

Once an impact to the impact detection layer occurs, is detected by the main processing unit, and is above a certain threshold, the processing unit would switch the system into "auto action mode". In this mode, the processing unit calculates the impact area and severity, and opens all required valves in this area. An audio signal/buzzer sound/vibration may be triggered to alert the user that the system will start the cascade of following steps. The user may stop this cascade at any time (e.g., by hitting a certain defined area, such as the chest) repeatedly (e.g., three times). The system will recognize this and immediately stop all events, and go back to its previous mode setting. The device can be deflated (if already inflated) by this in a very simple manner.

After the signal (sound or vibration) occurs, the cascade of the following steps will take place:

Data from all sensors will be recorded (if not already done so), and broadcasted automatically with a distress signal.

The main valve 89 directs the pressurized gas into the wound sealant container, which will flow to the site of the impact, and cover the wound. The main valve then starts directing portions of the pressurized medium to the bladders at the site of impact and will pressurize them to a previously determined point. Once a previously defined point of flow rate, volume and pressure is reached, the system will switch to "maintain mode", in which it will maintain the previous set-points of pressure levels until the system detects another impact, or is set back to its initial mode (i.e. "hover mode"

or "record mode"), e.g., hitting the chest three times, or is turned "off". Once the cascade of steps has been initialized, the system will record this event, and signal it, for example, by a red LED light, which signalizes the user, that maintenance on this unit is required. A signal will also occur after a certain usage period, or if power level is low.

In case the processing unit, or the sensors were malfunctioning and never detected a signal triggered by an impact, the user may manually trigger the system, for example, by pulling a rip cord on the outside of the unit. This will set the system into "manual action mode". Once triggered, the system will record all sensory data, open up all directing valves of the wound sealant and bladder network follow the cascade of steps, mentioned above for "auto action mode".

Other Embodiments

In addition to the features and components described above, devices of the invention can also include components that enable or provide signal transfer, data transmission, heart rate monitoring, respiratory data monitoring, body movement monitoring, GPS, hemorrhage control in the extremities and/or trunk, buoyancy, environmental data (e.g., pressure, wind speed, humidity), and autonomous action.

EXAMPLES

The following examples are to illustrate the invention. They are not meant to limit the invention in any way.

Example 1

A military or law enforcement person encounters a hostile situation and is hit by a fragment. The fragment(s) penetrated the body armor and created hemorrhage. The wounded person might move into a shock state and loose conscience. The accompanying partner is returning fire and is unable to immediately assist. The wounded person is wearing the invention as a jacket underneath his OTV (Outer tactical vest). The impact detection layer registers the impact and immediately triggers the wound sealant to be delivered to the site of the wound (to the entrance and exit wound), and the pressure layer starts building up pressure in that same area, to restrict the loss of blood. In case multiple hits to the wearer occur, the system will respond in the same manner.

Also, at the same time an encrypted emergency beacon signal identifying the unit and the location (and the status of the injured) is transmitted to a friendly post, an army or police station, or similar.

In order to transport the wounded person to the closest medical emergency facility, the partner decides, to manually inflate the entire suit of the wounded person, in order to stabilize the body. For this, the partner pulls the ripcord, which is attached to the outside of the unit. The full body suit inflates, and stabilizes the wounded person.

Once emergency medical care can be delivered to the injured, the care taker presses the emergency release button on the side of the suit, to deflate the unit, and then takes it off the person, to treat the injury.

Example 2

A prison guard is stabbed during a riot outbreak. The person is wearing a "vest-version" of the device. The unit detects the penetration of the layers and activates automatically the flow of wound sealant to the site of the wound, the pressurizing of the area, and the broadcasting of an emergency signal. The central control room receives the distress signal, and sends in medical personnel to assist.

Example 3

A diver encounters a life threatening situation during a shark attack, when losing a limb, and starts to faint. The diver is wearing a full body suit, which has the multi-layer device integrated. The impact detection layer detects the massive destruction at the limb and immediately pressurizes the area circularly from all sides, to act as a tourniquet, and decrease the blood loss. At the same time the bladders around the diver's shoulders and the upper part of the body will inflate, in order to increase the buoyance forces, and to raise the diver to the water surface.

Example 4

An inflatable boat uses an integrated version of the device as an additional "skin". The site of the boat is damaged in an ongoing storm. The impact detection layer senses the area of destruction and delivers a foam sealant for bonding and gap filling purposes to this site, while the bladders increase in size and apply pressure to the opening site. In conjunction with the sealant, which bonds to the boat's wall material and the bladders, the bladders seal off the site of destruction. Depending on the damage that occurred, an emergency beacon signal gets released.

Example 5

The device is integrated into an oil tank unit. During a blast, fragments penetrate the oil tank wall. The device detects the impact and uses a non-flammable and oil resistant sealant to seal off the penetrated site while bladders generate a pressure to keep the site closed off.

Example 6

Cardiopulmonary resuscitation (CPR) is an emergency procedure for manually preserving brain function until further measures to restore spontaneous blood circulation and breathing in a person who is in cardiac arrest. It is indicated in those who are unresponsive with no breathing or abnormal breathing, for example, agonal respirations.

Per the International Liaison Committee on Resuscitation guidelines (as of 2010), CPR involves chest compressions at least 5 cm (2 in) deep and at a rate of at least 100 per minute to pump blood through the heart and thus the body.

In this example a person is wearing the device as a vest, which also includes a position and motion and pressure sensors and a pulse meter. The wearer of the device collapses due to heart failure. The device automatically senses the critical condition of the user, triggers the transmission of an emergency signal and the inflation-and-deflation-cycle for the chest compression (in accordance with current CPR guidelines).

In an alternative example of a military personnel on the battlefield who encounters an individual heart failure, the device can also be triggered when a conventional CPR is performed on the wearer. Once a fellow soldier starts performing CPR, the device detects the (external initiated) chest compressions and activates the automated compression cycle, so that the helping soldier can stop performing compressions and is "freed up" to focus on providing additional oxygen to the person and to continue defending the position until support arrives, if necessary.

The chest compression cycles are monitored by the on-board controller, which also controls the airflow and pressure of the integrated miniature air-pumps, and the position (open/close) of the valve-arrays. The electronics, sensors, air-pumps, and valves may be powered by an integrated power source.

Once the device detects a pulse of the wearer and/or becomes manually disengaged, the compression cycles stop.

Example 7

Massage Therapy is essential in the management of tight muscles, aiding circulation, avoiding blood clots, and overall relaxation. Especially people with disabilities benefit greatly from a wearable device that can give automated massages.

In this example, a wheelchair user paralyzed from the hip down to his feet, wears pants which have an integrated network of feeding tubes, multiple valves and bladders, a micro air-pump, and a controlling unit. The unit can be programmed to trigger a series of inflation and deflation cycles at different locations of the pants, to generate localized areas of pressure changes thus enabling the massaging of the wearer's extremities. The same approach can be used for integrated jackets, which can perform massaging procedures of the upper body.

In another example the device can be wrapped around extremities (i.e., it is not worn constantly, but rather placed on top of normal clothing when desired). The device can be fixated via hook-and-loop fastener and then be activated for massaging purposes when desired, e.g., for passengers on long flights to avoid blood-clotting complications such as deep vein thrombosis (DVT) and pulmonary embolism.

The device can also be used to provide post-surgical massage, e.g., to the extremities (e.g., the lower legs) in order to avoid the formation of blood clots. Devices of the invention that provide massage therapy may be configured to provide oscillating pressure (e.g., by repeated filling and deflating of the bladders, such as in random order, in an ordered sequence, or by substantially simultaneous inflation and/or deflation of the bladders).

Example 8

The device in this example is similar to the one described in Example 7. Due to the multiple bladder arrays throughout the wearer's device, pressure points can be generated throughout the entire device, creating a unique touch-like feeling on the wearer's body.

In Example 7 this capability may be used to massage the user, giving the user the control over position, strength and motion of the pressure points. In this example, another user transmits signals that the device controller translates into pressure points, mimicking for instance someone's touch, or an impact, e.g., in virtual reality and haptic teleoperation.

Example 9

The device in this example is similar to the one described in Example 7 except the bladders are integrated into a device which functions as a breast pump (e.g., a device configured as a single breast pump, a double breast pump, or incorporated into a bra-like garment). Once the impact detection layer senses a pressure change, or is manually triggered, the bladders will inflate to contact the skin. The device can be configured to perform a massage of the breast (e.g., by providing oscillating pressure (e.g., by repeated filling and deflating of the bladders, such as in random order, in an ordered sequence, or by substantially simultaneous inflation and/or deflation of the bladders)). The device can also be configured to provide a low vacuum that creates a mild suction to retrieve the breast milk, which is then collected into an external container.

Example 10

The device in this example is similar to the one described in Example 7 except the bladders are integrated into a blood pressure cuff for use in a blood pressure monitor. Once the impact detection layer senses a pressure change, or is manually triggered, the bladders will inflate to create the necessary pressure to measure blood pressure using, e.g., one or more sensors capable of detecting blood pressure (e.g., a manometer). The bladders are subsequently deflated and the blood pressure is reported, e.g., using a visual readout, to the subject.

Example 11

In this example the inflatable layer of device is used within a fashion and art setting to allow for creating visual effects by inflation and deflation of certain or all segments of the device. For a show performance one can envision for example a costume like suit, that inflates and deflates segments in accordance to the music playing in a fashion that make it look like waves running all over the body.

Example 12

Figure 20:
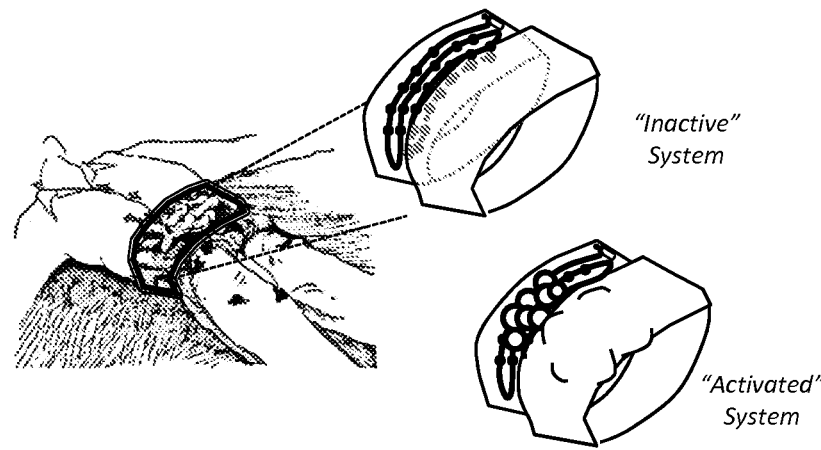
FIG. 20 is a schematic showing a cut-away view of a device of the invention configured for use as a wound dressing. The inset shows an exploded view of the device in inactive and active forms. The device shown can also be used for stabilizing a patient during transportation (e.g., to a hospital) and as compression wear (e.g., as a suit for patients with orthostatic intolerance).
Figure 20:
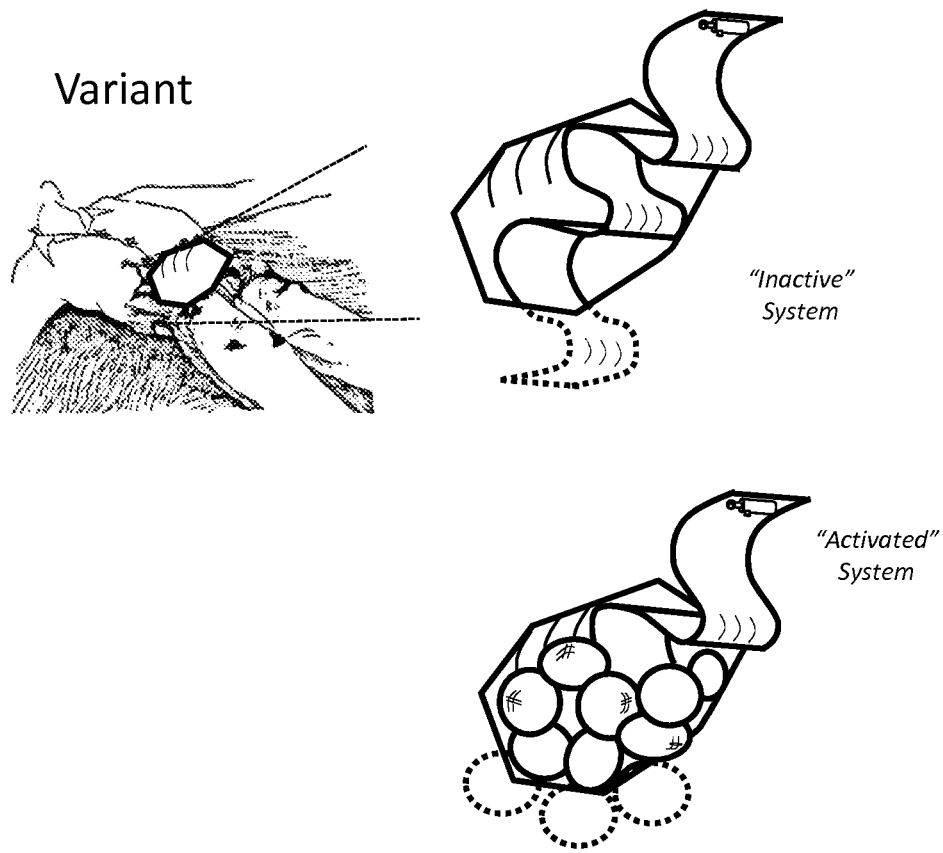

A device of the invention may also be configured for use as a wound dressing. In this configuration, the device may be applied to a person who has received a traumatic injury to the trunk that results in uncontrolled bleeding (see FIG. 20). Activation of the device applies pressure to the injury and slows the bleeding.

Figure 21A:
FIGS. 21A-21C are photographs depicting a device of the invention.
Figure 21B:
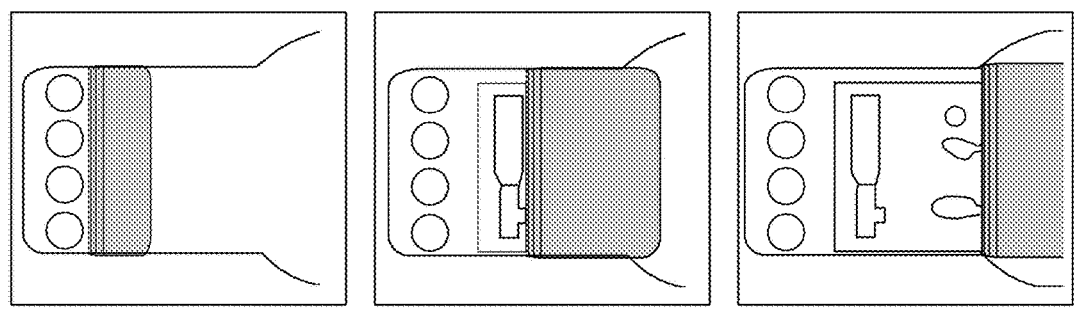
Figure 21C:
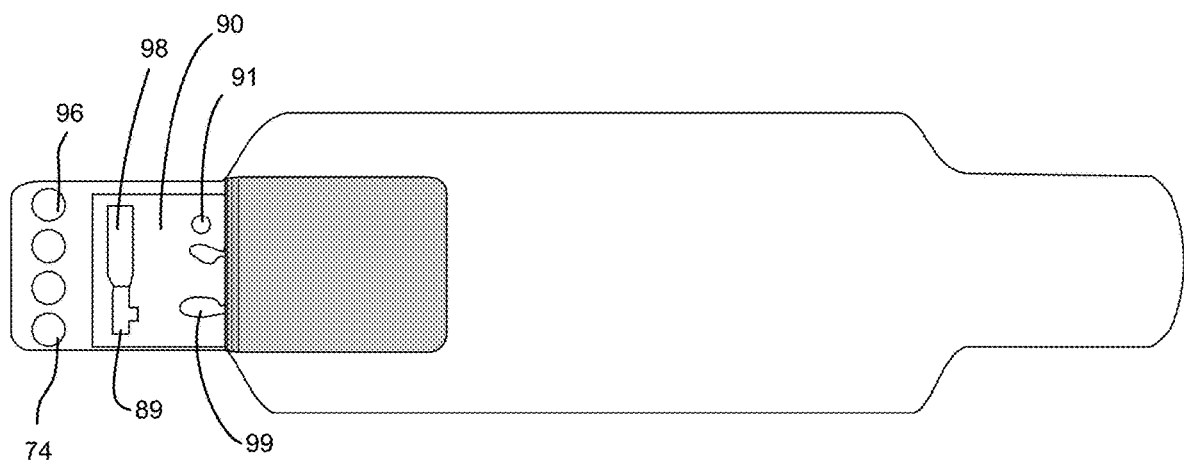

As shown in FIGS. 21A-21C, such a device of may include an energy source 96, a pressurized medium 98, pressure sensitive conductive fabric 90, a piezo-electric impact detection layer 91, a micro-inflatable compression layer bladder network 99, main valve system 89, and a Central unit 74 (including a transmitter for wireless data transmission and communication). This device may be worn, e.g., as shown in FIGS. 22A-22H.

Example 13

Figure 23A:
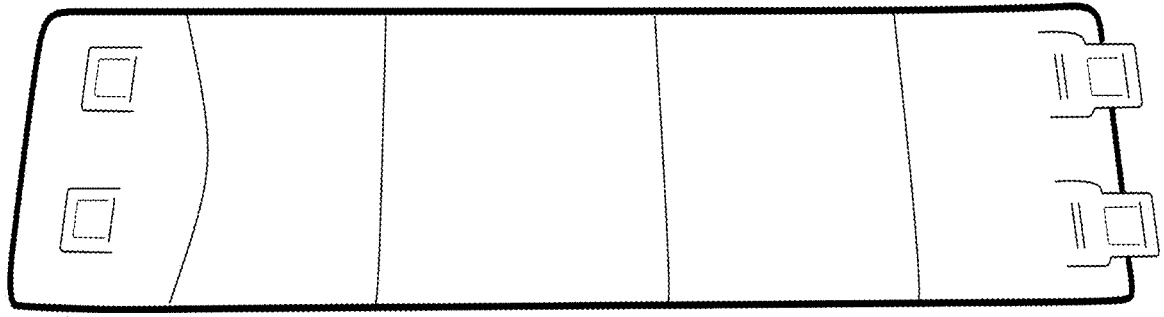
FIGS. 23A-23D are images depicting an experimental setup showing functioning of a device of the invention.
Figure 23B:
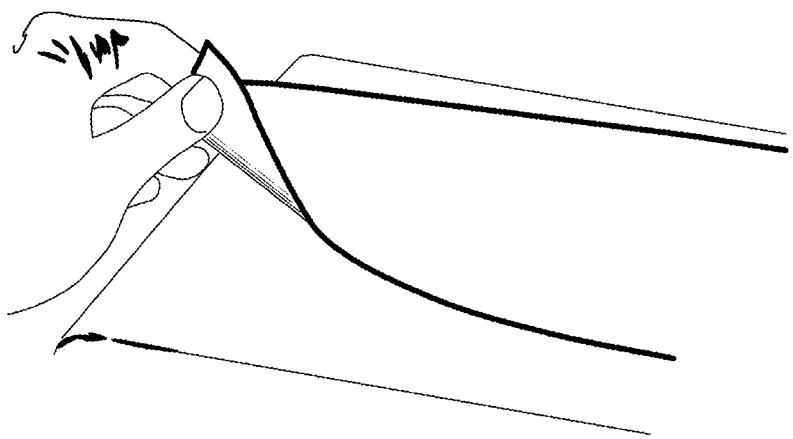
Figure 23C:
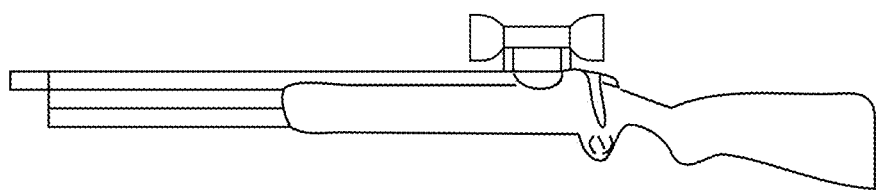
Figure 23D:
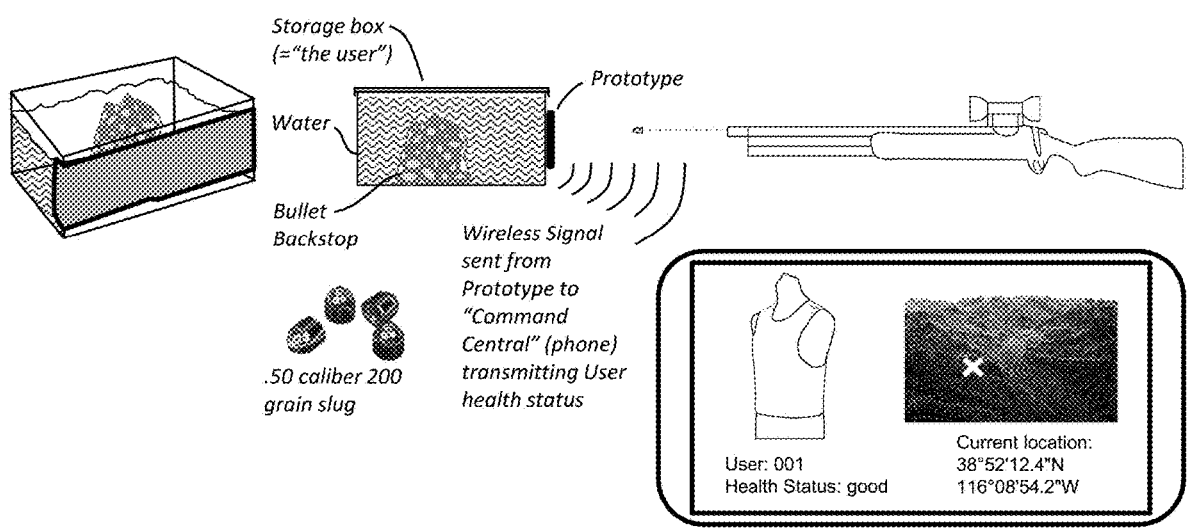

A device of the invention has been tested for its ability to activate in response to an impact and to control "hemorrhage" resulting from the impact. In the experiment, a prototype system is mounted to the outside wall of a clear polymer storage box (representing the "user"), which is filled with water and a bag of stones; the stones act as a bullet backstop (see FIGS. 23A and 23B). A .50 caliber rifle shooting 200 grain slugs at 900 FPS (FIG. 23C) is set up at a distance of 10 feet. The system is active and wirelessly transmits in regular intervals user information to the "command central", in this case, an android based cellphone (FIG. 24D). The information transmitted includes biometric user data retrieved from the body sensors, which measure heart rate, blood pressure, body temperature and the user's GPS geo-location information.

Figure 24A:
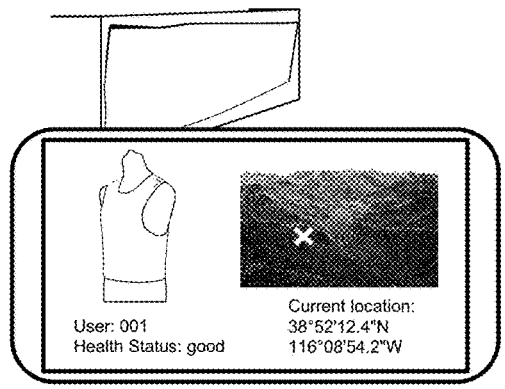
FIGS. 24A-24E are photographs showing time-lapse capture demonstrating the functioning of the device shown in FIGS. 23A-23E.

A demonstration of the system was carried out as shown in FIGS. 24A-24D):

As shown in FIG. 24A, the system indicates that the device is active and transmits health status (from body sensors) and geo-location of user wirelessly to "command center".

Figure 24B:
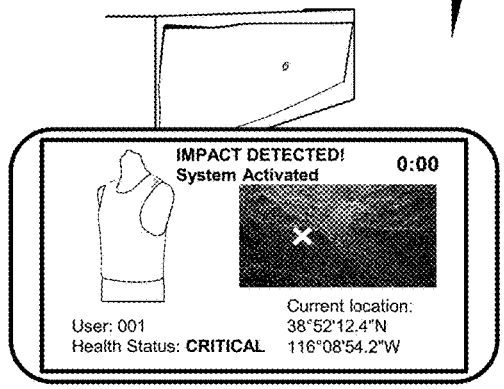

As shown in FIG. 24B, the impact of the rifle slug hitting the target produces a hole that begins to leak water from box. The impact also activates the system. Detection of the impact by the system sends out a distress signal, incl. user's health status and location.

Figure 24C:
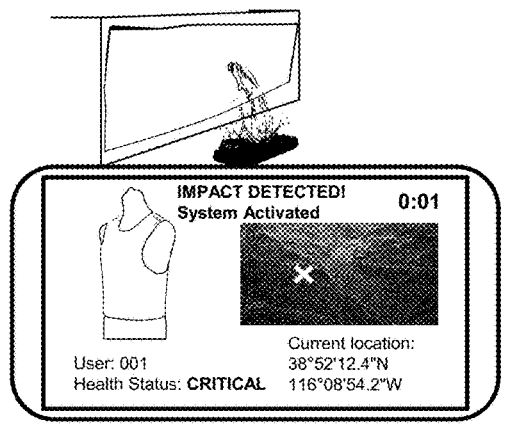
Figure 24D:
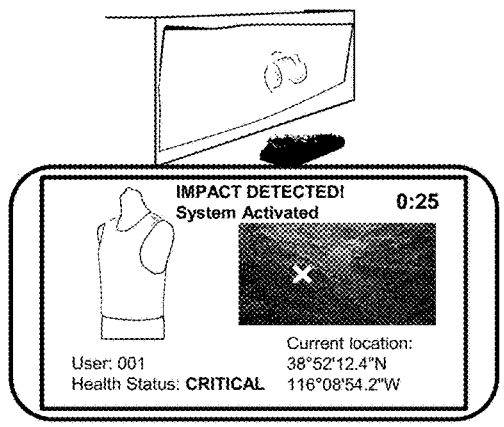

As shown in FIG. 24C, the system activates the hemorrhage control layer and starts closing up the "user's wound site". The distress signal continues to be sent out.

As shown in FIG. 24D, the "external hemorrhage" (i.e., water flow) stops after 25 seconds. The distress signal continues to send out updated information on the user's status.

Figure 24E:
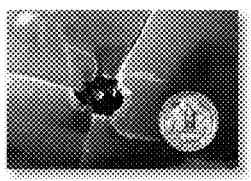

FIG. 24E shows the impact site and the size of the hole created.

Figure 25:
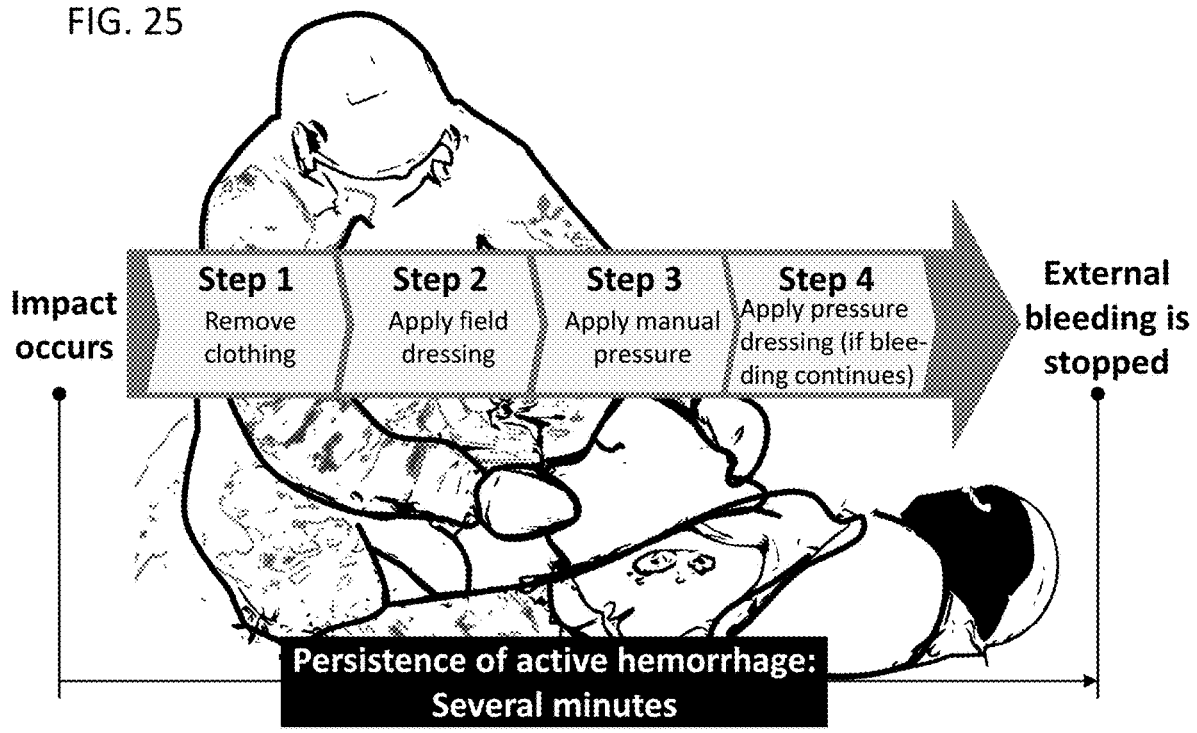
FIG. 25 is an image showing that combat treatment according to the Conventional Manual Procedure for Combat Casualty Care (Field Manual Apr. 25, 2011) requires several minutes before active hemorrhage is under control and may require the assistance of additional personnel (e.g., "Buddy Aid").
Figure 26:
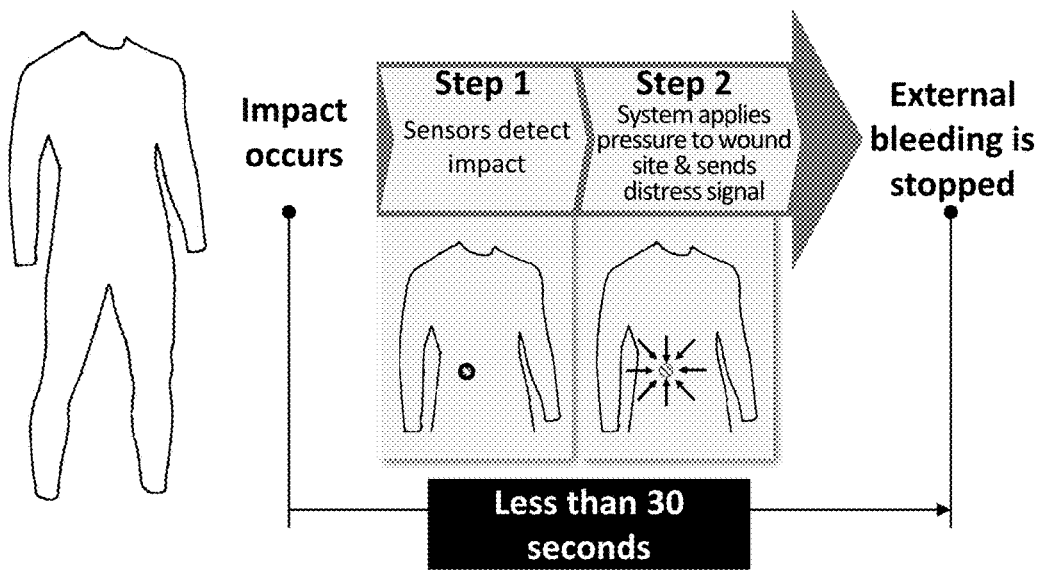
FIG. 26 is an image showing that a device of the invention is capable of controlling external bleeding within seconds (e.g., 30 seconds or less) and is fully automated.

As demonstrated by the experiment, a device of the invention can be used to stop "external hemorrhage" in less than 30 seconds, autonomously and automatically. Compared with standard first aid, this is a significant decrease in persistence of the hemorrhage (see FIGS. 25 and 26).

All publications, patents, and patent applications mentioned in the above specification are hereby incorporated by reference. Various modifications and variations of the described device and methods of use of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

The invention claimed is:

1. A wearable garment configured to be worn on a body of a mammal and comprising a front part and a back part, wherein the garment comprises an impact detection device on the front part comprising:
   (a) a first layer comprising an array of impact detection sensors defining at least first and second non-overlapping regions that are configured to independently activate upon an impact thereto; and
   (b) a second layer adjacent to the first layer comprising two or more bladders, each of said bladders comprising a material allowing volumetric expansion of the bladders and an aperture providing communication from the interior of the bladder to the exterior of the bladder, wherein at least a first said bladder is connected to a first valve and at least a second said bladder is connected to a second valve, wherein the first and second valves individually control gas flow through the apertures of the first and second said bladders, respectively, wherein at least the first bladder and at least the second bladder are partially overlapping upon inflation, and wherein the garment further comprises:
   (c) an inflation system comprising a cartridge comprising a gas or gas-generating agent connected to said two or more bladders by a first tube network of at least two tubes, wherein at least a first said tube is connected to the first valve and at least a second said tube is connected to the second valve;
   (d) an information processing unit (IPU) that is independently connected to the first and second regions of the array of impact detection sensors, wherein activation of the impact detection sensors of the first region transmits a signal to the IPU that opens the first valve, thereby causing inflation of at least the first bladder by the cartridge, and activation of the second region transmits a signal to the IPU that opens the second valve, thereby causing inflation of at least the second bladder by the cartridge; and
   (e) an outer layer covering the front and back parts and comprising a durable material that constrains outward expansion of the garment when worn by a subject upon inflation of at least one of the two or more bladders, whereby, upon inflation, at least one of the two or more bladders is configured to expand to a volume effective to exert localized pressure at or near the site of the impact in a direction opposite the outer layer, thereby reducing hemorrhage.

2. The garment of claim 1, wherein:
   (a) said impact detection sensor is a piezoelectric system, a network of fluid-carrying tubes, and/or a conductive material;
   (b) said first tube network further comprises an aperture and a valve controlling gas flow through the aperture; and
   (c) said device further comprises an energy source, a GPS unit, or a data transmitter.

3. The garment of claim 1, wherein said gas is pressurized and is selected from the group consisting of carbon dioxide, nitrogen, oxygen, and hydrogen or is a non-flammable or inert gas, and, when activated by said IPU, one or more of said bladders are configured to be inflated by said pressurized gas or gas evolved by said gas-generating agent.

4. The garment of claim 3, wherein said gas-generating agent is selected from the group consisting of an alkali metal chlorate, an alkali metal perchlorate, a peroxide, or a superoxide.

5. The garment of claim 2, wherein said garment is configured for use with an inanimate object.

6. The garment of claim 2, wherein said garment is configured as an article of clothing.

7. The garment of claim 2, wherein said piezoelectric system comprises a piezoelectric film and/or said conductive material comprises a network of conductive mesh or layers of material with different conductivity levels.

8. The garment of claim 2, wherein said energy source is a battery powered power supply.

9. The garment of claim 2, wherein said GPS unit is configured for activation in response to a wired or a wireless signal from said impact detection sensors, a manual signal, or by manual activation.

10. The garment of claim 2, wherein said data transmitter is connected to said impact detection sensors by leads selected from the group consisting of wires, conductive thread, and metal pads, or is connected by a wireless signal.

11. The garment of claim 1, further comprising:
   (a) more than one IPU, each said IPU independently connected to one or more said impact detection sensors and being independently programmed to activate said device upon identification of an impact type and/or to determine the location of said impact;
   (b) an amplifier connected to said impact detection system by leads selected from the group consisting of wires, conductive thread, and metal pads;

(c) a controller connected to said amplifier, said controller comprising an analog to digital converter and a compare circuit; and (d) a programmable non-transitory read-only memory system connected to said controller, said memory system comprising parameters in terms of signal amplitude of different impact types, and/or a data storage system to record data from sensor inputs.

12. The garment of claim 11, wherein said garment further comprises a sealant system comprising a container having one or more enclosed compartments comprising a sealant and a trigger for activating the sealant system in response to a signal from said impact detection sensors, whereby activation of the trigger causes release of said sealant proximal to, or at the site of said impact, and wherein:

(a) said trigger for activating said sealant system activates said sealant system prior to, subsequent to, or concurrently with said inflation system; or (b) said trigger for activating said sealant system and said sealant system are connected by leads or by a wireless signal, wherein said leads are selected from the group consisting of wires, conductive thread, and metal pads.

13. The garment of claim 12, wherein said sealant is a wound sealant selected from the group consisting of a biopolymer, a synthetic polymer, a biosynthetic composite, and a mixture thereof.

14. The garment of claim 12, wherein said container further comprises a frangible seal configured to be broken upon activation of said trigger or upon the impact to said device, wherein breakage of the frangible seal releases said sealant.

15. The garment of claim 12, wherein said one or more compartments further comprise one or more apertures communicating from the interior of the compartment to the exterior of the compartment and one or more valves controlling fluid flow through the apertures.

16. The garment of claim 15, wherein said one or more compartments are connected to a second cartridge comprising gas or a gas-generating agent, wherein said second cartridge is connected to said one or more compartments by a second tube network which is connected to the one or more valves of the one or more compartments.

17. The garment of claim 16, wherein:

(a) said gas of the second cartridge is pressurized and is selected from the group consisting of carbon dioxide, nitrogen, oxygen, and hydrogen or is a non-flammable and/or inert gas; or (b) said gas-generating agent of the second cartridge is selected from the group consisting of an alkali metal chlorate, an alkali metal perchlorate, a peroxide, and a superoxide.

18. The garment of claim 12, wherein said first layer and said second layer further comprise said sealant system.

19. The garment of claim 12, wherein said sealant is a gel or film, a liquid sealant, or a solid sealant.

20. The garment of claim 12, wherein said sealant is selected from the group consisting of a fibrin liquid or solid sealant, a collagen mixture, a gelatin solution or dispersion, an albumin solution, and a chitosan solution.

21. The garment of claim 2, wherein said data transmitter is configured for activation in response to a signal from said impact detection sensors and, upon said activation, said data transmitter is configured to transmit status and/or identity information.

22. The garment of claim 1, wherein said garment is configured as an article of clothing that covers the torso or is selected from the group consisting of headgear, a vest, a jacket, pants, or a full body suit.

23. The garment of claim 1, wherein, upon inflation and when worn by the subject, the two or more bladders of the garment are configured to exert a pressure against the subject at an impact site of about 220-240 mm Hg over normal atmospheric pressure of 760 mm Hg.

24. The garment of claim 1, wherein, upon inflation, the bladders are configured to inflate to a pressure of about 2 to about 120 psi.

25. The garment of claim 1, wherein the mammal is a human or dog.

26. The garment of claim 25, wherein, upon inflation, the two or more bladders are configured to exert pressure against the human, thereby reducing hemorrhage caused by the impact.

27. The garment of claim 26, wherein the hemorrhage is at an impact site.

28. The garment of claim 1, wherein the device further comprises an inner layer, wherein the two or more bladders are positioned between the inner and outer layers.

29. The garment of claim 28, wherein the inner layer comprises a polyester, an acrylic, a nylon, a rayon, spandex, a polyurethane fiber or fabric, a polytetrafluoroethylene, or a para-aramid synthetic fiber.

30. The garment of claim 1, wherein the outer layer comprises a textile, rubber, leather, a polymer mix, para-aramid synthetic fiber, artificial spider silk, a nanocomposite, or a carbon fiber.

31. The garment of claim 1, further comprising a sealant system.

32. The garment of claim 31, wherein the sealant system comprises a sealant within the first tube network.

33. The garment of claim 1, wherein said device is configured for manual activation.

34. The garment of claim 1, further comprising a processor for collecting and transmitting data.

35. The garment of claim 1, wherein the localized pressure comprises compression.

36. The garment of claim 1, wherein the bladders are from 1 mm to 10 mm in thickness in the uninflated state, and from 1 cm to 10 cm in thickness in the inflated state.

37. The garment of claim 1, where the first said bladder is colocalized with the first region of said array and the second said bladder is colocalized with the second region of said array.

38. The garment of claim 1, wherein the back part comprises an impact detection device comprising:

(a) a first layer comprising an array of impact detection sensors defining at least first and second non-overlapping regions that are configured to independently activate upon an impact thereto; and (b) a second layer adjacent to the first layer comprising two or more bladders, each of said bladders comprising a material allowing volumetric expansion of the bladders and an aperture providing communication from the interior of the bladder to the exterior of the bladder, wherein at least a first said bladder is connected to a third valve and at least a second said bladder is connected to a fourth valve, wherein the first and second valves individually control gas flow through the apertures of the first and second said bladders, respectively, wherein at least the first bladder and at least the second bladder are partially overlapping;

wherein the inflation system of the garment is connected to said two or more bladders of the back part by a first tube network of at least two tubes, wherein at least a first said tube is connected to the third valve and at least a second said tube is connected to the fourth valve; and wherein the IPU is independently connected to the first and second regions of the array of impact detection sensors of the back part, wherein activation of the impact detection sensors of the first region transmits a signal to the IPU that opens the third valve, thereby causing inflation of at least the first bladder of the back part by the cartridge, and activation of the second region transmits a signal to the IPU that opens the fourth valve, thereby causing inflation of at least the second bladder of the back part by the cartridge.

39. The garment of claim 38, wherein the back part comprises a separate inflation system comprising the cartridge comprising the gas or gas-generating agent connected to said two or more bladders of the back.

40. The garment of claim 38, wherein the back part comprises a separate IPU independently connected to said first and second regions of the array of impact detection sensors of the back.

* * * * *